United States Patent
Kim et al.

(10) Patent No.: US 9,905,786 B2
(45) Date of Patent: Feb. 27, 2018

(54) ORGANOMETALLIC COMPLEX AND ORGANIC LIGHT-EMITTING DEVICE INCLUDING THE SAME

(71) Applicants: SAMSUNG DISPLAY CO., LTD., Yongin-si, Gyeonggi-do (KR); KOREA ADVANCED INSTITUTE OF SCIENCE AND TECHNOLOGY, Daejeon (KR)

(72) Inventors: Younsun Kim, Yongin-si (KR); Yunho Lee, Daejeon (KR); Jihyun Seo, Yongin-si (KR); Seulong Kim, Yongin-si (KR); Yeong-Eun Kim, Daejeon (KR); Dongwoo Shin, Yongin-si (KR); Jungsub Lee, Yongin-si (KR); Naoyuki Ito, Yongin-si (KR); Changwoong Chu, Yongin-si (KR)

(73) Assignees: Samsung Display Co., Ltd., Yongin-si (KR); Korea Advanced Institute of Science and Technology, Daejeon (KR)

( * ) Notice: Subject to any disclaimer, the term of this patent is extended or adjusted under 35 U.S.C. 154(b) by 180 days.

(21) Appl. No.: 14/857,785

(22) Filed: Sep. 17, 2015

(65) Prior Publication Data
US 2016/0079549 A1    Mar. 17, 2016

(30) Foreign Application Priority Data

Sep. 17, 2014 (KR) .................. 10-2014-0123707
Sep. 8, 2015 (KR) .................. 10-2015-0127033

(51) Int. Cl.
*H01L 51/00* (2006.01)
*C07F 9/6568* (2006.01)
(Continued)

(52) U.S. Cl.
CPC ........ *H01L 51/0091* (2013.01); *C07F 9/6587* (2013.01); *C09K 11/025* (2013.01);
(Continued)

(58) Field of Classification Search
None
See application file for complete search history.

(56) References Cited

U.S. PATENT DOCUMENTS 7,361,414 B2   4/2008   Tsuboyama et al.
8,039,123 B2   10/2011  Ragini et al.
(Continued)

FOREIGN PATENT DOCUMENTS

DE   11 2011 101 983 T5   6/2013
EP        278758 A2 *   8/1988
(Continued)

OTHER PUBLICATIONS

Baldo, M. A., et al., Excitonic singlet-triplet ratio in a semiconducting organic thin film, *Physical Review B*, Nov. 15, 1999, pp. 14 422-14 428, vol. 60, No. 20, The American Physical Society.
Harkins, Seth B., et al., A Highly Emissive $Cu_2N_2$ Diamond Core Complex Supported by a [PNP]⁻ Ligand, *J. Am. Chem. Soc.*, 2005, pp. 2030-2031, vol. 127, No. 7.
Igawa, Satoshi, et al., Highly efficient green organic light-emitting diodes containing luminescent tetrahedral copper(I) complexes, Journal of Materials Chemistry C, 2013, pp. 542-551, vol. 1, The Royal Society of Chemistry 2013.
Roderiques, Sara, Luminescent Copper(I) Complexes, 10 pgs, engineering.dartmouth.edu/reu/2009/Roderiques-Paper.pdf, Date: 2009.

*Primary Examiner* — Dawn Garrett
(74) *Attorney, Agent, or Firm* — Lewis Roca Rothgerber Christie LLP

(57) ABSTRACT

An organometallic complex represented by Formula 1-1 or Formula 1-2 is provided:

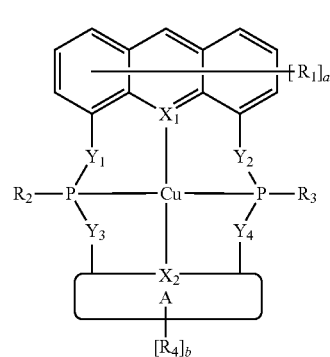

Formula 1-1

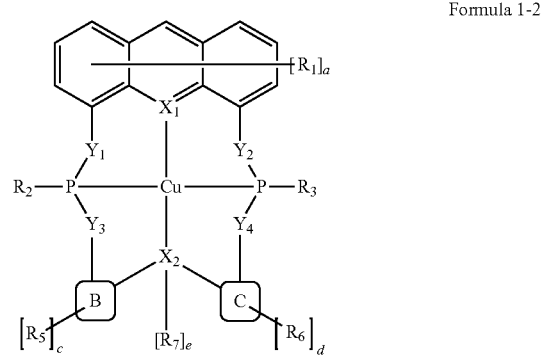

Formula 1-2 wherein in Formulae 1-1 and 1-2, descriptions of $R_1$ to $R_7$, $X_1$, $X_2$, $Y_1$ to $Y_4$, rings A, B, C, and a to e are understood by referring to the description provided herein. An organic light-emitting device includes a first electrode, a second electrode facing the first electrode, and an organic layer that is disposed between the first electrode and the second electrode and includes an emission layer, wherein the organic layer includes at least one organometallic complex represented by Formula 1-1 or Formula 1-2.

20 Claims, 1 Drawing Sheet

(51) Int. Cl.

| | | |
|---|---|---|
| *C09K 11/02* | (2006.01) | |
| *C07F 9/28* | (2006.01) | |
| *C07F 9/64* | (2006.01) | |
| *C09K 11/06* | (2006.01) | |
| *C07F 9/6587* | (2006.01) | |
| *H01L 51/50* | (2006.01) | |

(52) U.S. Cl.
 CPC ...... *C09K 11/06* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/188* (2013.01); *H01L 51/5016* (2013.01)

(56) References Cited

U.S. PATENT DOCUMENTS

| | | |
|---|---|---|
| 2007/0111026 A1 | 5/2007 | Deaton et al. |
| 2008/0064893 A1 | 3/2008 | Peters et al. |
| 2008/0199731 A1 | 8/2008 | Vogler et al. |
| 2010/0217023 A1 | 8/2010 | Peters et al. |
| 2011/0089818 A1 | 4/2011 | Peters et al. |
| 2011/0304262 A1 | 12/2011 | Kwong |
| 2012/0181515 A1 | 7/2012 | Wada et al. |

FOREIGN PATENT DOCUMENTS

| | | |
|---|---|---|
| JP | 2012-151271 A | 8/2012 |
| KR | 10-2013-0094217 A | 8/2013 |
| WO | WO 2011/156752 A1 | 12/2011 |

\* cited by examiner

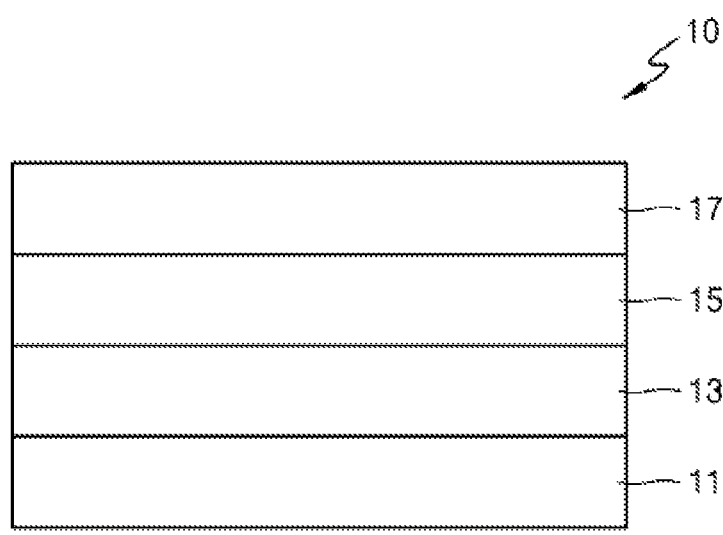

ORGANOMETALLIC COMPLEX AND ORGANIC LIGHT-EMITTING DEVICE INCLUDING THE SAME

CROSS-REFERENCE TO RELATED APPLICATION

This application claims the benefit of Korean Patent Application No. 10-2014-0123707, filed on Sep. 17, 2014, and Korean Patent Application No. 10-2015-0127033, filed on Sep. 8, 2015, in the Korean Intellectual Property Office, the entire content of both of which is incorporated herein by reference.

BACKGROUND

1. Field

One or more exemplary embodiments relate to an organometallic complex and an organic light-emitting device including the same.

2. Description of the Related Art

Organic light-emitting devices are self-emission devices that have wide viewing angles, high contrast ratios, short response times, and excellent brightness, driving voltage, and response speed characteristics, and produce full-color images.

An organic light-emitting device may have a structure including an anode disposed on a substrate, and a hole transport layer, an emission layer, an electron transport layer, and a cathode, which are sequentially disposed on the anode. The hole transport layer, the emission layer, and the electron transport layer may be organic thin films formed of organic compounds.

The organic light-emitting device having the structure described above has a driving principle as follows.

When a voltage is applied between the anode and the cathode, holes provided from the anode may move toward the emission layer through the hole transport layer and electrons provided from the cathode may move toward the emission layer through the electron transport layer. Carriers, such as holes and electrons, are recombined in the mission layer to produce excitons. These excitons change from an excited state to a ground state, thereby generating light.

An organic light-emitting diode including an iridium complex phosphorescent dopant shows high external quantum efficiency of 20% or more. However, a heavy metal including iridium is expensive and there is great concern about environmental pollution by using such a heavy metal. Accordingly, the development of various suitable organic metal complexes is required.

SUMMARY

One or more exemplary embodiments include an organic light-emitting device having a high efficiency.

Additional aspects of embodiments will be set forth in part in the description which follows and, in part, will be apparent from the description, or may be learned by practice of the presented embodiments.

According to one or more exemplary embodiments, there is provided an organometallic compound represented by Formula 1-1 or Formula 1-2 below:

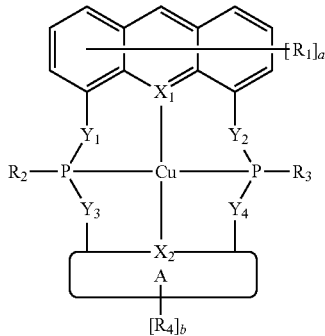

Formula 1-1

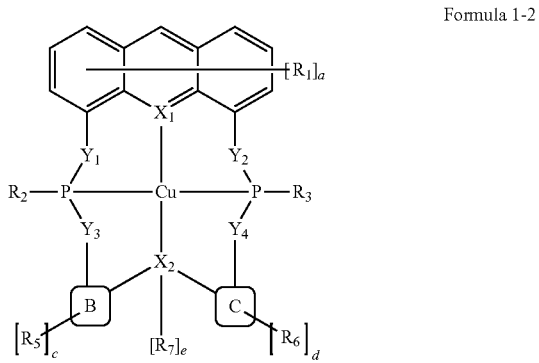

Formula 1-2 wherein in Formulae 1-1 and 1-2, a ring A is a condensed ring including $X_2$, a ring B and a ring C are each independently a substituted or unsubstituted $C_6$-$C_{40}$ aromatic ring, a substituted or unsubstituted $C_1$-$C_{40}$ hetero aromatic ring, or a substituted or unsubstituted $C_3$-$C_{10}$ cycloalkene group, $X_1$ is carbon (C), nitrogen (N), or phosphorus (P), and $X_2$ is C, N, P, oxygen (O) or sulfur (S), $Y_1$ to $Y_4$ are each independently a direct bond, O, S, a substituted or unsubstituted $C_1$-$C_{10}$ alkylene group, a substituted or unsubstituted $C_6$-$C_{40}$ arylene group, or a substituted or unsubstituted $C_1$-$C_{40}$ heteroarylene group, $R_1$ to $R_6$ are each independently selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_1$-$C_{10}$ heterocycloalkyl group, a substituted or unsubstituted $C_1$-$C_{10}$ heterocycloalkenyl group, a substituted or unsubstituted $C_6$-$C_{40}$ aryl group, a substituted or unsubstituted $C_1$-$C_{40}$ heteroaryl group, a substituted or unsubstituted $C_6$-$C_{40}$ aryloxy group, a substituted or unsubstituted $C_6$-$C_{40}$ arylthio group, —$N(Q_1)(Q_2)$, —$C(=O)(Q_3)$, and —$Si(Q_4)(Q_5)(Q_6)$ (wherein $Q_1$ to $Q_6$ are each independently a hydrogen, a substituted or unsubstituted $C_1$-$C_{20}$ alkyl group, a substituted or unsubstituted $C_6$-$C_{40}$ aryl group, or a substituted or unsubstituted $C_2$-$C_{40}$ heteroaryl group), wherein, optionally, $R_2$ and $R_3$ are each independently (=O), $R_7$ is a substituted or unsubstituted $C_6$-$C_{40}$ aryl group or a substituted or unsubstituted $C_1$-$C_{40}$ heteroaryl group, a is an integer of 1 to 7, and when a is 2 or more, a plurality of $R_1$s may be independent of each other (e.g., the plurality of $R_1$s may be the same as or different from one another), b is an integer of 1 to 7, and when b is 2 or more, a plurality of $R_4$s may be independent of each other (e.g., the plurality of $R_4$s may be the same as or different from one another), c is an integer of 1 to 4, and when c is 2 or more, a plurality of $R_5$s may be independent of each other (e.g., the plurality of $R_5$s may be the same as or different from one another), d is an integer of 1 to 4, and when d is 2 or more, a plurality of $R_6$s may be independent of each other (e.g., the plurality of $R_6$s may be the same as or different from one another), and e is 0 or 1.

According to one or more exemplary embodiments, there is provided an organic light-emitting device including a first electrode, a second electrode facing the first electrode, and an organic layer that is disposed between the first electrode and the second electrode and includes an emission layer, wherein the organic layer includes at least one organometallic complex represented by Formula 1-1 or Formula 1-2.

BRIEF DESCRIPTION OF THE DRAWINGS

These and/or other aspects will become apparent and more readily appreciated from the following description of the exemplary embodiments, taken in conjunction with the accompanying drawing which is a schematic view of an organic light-emitting device according to an embodiment.

DETAILED DESCRIPTION

Reference will now be made in more detail to exemplary embodiments, examples of which are illustrated in the accompanying drawing. In this regard, the present exemplary embodiments may have different forms and should not be construed as being limited to the descriptions set forth herein. Accordingly, the exemplary embodiments are merely described below, by referring to the accompanying drawing, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

An organometallic complex according to an embodiment may be represented by Formula 1-1 or Formula 1-2 below:

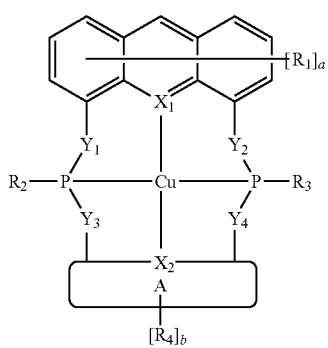

Formula 1-1

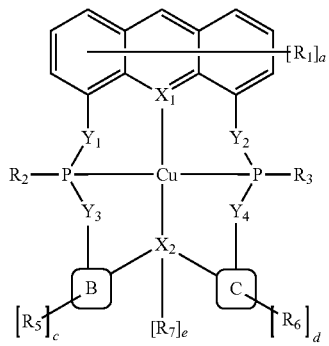

Formula 1-2

In Formulae 1-1 and 1-2, a ring A may be a condensed ring including $X_2$, a ring B and a ring C may each be independently a substituted or unsubstituted $C_6$-$C_{40}$ aromatic ring, a substituted or unsubstituted $C_1$-$C_{40}$ hetero aromatic ring, or a substituted or unsubstituted $C_3$-$C_{10}$ cycloalkene, $X_1$ may be carbon (C), nitrogen (N), or phosphorus (P), and $X_2$ may be C, N, P, oxygen (O), or sulfur (S), $Y_1$ to $Y_4$ may each be independently a direct bond, O, S, a substituted or unsubstituted $C_1$-$C_{10}$ alkylene group, a substituted or unsubstituted $C_6$-$C_{40}$ arylene group, or a substituted or unsubstituted $C_1$-$C_{40}$ heteroarylene group.

The ring A in Formula 1-1 may be linked to $Y_3$ and $Y_4$, and $R_4$ may be a substituent of the ring A in a case where b is not 0. The ring B in Formula 1-2 may be linked to $Y_3$ and $X_2$, and $R_5$ may be a substituent of the ring B in a case where c is not 0. The ring C in Formula 1-2 may be linked to $Y_4$ and $X_2$, and $R_6$ may be a substituent of the ring C in a case where d is not 0.

In Formulae 1-1 and 1-2, $R_1$ to $R_6$ may each be independently selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_1$-$C_{10}$ heterocycloalkyl group, a substituted or unsubstituted $C_1$-$C_{10}$ heterocycloalkenyl group, a substituted or unsubstituted $C_6$-$C_{40}$ aryl group, a substituted or unsubstituted $C_1$-$C_{40}$ heteroaryl group, a substituted or unsubstituted $C_6$-$C_{40}$ aryloxy group, a substituted or unsubstituted $C_6$-$C_{40}$ arylthio group, —$N(Q_1)(Q_2)$, —$C(=O)(Q_3)$, and —$Si(Q_4)(Q_5)(Q_6)$ (wherein $Q_1$ to $Q_6$ may each be independently a hydrogen, a substituted or unsubstituted $C_1$-$C_{20}$ alkyl group, a substituted or unsubstituted $C_6$-$C_{40}$ aryl group, or a substituted or unsubstituted $C_2$-$C_{40}$ heteroaryl group), wherein $R_2$ and $R_3$ may each optionally be (=O), and $R_7$ may be a substituted or unsubstituted $C_6$-$C_{40}$ aryl group or a substituted or unsubstituted $C_2$-$C_{40}$ heteroaryl group.

In the formulae above, a may indicate the number of $R_1$, and may be an integer of 0 to 7. When a is 2 or more, a plurality of $R_1$s may be identical to or different from each other (e.g., the plurality of $R_1$s may be the same as or different from one another).

In the formulae above, b may indicate the number of $R_4$, and may be an integer of 0 to 7. When b is 2 or more, a plurality of $R_4$s may be identical to or different from each other (e.g., the plurality of $R_4$s may be the same as or different from one another).

In the formulae above, c may indicate the number of $R_5$, and may be an integer of 0 to 4. When c is 2 or more, a plurality of $R_5$s may be identical to or different from each other (e.g., the plurality of $R_5$s may be the same as or different from one another).

In the formulae above, d may indicate the number of $R_6$, and may be an integer of 0 to 4. When d is 2 or more, a plurality of $R_6$s may be identical to or different from each other (e.g., the plurality of $R_6$s may be the same as or different from one another).

In the formulae above, e may be 0 or 1, and $X_2$ may be only linked to the ring B and the C in a case where e is 0.

In Formulae 1-1 and 1-2, $R_1$ to $R_6$ may be selected from:
a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a $C_6$-$C_{40}$ aryl group and a $C_1$-$C_{40}$ heteroaryl group, a $C_6$-$C_{40}$ aryl group and a $C_1$-$C_{40}$ heteroaryl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{40}$ aryl group, and a $C_1$-$C_{40}$ heteroaryl group, and

—N($Q_1$)($Q_2$), wherein, optionally, $R_2$ and $R_3$ may each be independently (=O), and $Q_1$ to $Q_2$ may each be independently selected from:
a hydrogen atom, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a $C_6$-$C_{40}$ aryl group and a $C_1$-$C_{40}$ heteroaryl group, a $C_6$-$C_{40}$ aryl group and a $C_1$-$C_{40}$ heteroaryl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{40}$ aryl group, and a $C_1$-$C_{40}$ heteroaryl group.

In the formulae above, $R_7$ may be selected from:
a $C_6$-$C_{40}$ aryl group and a $C_1$-$C_{40}$ heteroaryl group, and a $C_6$-$C_{40}$ aryl group and a $C_1$-$C_{40}$ heteroaryl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{40}$ aryl group, and a $C_1$-$C_{40}$ heteroaryl group.

In the formulae above, $R_1$ to $R_3$ may each be, for example, independently selected from:

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonenyl group, an isononenyl group, a sec-nonenyl group, a tert-nonenyl group, an n-decanyl group, an isodecanyl group, a sec-decanyl group, and a tert-decanyl group;

a phenyl group, a naphthyl group, an anthryl group, a pyrenyl group, a phenanthrenyl group, a fluorenyl group, an indenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group; and a phenyl group substituted with at least one fluorine (F), a naphthyl group, an anthryl group, a pyrenyl group, a phenanthrenyl group, a fluorenyl group, an indenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group.

In the formulae above, $R_4$ to $R_6$ may each be, for example, independently selected from:

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonenyl group, an isononenyl group, a sec-nonenyl group, a tert-nonenyl group, an n-decanyl group, an isodecanyl group, a sec-decanyl group, a tert-decanyl group, a methoxy group, an ethoxy group, a propoxy group, n-butoxy group, an isobutoxy group, a sec-butoxy group, and a tert-butoxy group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonenyl group, an isononenyl group, a sec-nonenyl group, a tert-nonenyl group, an n-decanyl group, an isodecanyl group, a sec-decanyl group, a tert-decanyl group, a methoxy group, an ethoxy group, a propoxy group, n-butoxy group, an isobutoxy group, a sec-butoxy group, and a tert-butoxy group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a naphthyl group, an anthryl group, a pyrenyl group, a phenanthrenyl group, a fluorenyl group, an indenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group, and a phenyl group, a naphthyl group, an anthryl group, a pyrenyl group, a phenanthrenyl group, a fluorenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyrenyl group, a phenanthrenyl group, a fluorenyl group, an indenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group.

In the formulae above, $R_7$ may be, for example, selected from a phenyl group, a naphthyl group, an anthryl group, a pyrenyl group, a phenanthrenyl group, a fluorenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group.

In Formula 1-1, the ring A including $X_2$ may be an anthracene, an acridine, an acridophosphine, a xanthene, or a thioxanthene.

In Formula 1-2, the ring B and the ring C may each be independently selected from a benzene, a naphthylene, an indene, a cyclopentadiene, a benzoimidazole, a pyrrole, an imidazole, a pyrazole, a triazole, a thiazole, an oxazole, an isothiazole, an isoxazole, a benzothiazole, a benzoxazole, a pyridine, a pyrazine, a pyrimidine, a pyridazine, an iso-indole, an indole, an indazole, a purine, an isoquinoline, a quinoline, a phthalazine, a naphthyridine, a quinoxaline, a quinazoline, a cinnoline, a phenanthridine, an acridine, a phenanthroline, a phenazine, a phenoxazine, and a phenoxazine.

For example, in Formula 1-1, the ring A may be an anthracene, an acridine, or an acridophosphine.

For example, in Formula 1-2, the ring B and the ring C may each be independently a benzene, a naphthylene, an indene, a cyclopentadiene, and a benzoimidazolyl.

In Formulae 1-1 and 1-2, the portion

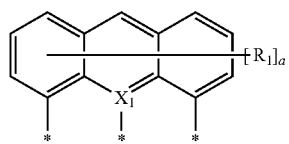

may be represented by one of Formulae 2A to 2G below:

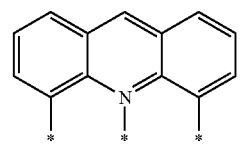
2A

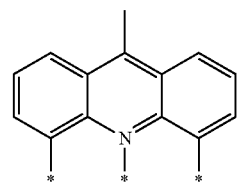
2B

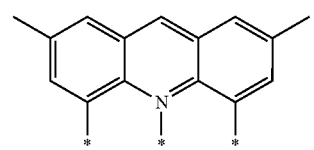
2C

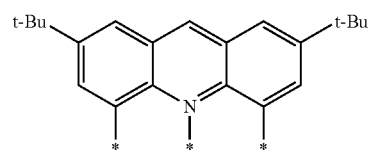
2D

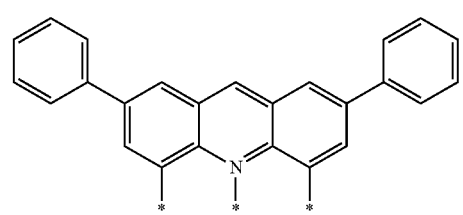
2E

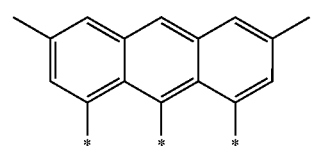
2F

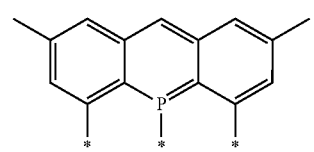
2G

In Formulae 2A to 2G, the three asterisks (*) each indicate, from left to right, a binding site to $Y_1$, $X_1$, and $Y_2$, respectively (e.g., the left asterisk represents a binding site to $Y_1$, the middle asterisk represents a binding site to $X_1$, and the right asterisk represents a binding site to $Y_2$).

In Formulae 1-1 and 1-2, $Y_1$ to $Y_4$ may each be independently a direct bond (as used herein, the term "a directed bond" may refer to "a single bond"). In some embodiments, $Y_1$ and $Y_2$ may each be independently —$CH_2$—, and $Y_3$ and $Y_4$ may each be independently a direct bond. In some embodiments, $Y_1$ and $Y_2$ may each be independently a direct bond, and $Y_3$ and $Y_4$ may each be independently —$CH_2$—. In some embodiments, $Y_1$ and $Y_2$ may each be independently —O—, and $Y_3$ and $Y_4$ may each be independently a direct bond. In some embodiments, $Y_1$ to $Y_4$ may each be independently In the formulae above, $R_2$ and $R_3$ may each be independently an iso-propyl group, a phenyl group, (=O), or 4-fluorophenyl group.

In Formula 1-1, the portion

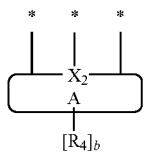

may be represented by one of Formulae 3A to 3C below:

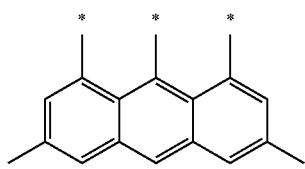

3A

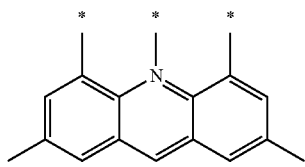

3B

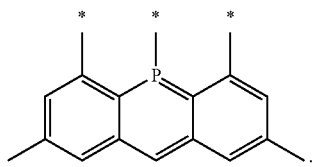

3C

In Formulae 3A to 3C, the three 3 asterisks (*) each indicate, from left to right, a binding site to $Y_3$, $X_2$, and $Y_4$, respectively (e.g., the left asterisk represents a binding site to $Y_3$, the middle asterisk represents a binding site to $X_2$, and the left asterisk represents a binding site to $Y_4$).

In Formula 1-2, the portion

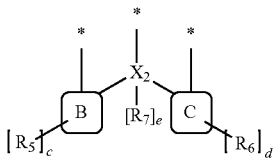

may be represented by one of Formulae 4A to 4I below:

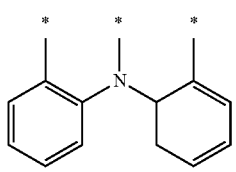

4A

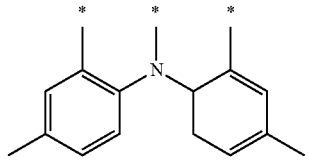

4B

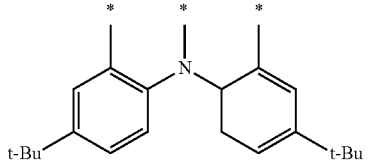

4C

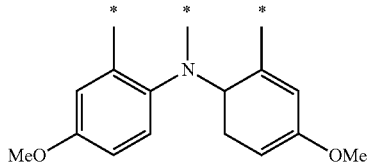

4D

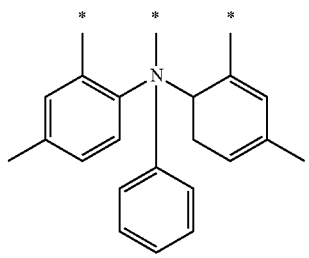

4E

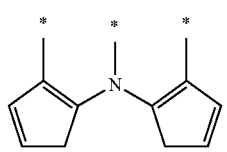

4F

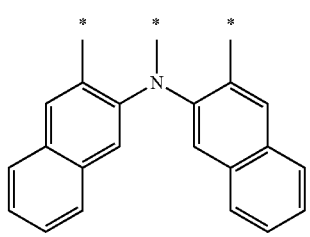

4G

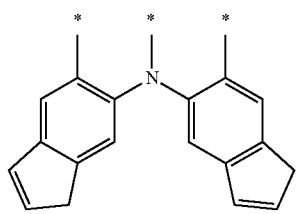

4H

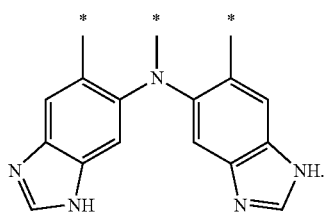

In Formulae 4A to 4I, the three asterisks (*) each indicate, from left to right, a binding site to $Y_3$, $X_2$, and $Y_4$, respectively (e.g., the left asterisk represents a binding site to $Y_3$, the middle asterisk represents a binding site to $X_2$, and the right asterisk represents a binding site to $Y_4$).

The organometallic complex may be one of Compounds 1 to 61 below, but the organometallic complex is not limited thereto:

1

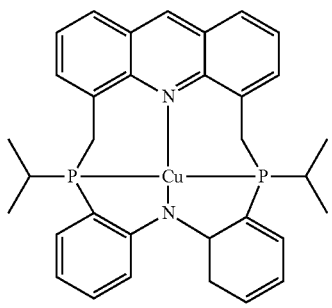

2

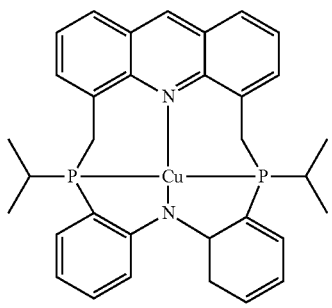

3

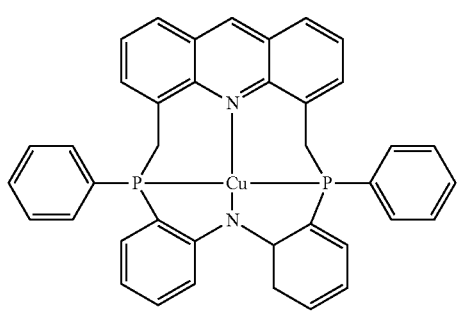

4

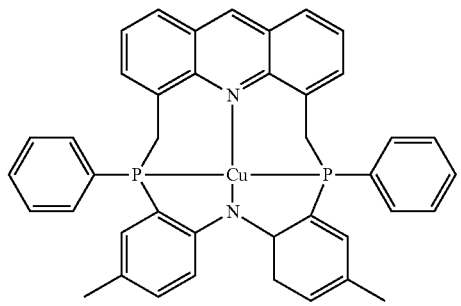

5

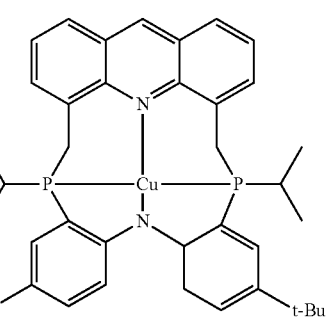

6

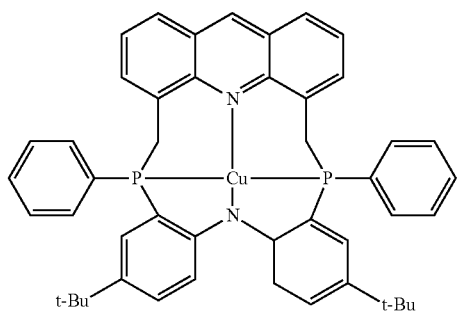

7

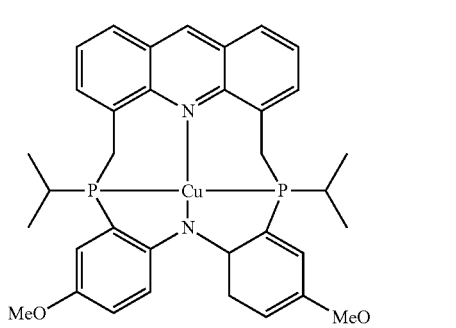

8

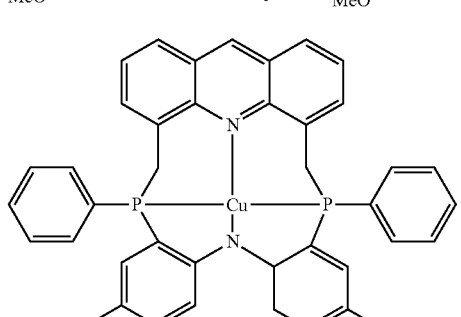

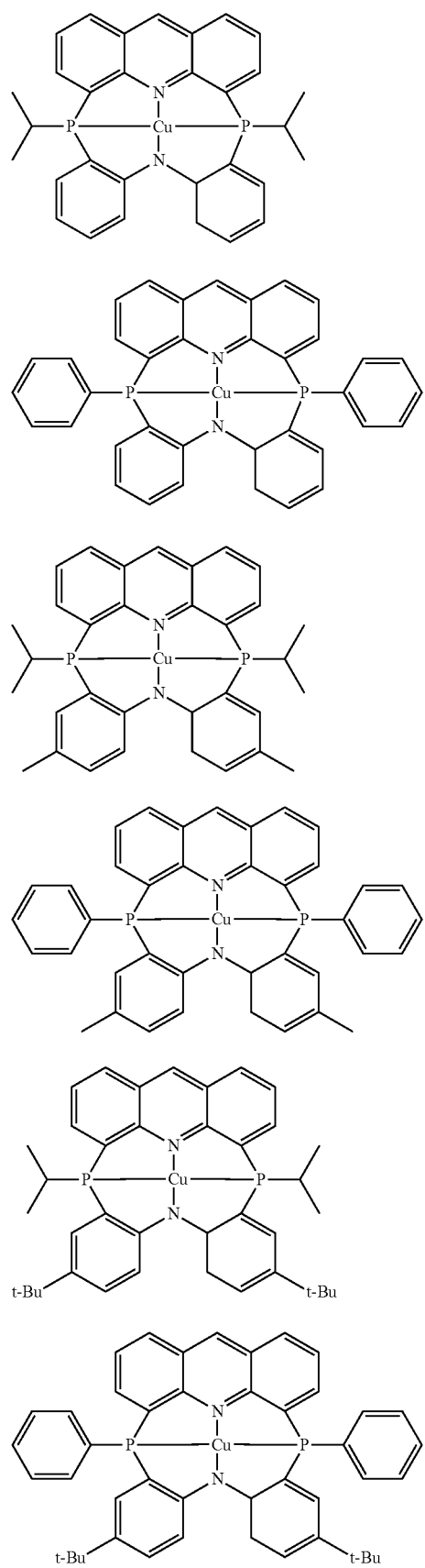
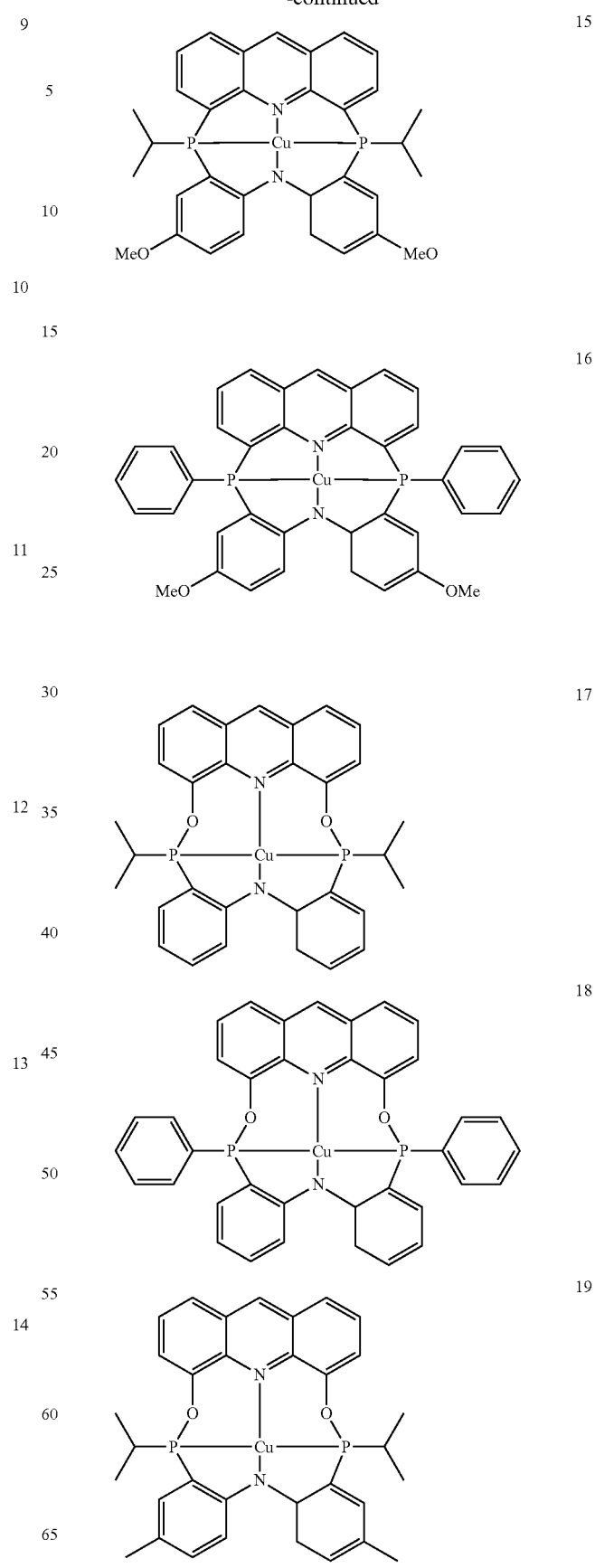

15
-continued
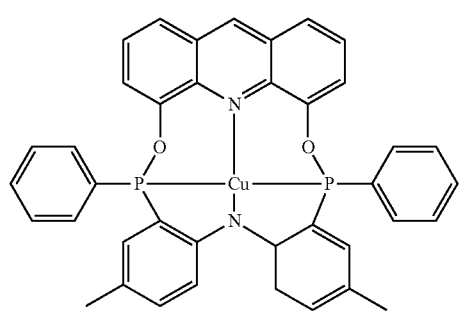
20
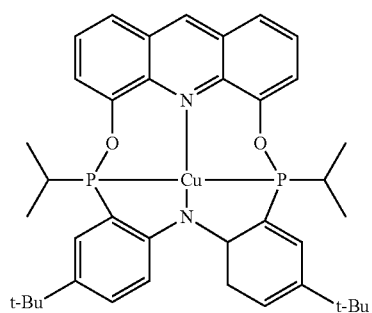
21
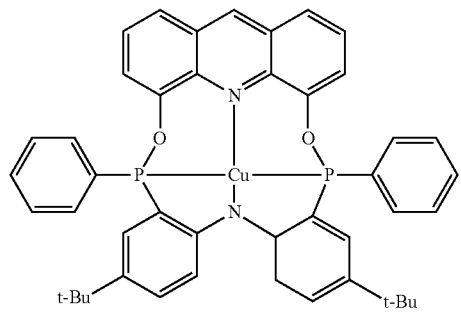
22
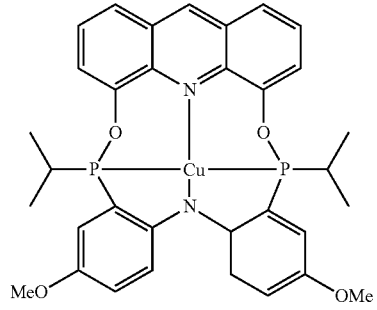
23
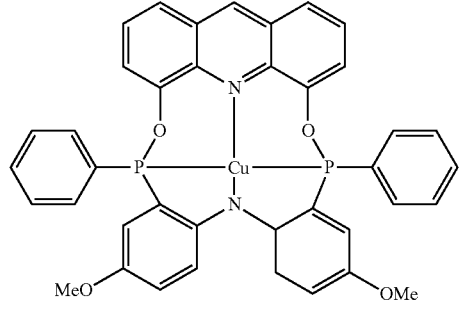
24
16
-continued
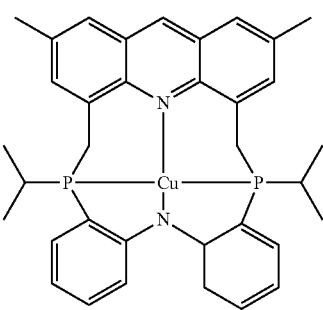
25
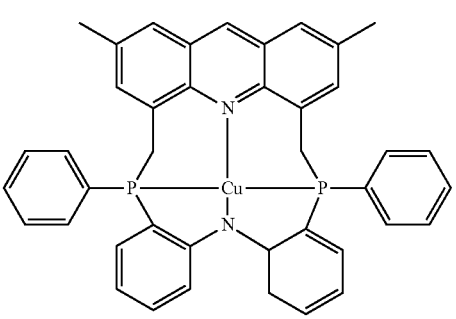
26
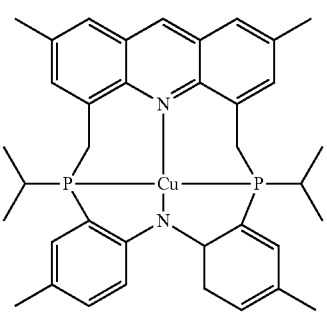
27
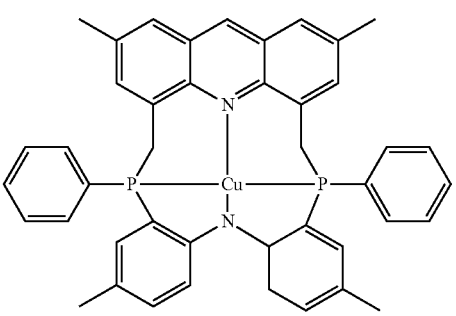
28
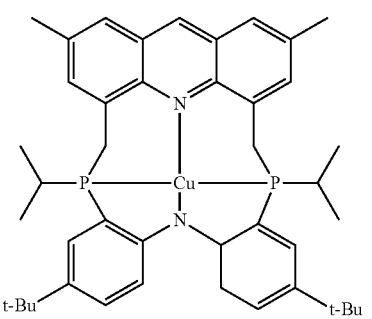
29

| | |
|---|---|
| 30 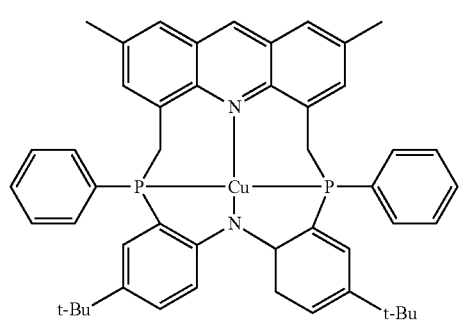 | 35 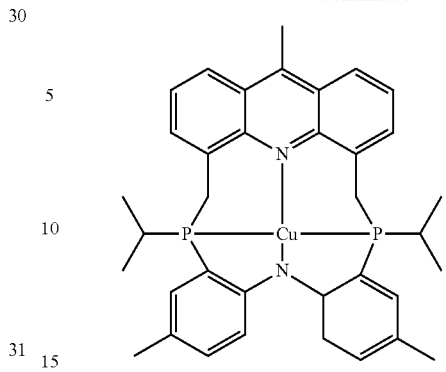 |
| 31 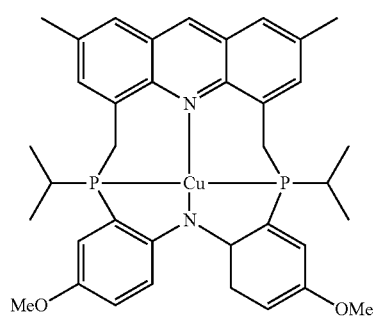 | 36 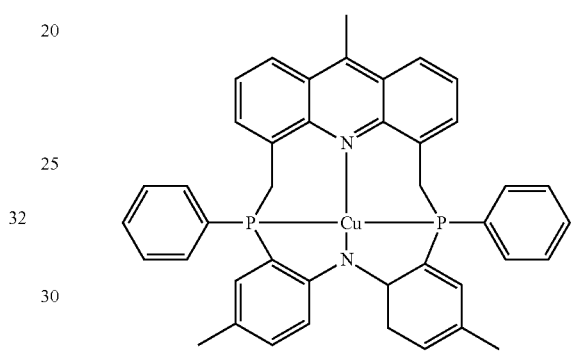 |
| 32 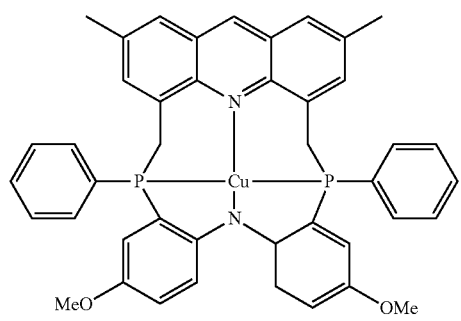 | 37 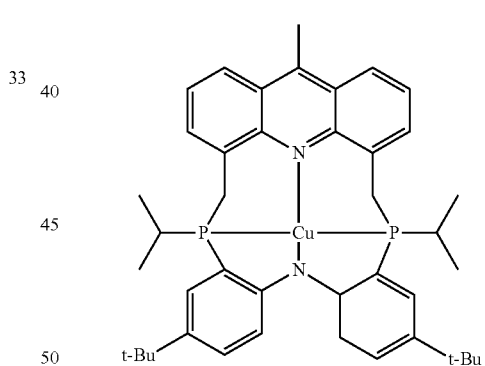 |
| 33 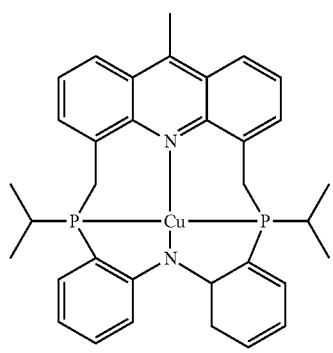 | 38 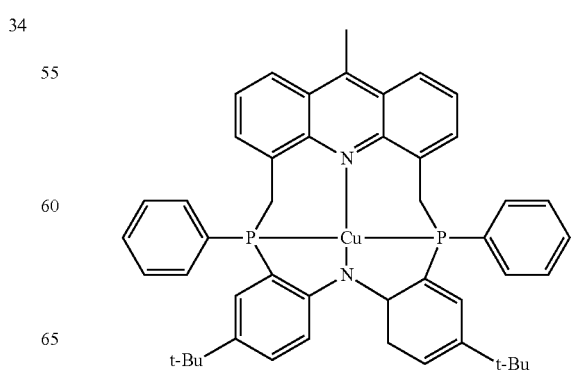 |
| 34 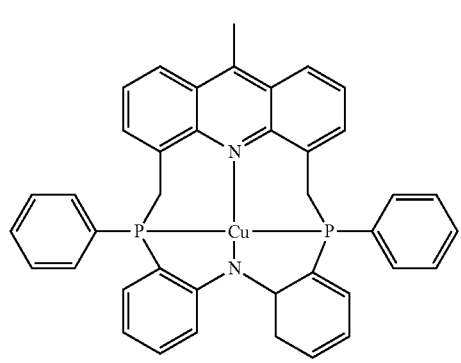 | |

39
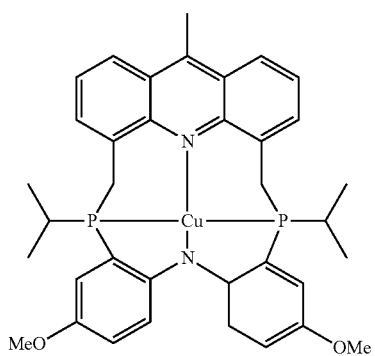
40
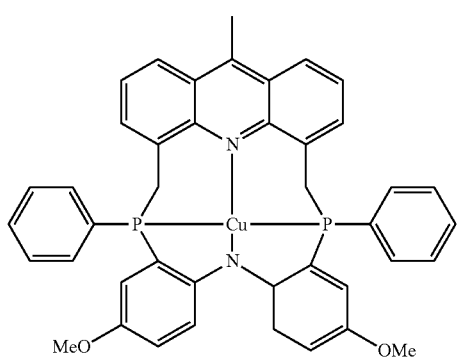
41
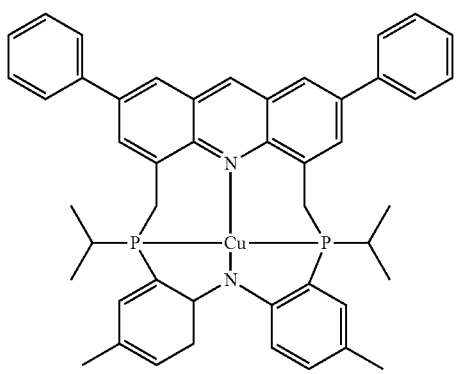
42
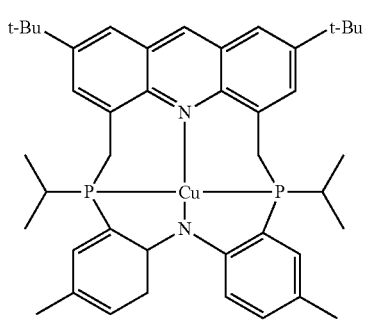
43
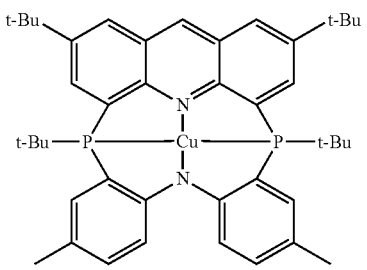
44
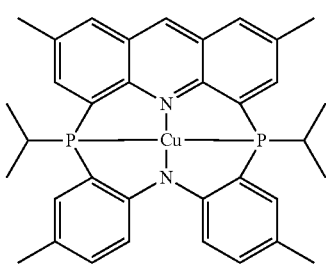
45
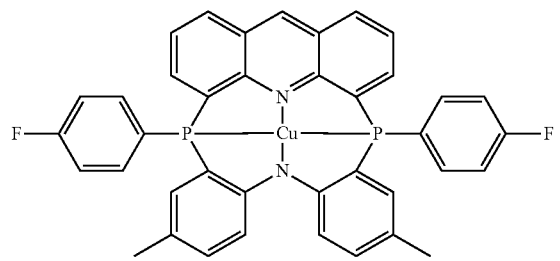
46
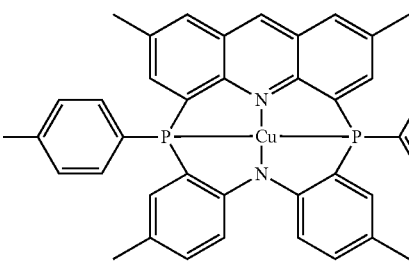
47
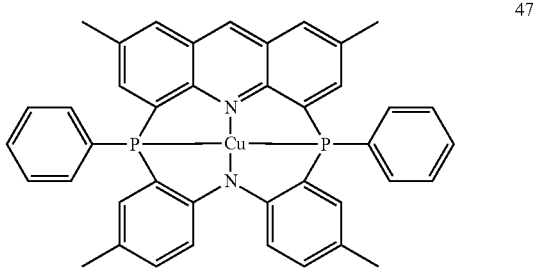
48
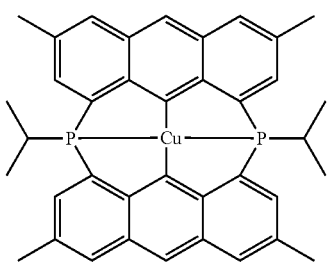

49
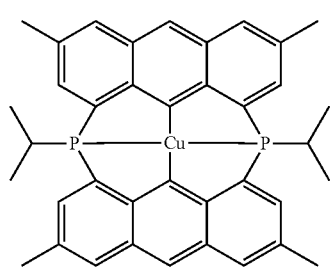
50
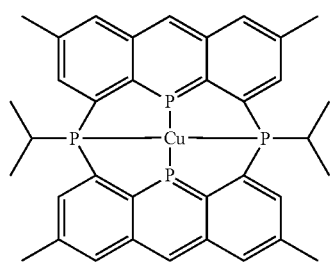
51
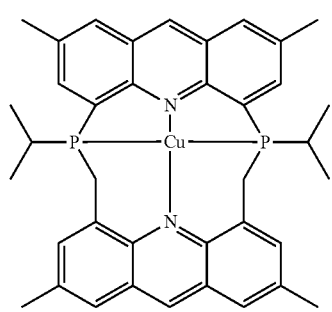
52
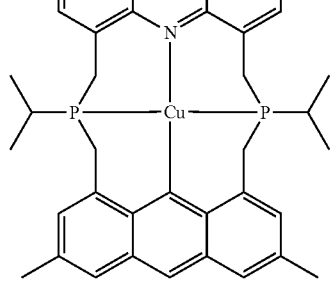
53
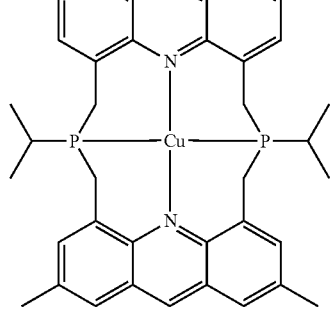
54
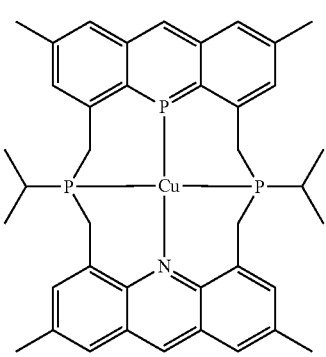
55
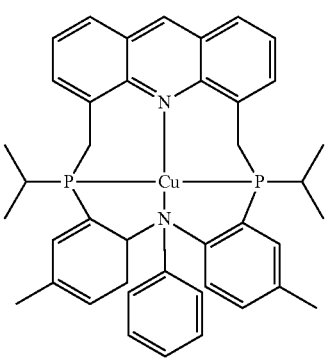
56
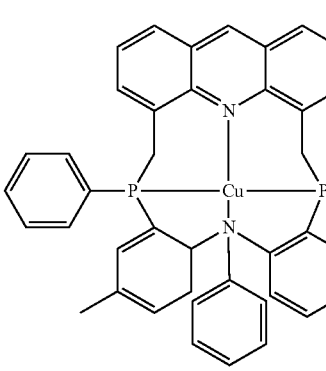
57
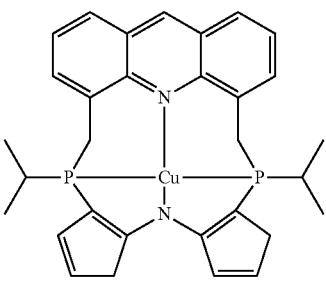
58
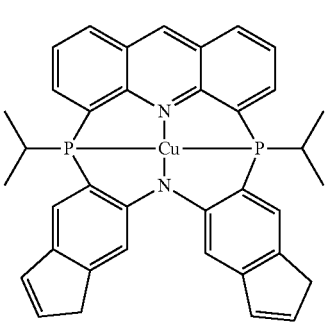

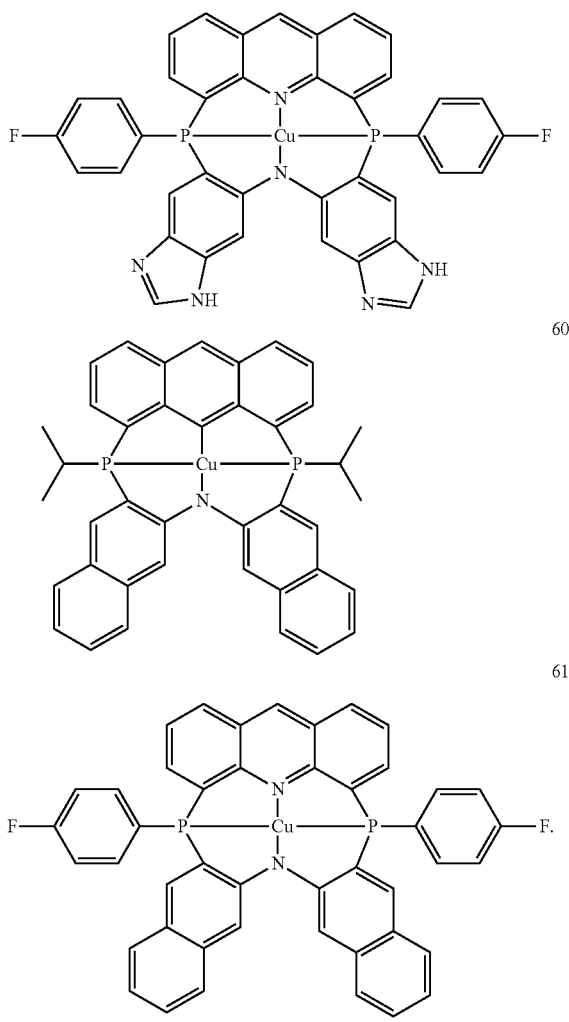

The organometallic complex may include copper as a core metal. Copper is a metal lighter (e.g., has a lower atomic mass) than iridium or platinum, and thus in comparison with phosphorescent emission of an iridium or platinum complex, a copper complex may emit not only phosphorescence, but also delayed fluorescence, thereby showing high emission efficiency. The delayed fluorescence refers to fluorescent emission upon activation of energy up-conversion from a triplet excited state to a singlet excited state. Due to the emission from the singlet excited state via the triplet excited state, the delayed fluorescence may generally have a long emission lifetime.

Since copper is smaller (e.g., has a smaller atomic radius) than iridium or platinum, copper may facilitate a ligand structure, and accordingly loss its emitting energy due to a structural change (e.g., it may improve its emitting energy due to the structural change). In Formulae 1-1 and 1-2, a ligand is linked to copper by using large-sized phosphorus (P). In addition, use of a rigid ligand, e.g., acridine, may stabilize its structure upon steric hindrance so that energy loss that is caused by a structural change may be prevented or reduced, thereby increasing emission efficiency.

The organometallic complex represented by Formulae 1-1 or 1-2 may be synthesized by a suitable organic synthetic method. A synthesis method of the organometallic compound may be understood in view of the description herein.

At least one selected from the organometallic complexes represented by Formulae 1-1 and 1-2 may be used between a pair of electrodes of an organic light-emitting device. For example, at least one organometallic complex may be included in the emission layer.

Accordingly, there is provided an organic light-emitting device including: a first electrode, a second electrode facing the first electrode, and an organic layer that is disposed between the first electrode and the second electrode and includes an emission layer, wherein the organic layer includes at least one of the organometallic complexes described herein.

The expression "(organic layer) includes at least one organometallic complex," as used herein, may include a case in which "(an organic layer) includes at least one of the organometallic compounds represented by Formula 1 or a case in which (an organic layer) includes two or more different organometallic compounds represented by Formula 1".

For example, the organic layer may include, as the organometallic complex, only Complex 1. In this regard, Complex 1 may exist in an emission layer of the organic light-emitting device. In some embodiments, the organic layer may include, as the organometallic complex, two or more complexes. In this regard, a plurality of the complexes may exist in an identical layer (for example, Complex 1 and Complex 2 may all exist in an emission layer).

The organic layer may further include, between the first electrode and the emission layer, at least one selected from a hole injection layer, a hole transport layer, a hole injection-transport layer having both hole injection and hole transport capabilities concurrently (e.g., at the same time), a buffer layer, and an electron blocking layer, and may also further include, between the emission layer and the second electrode, at least one selected from a hole blocking layer, an electron transport layer, and an electron injection layer.

The term "organic layer," as used herein, refers to a single layer and/or a plurality of layers disposed between the first electrode and the second electrode of an organic light-emitting device.

The organic layer may include the emission layer, which includes at least one of the organometallic complexes.

The organometallic complex included in the emission layer may serve as a phosphorescent dopant or a delayed fluorescent dopant, and the emission layer may further include a host. A type or kind of the host will be described further below.

The organic light-emitting device including the organometallic complex may emit green light, such green phosphorescence or green delayed fluorescence.

The accompanying drawing illustrates a schematic view of an organic light-emitting device 10 according to an embodiment. Hereinafter, the structure of an organic light-emitting device according to an embodiment and a method of manufacturing an organic light-emitting device according to an embodiment will be described in connection with the accompanying drawing.

As a substrate 11, any suitable substrate available in the art for an organic light-emitting device may be used. For example, the substrate 11 may be a glass substrate or a transparent plastic substrate, each with excellent mechanical strength, thermal stability, transparency, surface smoothness, ease of handling, and water-resistance.

A first electrode 13 may be formed by depositing or sputtering a material for forming the first electrode on the substrate 11. When the first electrode 13 is an anode, the material for forming the first electrode may be selected from materials with a high work function to facilitate hole injection. The first electrode 13 may be a reflective electrode or a transmissive electrode. The material for forming the first electrode may be a transparent and highly conductive material, and examples of such a material are indium tin oxide (ITO), indium zinc oxide (IZO), tin oxide ($SnO_2$), and zinc oxide (ZnO). When the first electrode 13 is a reflective electrode, as a material for forming the first electrode, at least one selected from magnesium (Mg), aluminum (Al), aluminum-lithium (Al—Li), calcium (Ca), magnesium-indium (Mg—In), magnesium-silver (Mg—Ag) may be used.

The first electrode 13 may have a single-layer structure, or a multi-layer structure including two or more layers. For example, the first electrode 13 may have a three-layered structure of ITO/Ag/ITO, but is not limited thereto.

An organic layer 15 may be disposed on the first electrode 13.

The organic layer 15 may further include, in addition to the emission layer, at least one selected from a hole injection layer (HIL), a hole transport layer (HTL), a hole injection-transport layer, a buffer layer, an electron transport layer, and an electron injection layer.

An HIL may be formed on the first electrode 13 by using various suitable methods, such as vacuum deposition, spin coating, casting, and a Langmuir-Blodgett (LB) method.

When an HIL is formed by vacuum deposition, the vacuum deposition may be performed at a temperature of a deposition temperature of about 100 to about 500° C., at a vacuum degree of about $10^{-8}$ to about $10^{-3}$ torr, and at a deposition rate of about 0.01 to about 100 Å/sec, in consideration of a compound for an HIL to be deposited, a structure of an HIL to be deposited, and thermal characteristics thereof, but the embodiment is not limited thereto.

When an HIL is formed by spin coating, the spin coating may be performed at a coating rate of about 2,000 rpm to about 5,000 rpm and at a temperature of about 80° C. to 200° C. to allow heat treatment to evaporate a solvent after coating, in consideration of a compound for an HIL to be deposited, a structure of an HIL to be deposited, and thermal characteristics thereof, but the embodiment is not limited thereto.

Any suitable hole injecting material available in the art may be used for the hole injection, and examples of such a material include N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), or polyaniline/poly(4-styrenesulfonate) (PANI/PSS), but the embodiment is not limited thereto:

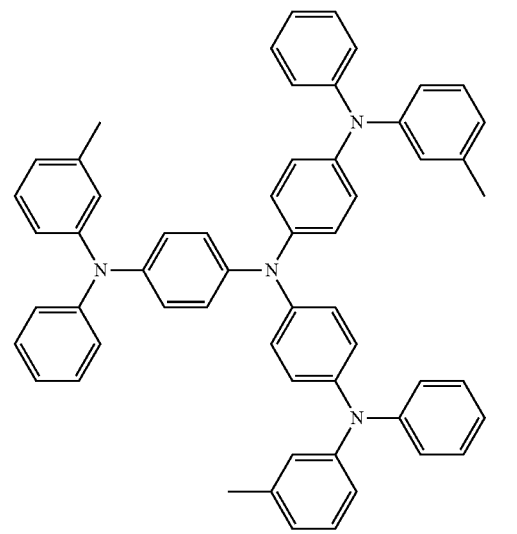

m-MTDATA

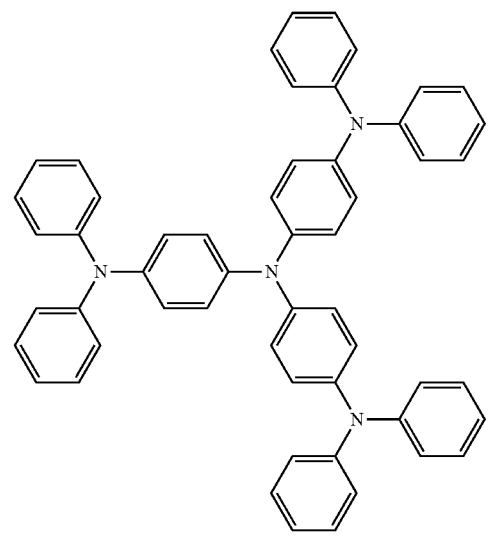

TDATA

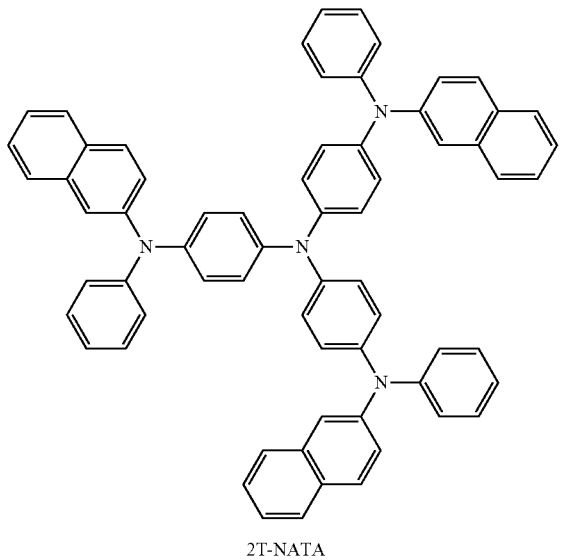

2T-NATA

-continued

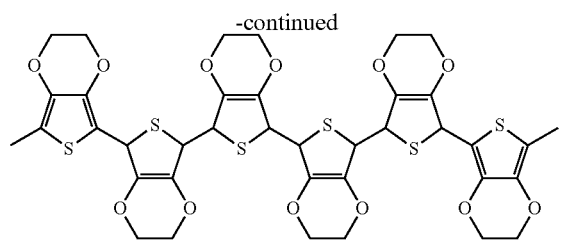

PEDOT/PSS

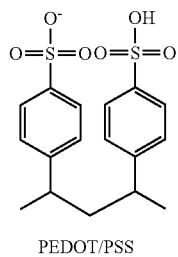

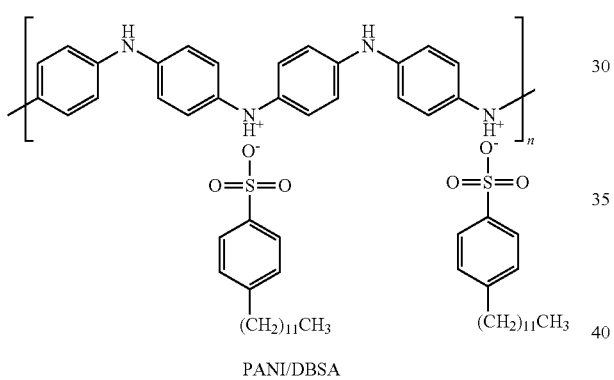

PANI/DBSA

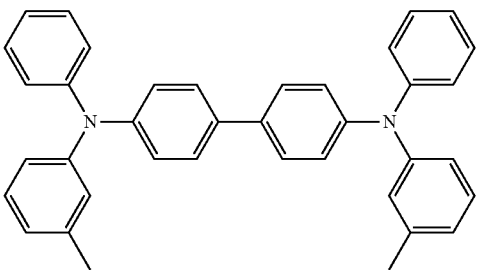

TPD

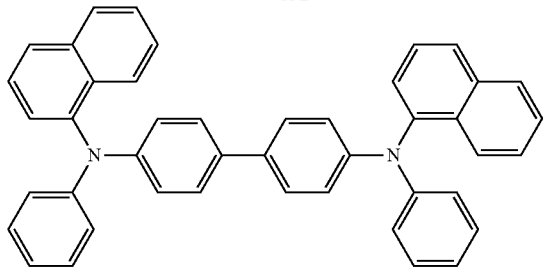

NPB

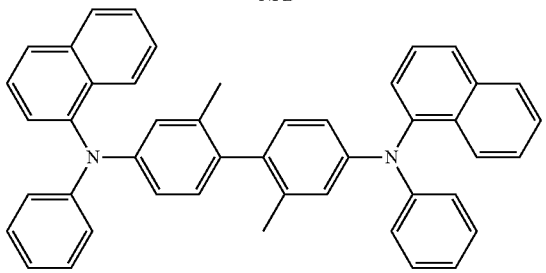

α-NPD

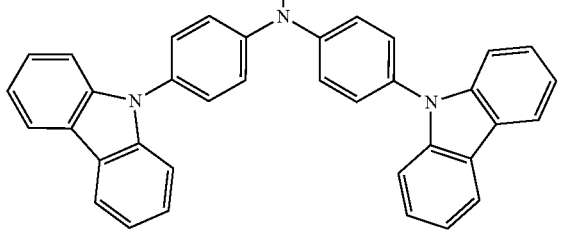

TCTA

A thickness of the HIL may be in a range of about 100 Å to about 10,000 Å, e.g., about 100 Å to about 1,000 Å. When the thickness of the HIL is within these ranges, suitable or satisfactory hole injecting characteristics may be obtained without a substantial increase in driving voltage.

Subsequently, an HTL may be formed on the HIL by using various suitable methods, such as vacuum deposition, spin coating, casting, and a LB method. When an HTL is formed by vacuum deposition and spin coating, the deposition and coating conditions may be determined in consideration of a compound for an HTL to be deposited by referring to the deposition and coating conditions for forming the HIL.

Any suitable hole transporting material available in the art may be used for the hole transport, and examples of such a material are a carbazole derivative, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine) (TCTA), or N,N'-di(1-naphthyl)-N,N'-diphenylbenzidine (NPB), but the embodiment is not limited thereto:

A thickness of the HTL may be in a range of about 50 Å to about 2,000 Å, e.g., about 100 Å to about 1,500 Å. When the thickness of the HTL is within these ranges, suitable or satisfactory hole transporting characteristics may be obtained without a substantial increase in driving voltage.

The hole injection-transport layer may include at least one selected from the material for forming the HIL and the material for forming the HTL, and a thickness of the hole injection-transport may be in a range of about 500 Å to about 10,000 Å, e.g., about 100 Å to about 1,000 Å. When the thickness of the hole injection-transport layer is within these ranges, suitable or satisfactory hole injection-transporting characteristics may be obtained without a substantial increase in driving voltage.

In addition, at least one layer of the HIL, the HTL, and the hole injection-transport layer may include at least one selected from a compound represented by Formula 100 and a compound represented by Formula 101:

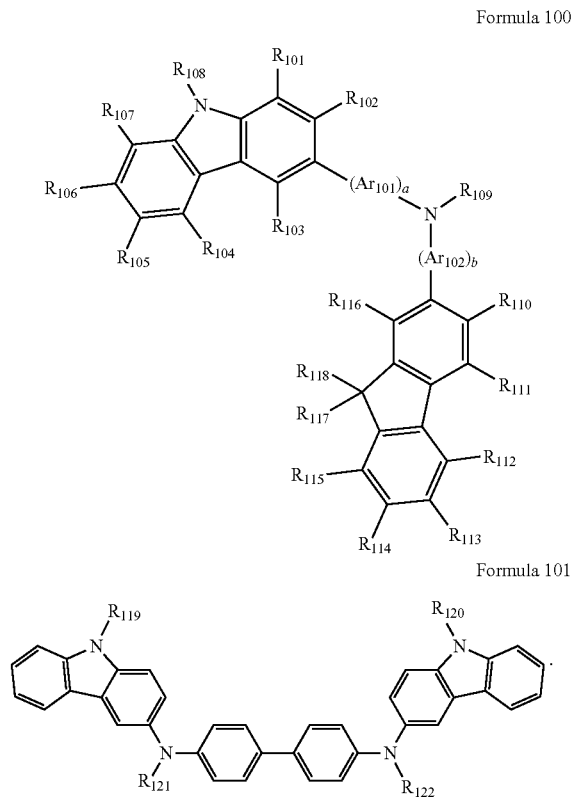

Formula 100

Formula 101

In Formula 100, $Ar_{101}$ and $Ar_{102}$ may each be independently a substituted or unsubstituted $C_6$-$C_{40}$ arylene group. For example, $Ar_{101}$ and $Ar_{102}$ may each be independently a phenylene group, a pentalenylene group, an indenylene group, a naphthylene group, an azulenylene group, a heptalenylene group, a substituted or unsubstituted acenaphthylene group, a fluorenylene group, a phenalenylene group, a phenanthrenylene group, an anthrylene group, a fluoranthenylene group, a triphenylenylene group, a pyrenylene group, a chrysenylenylene group, a naphthacenylene group, a picenylene group, a perylenylene group, and a pentacenylene group; and
a phenylene group, a pentalenylene group, an indenylene group, a naphthylene group, an azulenylene group, a heptalenylene group, a substituted or unsubstituted acenaphthylene group, a fluorenylene group, a phenalenylene group, a phenanthrenylene group, an anthrylene group, a fluoranthenylene group, a triphenylenylene group, a pyrenylene group, a chrysenylenylene group, a naphthacenylene group, a picenylene group, a perylenylene group, and a pentacenylene group, each substituted with a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{40}$ alkyl group, a $C_2$-$C_{40}$ alkenyl group, a $C_2$-$C_{40}$ alkynyl group, a $C_1$-$C_{40}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{40}$ aryl group, a $C_6$-$C_{40}$ aryloxy group, a $C_6$-$C_{40}$ arylthio group, and a $C_1$-$C_{40}$ heteroaryl group.

In Formula 100, a and b may each be independently an integer from 0 to 5, or 0, 1, or 2. For example, a may be 1 and b may be 0, but the embodiment is not limited thereto.

In Formulae 100 and 101, $R_{101}$ to $R_{122}$ may each be independently a hydrogen, a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{40}$ alkyl group, a substituted or unsubstituted $C_2$-$C_{40}$ alkenyl group, a substituted or unsubstituted $C_2$-$C_{40}$ alkynyl group, a substituted or unsubstituted $C_1$-$C_{40}$ alkoxy group, a substituted or unsubstituted $C_3$-$C_{40}$ cycloalkyl group, a substituted or unsubstituted $C_6$-$C_{40}$ aryl group, a substituted or unsubstituted $C_6$-$C_{40}$ aryloxy group, or a substituted or unsubstituted $C_6$-$C_{40}$ arylthio group.

For example, $R_{101}$ to $R_{108}$ and $R_{110}$ to $R_{122}$ in Formulae 100 and 101 may each be independently one of a hydrogen, a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, pentyl group, and a hexyl group), a $C_1$-$C_{10}$ alkoxy group (e.g., a methoxy group, an ethoxy group, a propoxy group, butoxy group, and a pentoxy group), a phenyl group, a naphthyl group, an anthryl group, a fluorenyl group, a pyrenyl group; and a $C_1$-$C_{10}$ alkyl group and a $C_1$-$C_{10}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof, a phenyl group, a naphthyl group, an anthryl group, a fluorenyl group, and a pyrenyl group, but the embodiment is not limited thereto.

In Formula 100, $R_{109}$ may be one of a phenyl group, a naphthyl group, an anthryl group, a biphenyl group, and a pyridyl group; and a phenyl group, a naphthyl group, an anthryl group, a biphenyl group, and a pyridyl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

According to an embodiment, the compound represented by Formula 100 may be represented by Formula 100A below, but the embodiment is not limited thereto:

Formula 100A
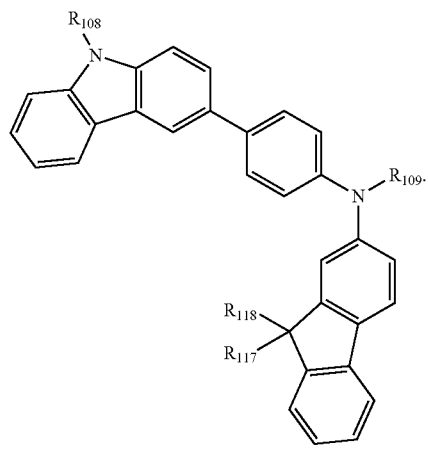
Descriptions of $R_{108}$, $R_{109}$, $R_{117}$ and $R_{118}$ in Formula 100A may be understood by referring to the description provided herein.
For example, at least one layer of the HIL, the HTL, and the hole injection-transport layer may include at least one selected from Compounds 102 to 121 below, but the embodiment is not limited thereto:
102
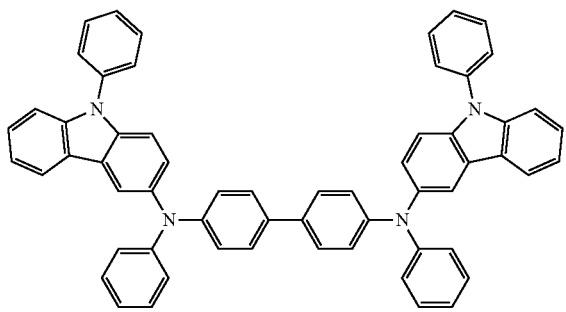
103
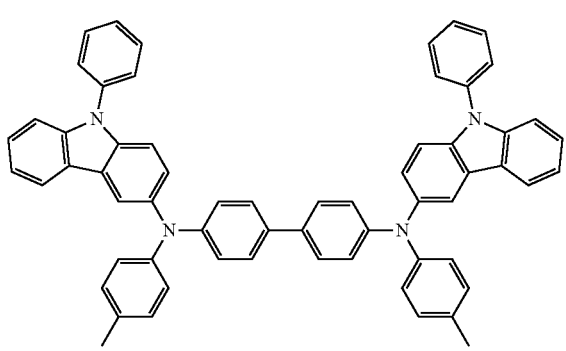
104
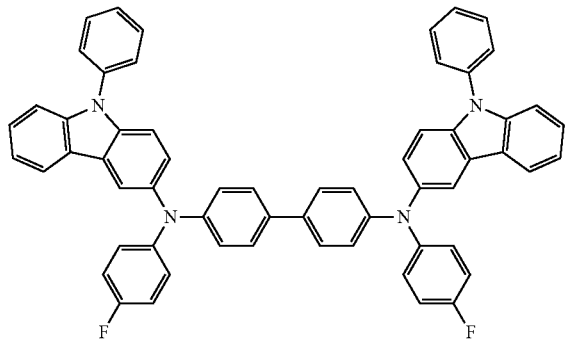
105
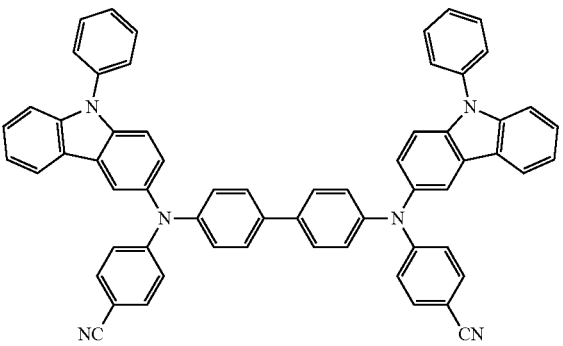
106
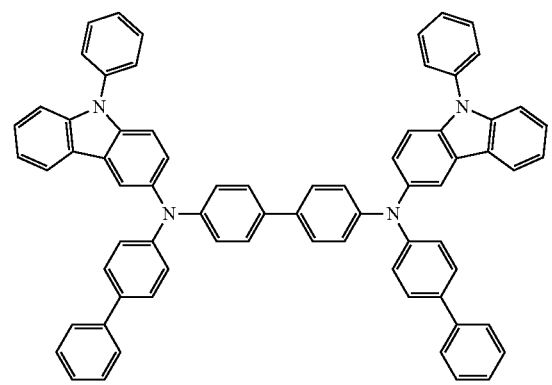
107

108
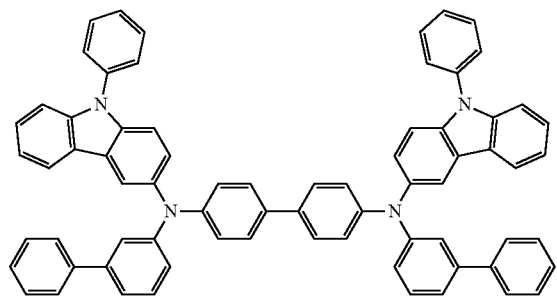
109
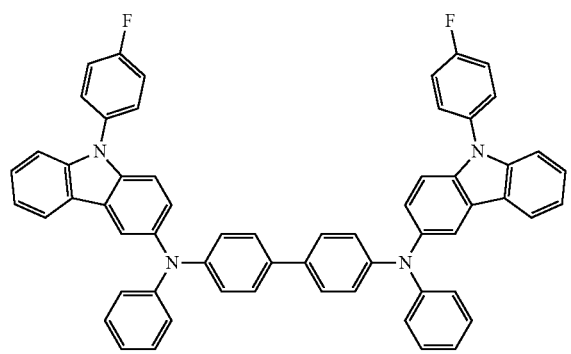
110
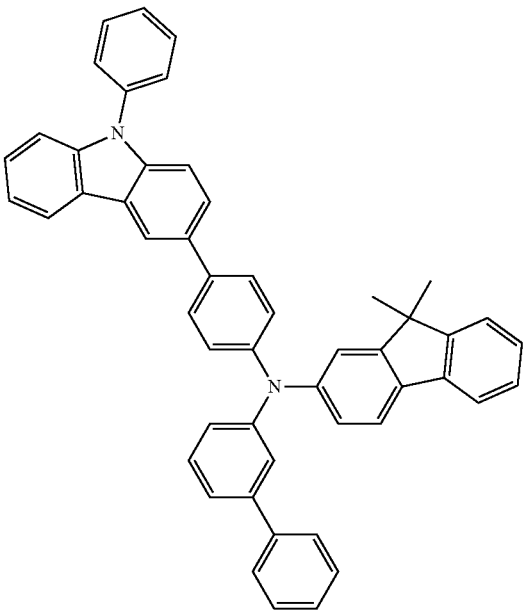
111
112
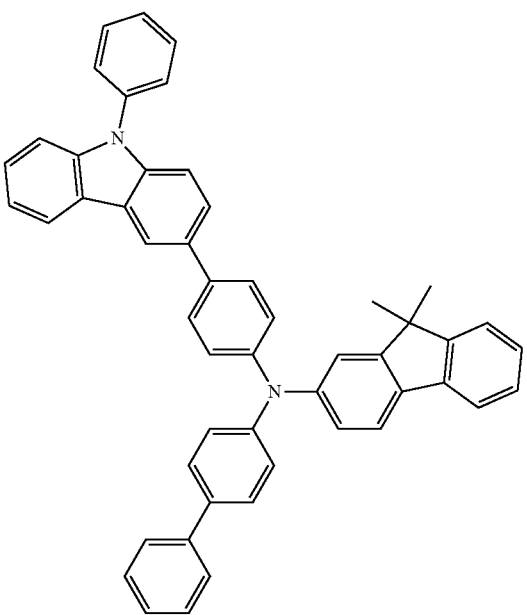

113
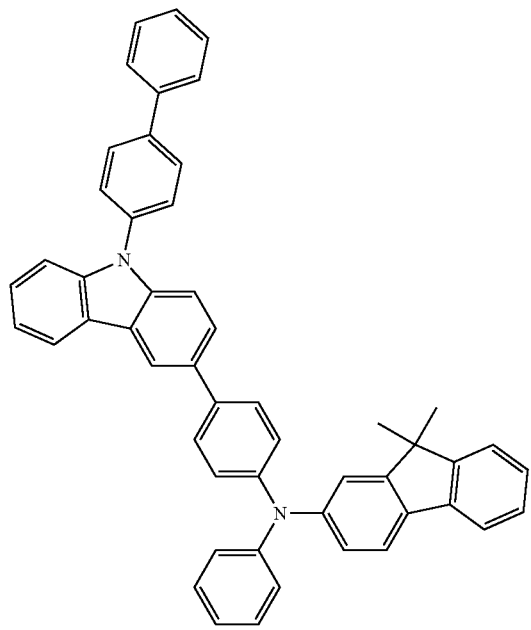
114
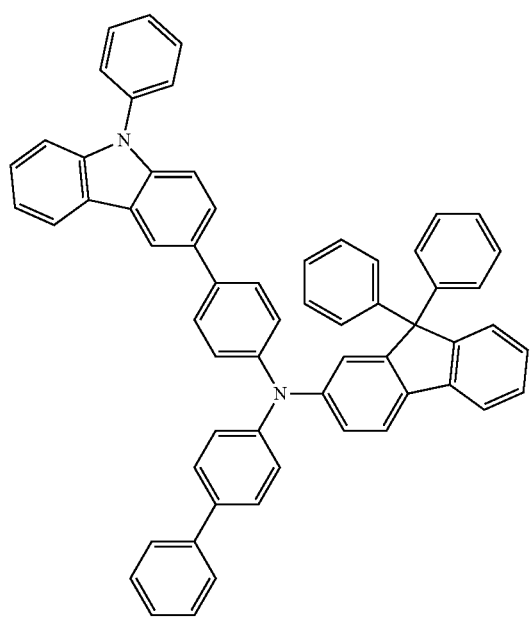
115
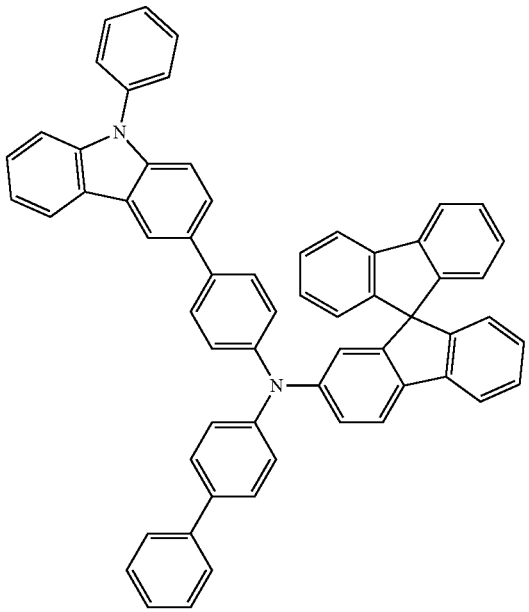
116
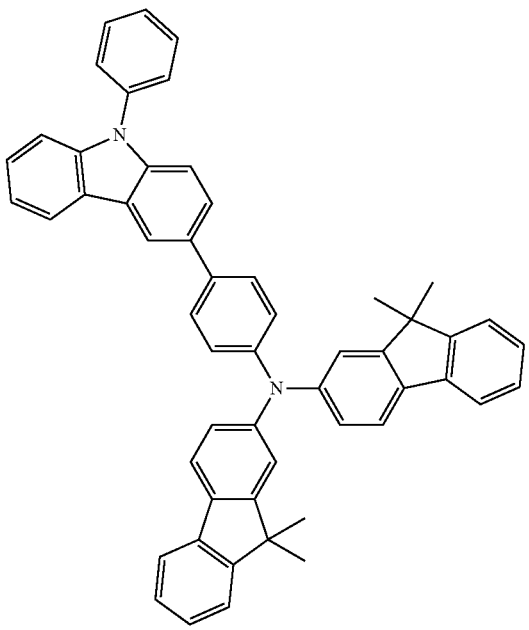

117

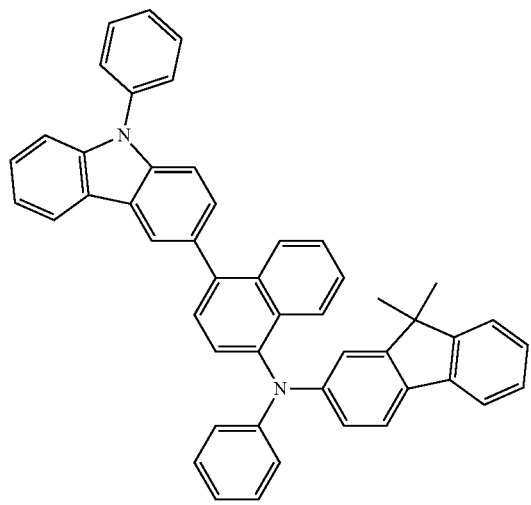

118

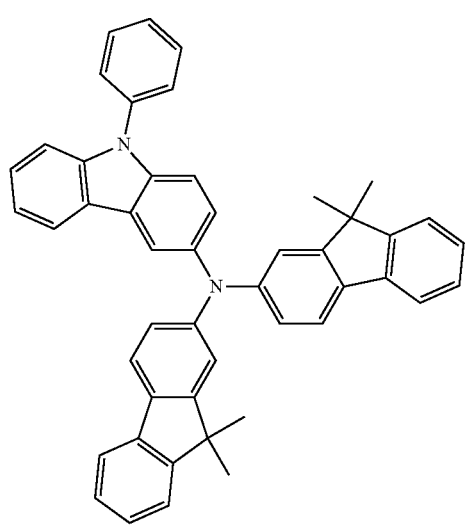

119

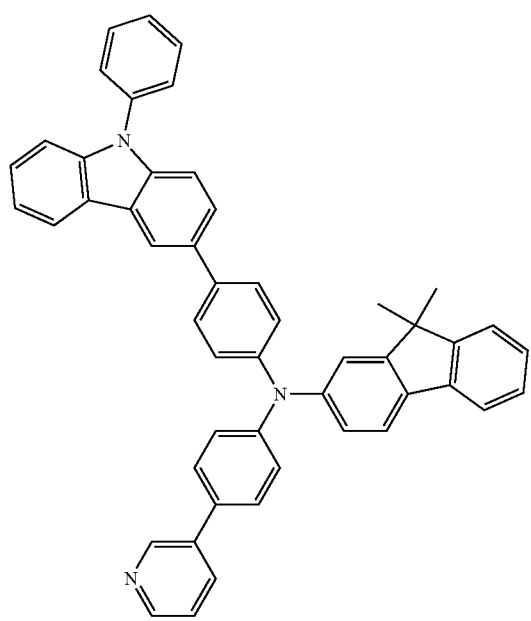

120

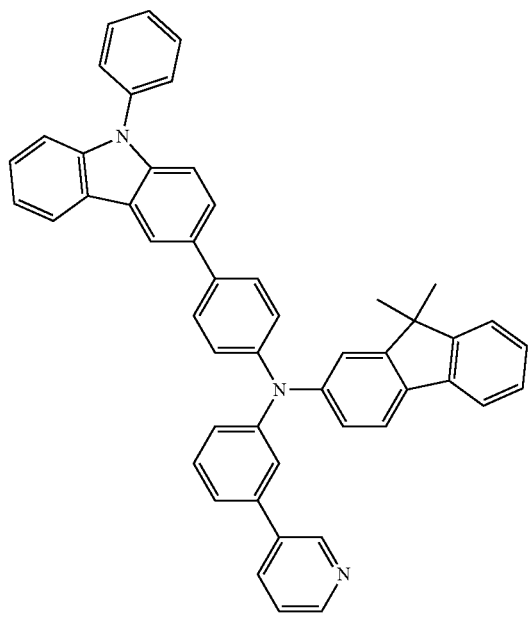

121

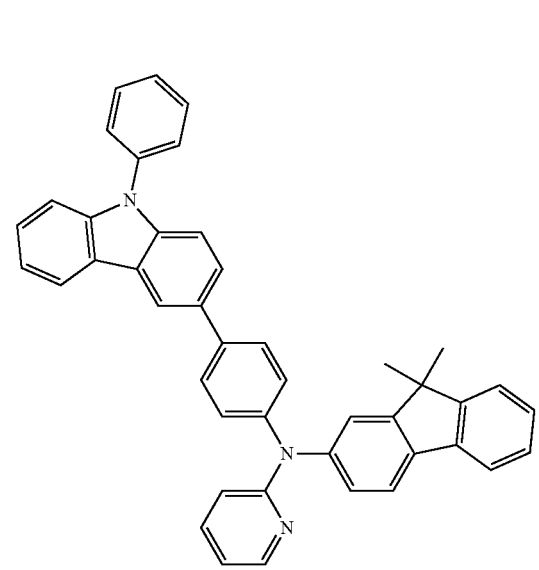

At least one selected from the HIL, the HTL, and the hole injection-transport layer may further include, in addition to the hole injection material, the hole transport material, and/or the material having both hole injection and hole transport capabilities concurrently (e.g., at the same time) as described above, a charge generation material for the improvement of conductive properties.

The charge-generation material may be, for example, a p-dopant. Non-limiting examples of the p-dopant may include a quinone derivative, such as tetracyanoquinonedimethane (TCNQ) and 2,3,5,6-tetrafluoro-tetracyano-1,4-benzoquinonedimethane (F4-TCNQ), a metal oxide, such as a tungsten oxide or a molybdenum oxide, and 1,4,5,8,9,11-hexaazatriphenylene-hexacarbonitrile (Compound HATCN), but the embodiment is not limited thereto:

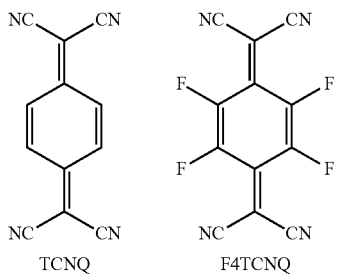

TCNQ    F4TCNQ

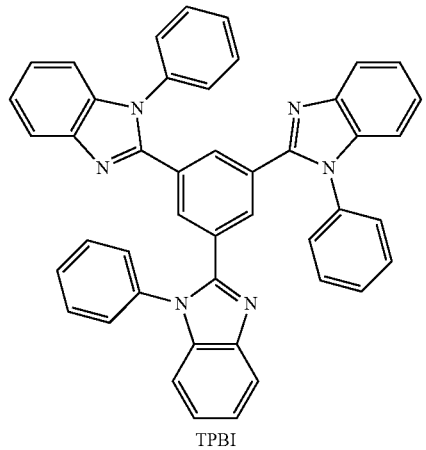

TPBI

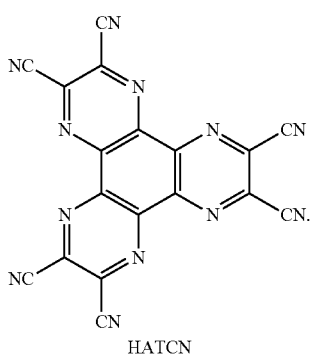

HATCN

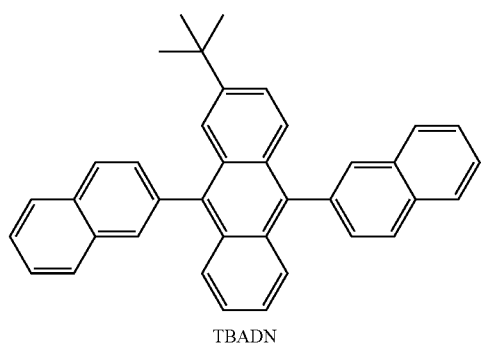

TBADN

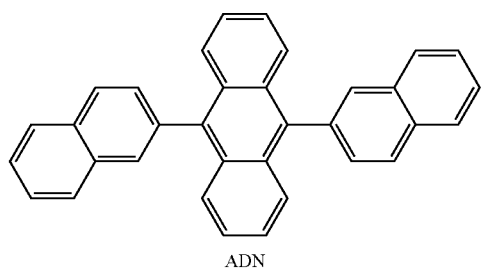

ADN

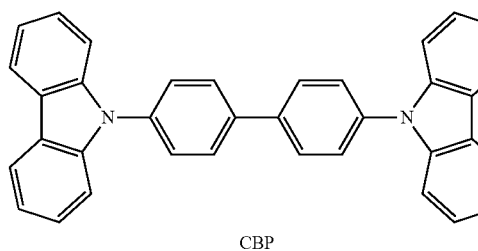

CBP

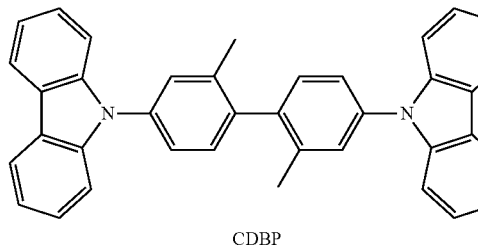

CDBP

When the HIL, the HTL, or the hole injection-transport layer further includes the charge-generation material, the charge-generation material may be homogeneously or unhomogeneously dispersed in the layers above.

Subsequently, an emission layer (EML) may be formed on the HIL or the hole injection-transport layer by using various suitable methods, such as vacuum deposition, spin coating, casting, and a LB method. When the EML is formed by vacuum deposition and spin coating, the deposition and coating conditions may be determined in consideration of a compound for an EML to be deposited by referring to the deposition and coating conditions for forming the HIL.

The EML may include at least one of the organometallic complexes.

The organometallic complex included in the EML may serve as a dopant (e.g., a dopant for green phosphorescence). Here, the EML may further include; in addition to the organometallic complex, a host.

The host may be at least one selected from suitable hosts available in the art. For example, the host may be Alq$_3$, 4,4'-N,N'-dicarbazole-biphenyl (CBP), 4,4'-bis(9-carbazolyl)-2,2'-dimethylbiphenyl (CDBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl)anthracene (3-tert-butyl-9,10-di), N,N'-dicarbazolyl-3,5-benzene (mCP), or 1,3-bis[(4-tert-butylphenyl)-1,3,4-oxadiazolephenylene] (OXD-7), but the embodiment is not limited thereto.

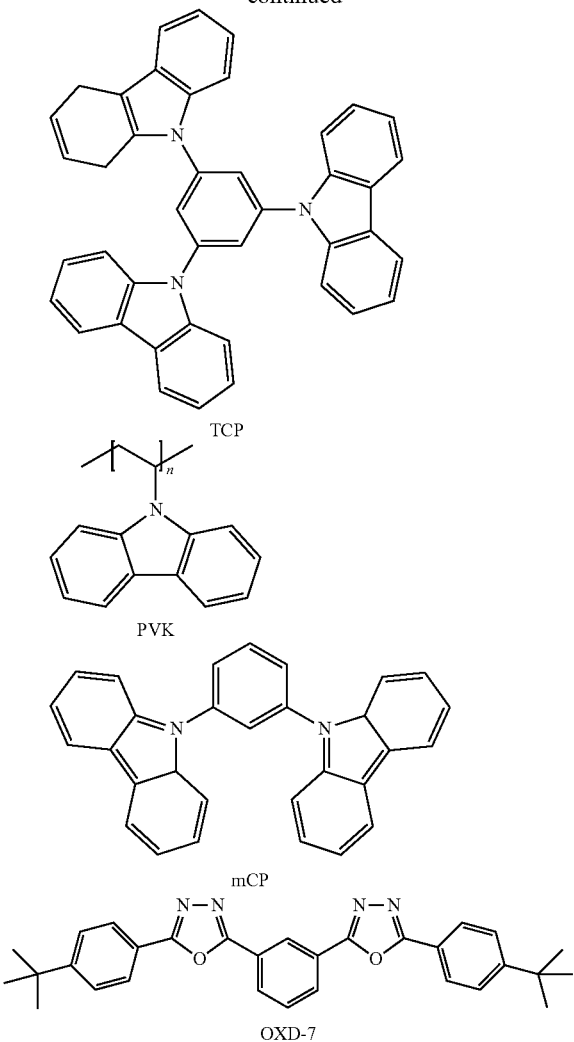

TCP

PVK mCP

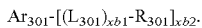

OXD-7

In some embodiments, the host may include a compound represented by Formula 301 below:

$$Ar_{301}\text{-}[(L_{301})_{xb1}\text{-}R_{301}]_{xb2}.$$  Formula 301

In Formula 301, $Ar_{301}$ may be selected from:

a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene and an indenoanthracene, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent $C_2$-$C_{60}$ non-aromatic condensed polycyclic group, and —Si($Q_{301}$)($Q_{302}$)($Q_{303}$) (wherein $Q_{301}$ to $Q_{303}$ are each be independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group), $L_{301}$ is defined the same as $Ar_{101}$ provided herein, $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3, and xb2 may be selected from 1, 2, 3, and 4.

For example, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but the embodiment is not limited thereto.

For example, the host may include a compound represented by Formula 301A below.

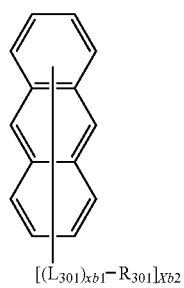

Formula 301A

Descriptions of substituents represented by Formula 301A may be understood by referring to the descriptions provided herein.

The compound represented by Formula 301 may include at least one selected from Compounds H1 to H42 below, but the embodiment is not limited thereto:

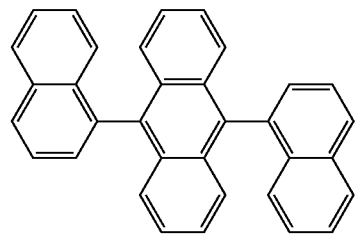

H1

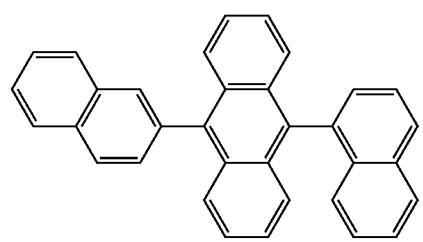

H2

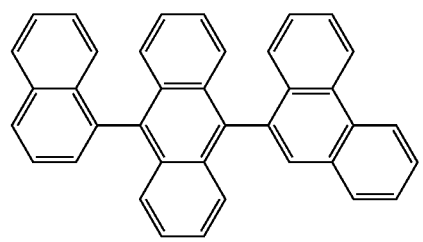

H3

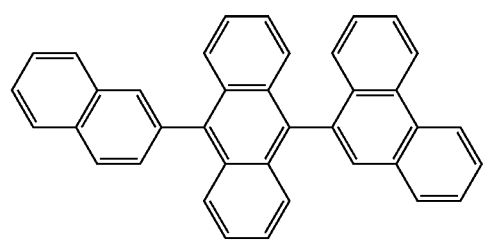

H4

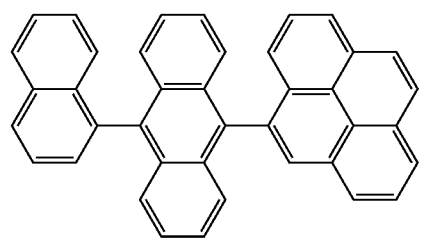

H5

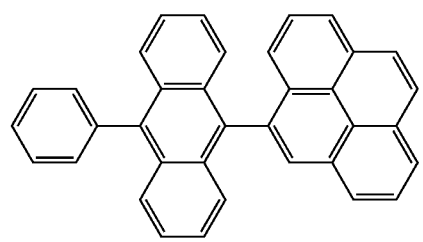

H6

H7
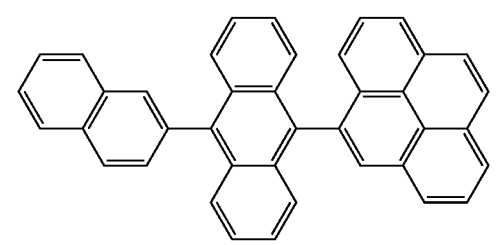
H8
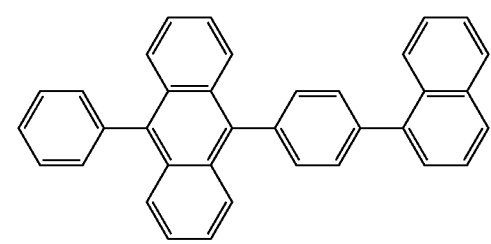
H9
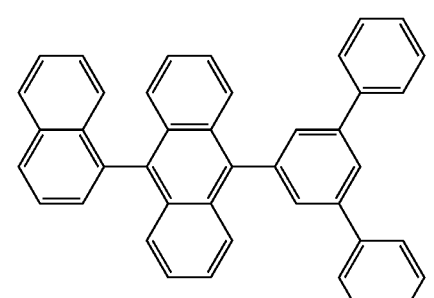
H10
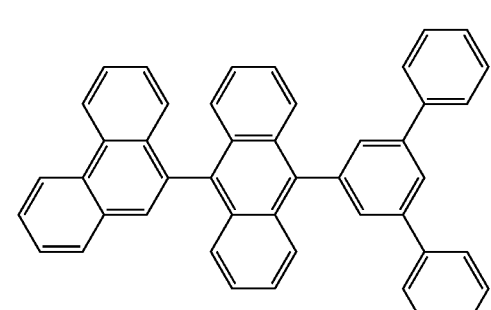
H11
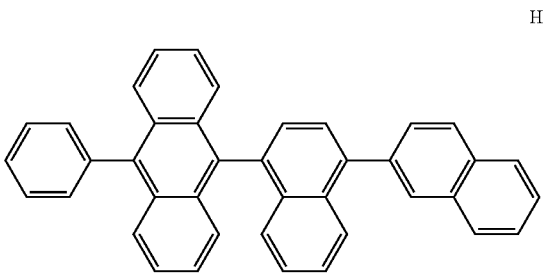
H12
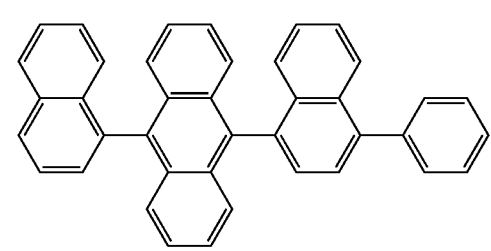
H13
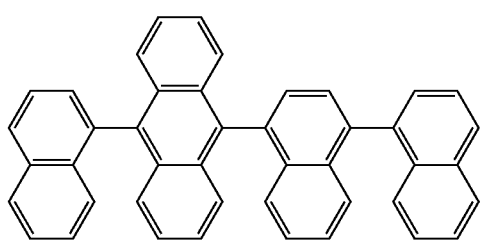
H14
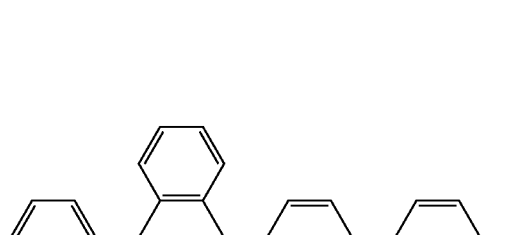
H15
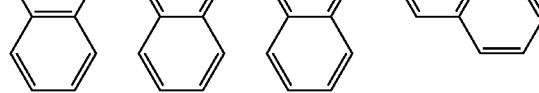
H16
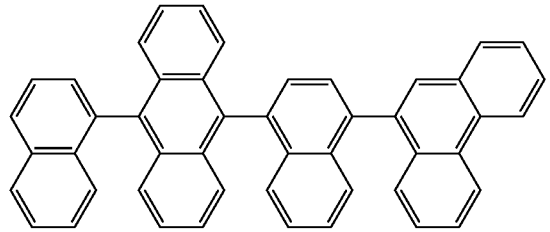
H17
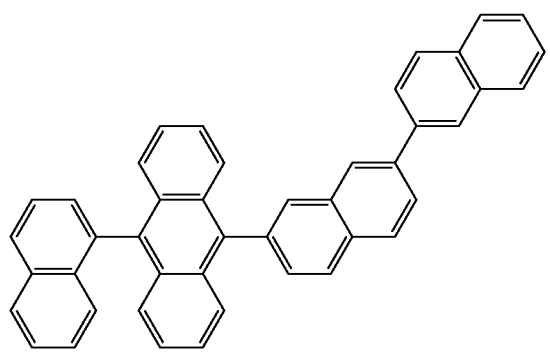

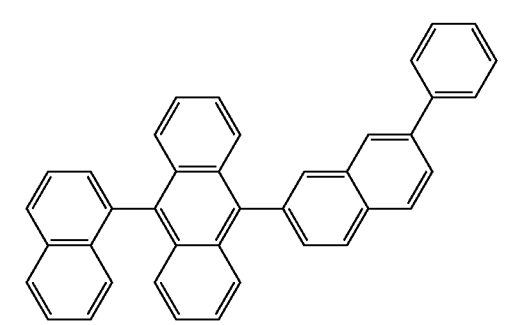
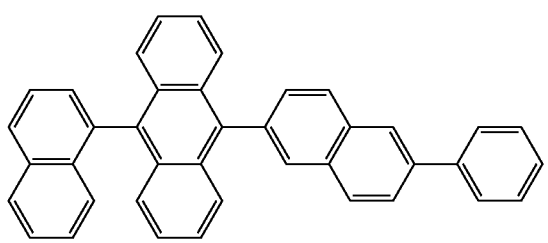
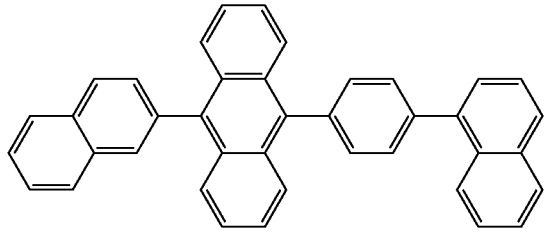

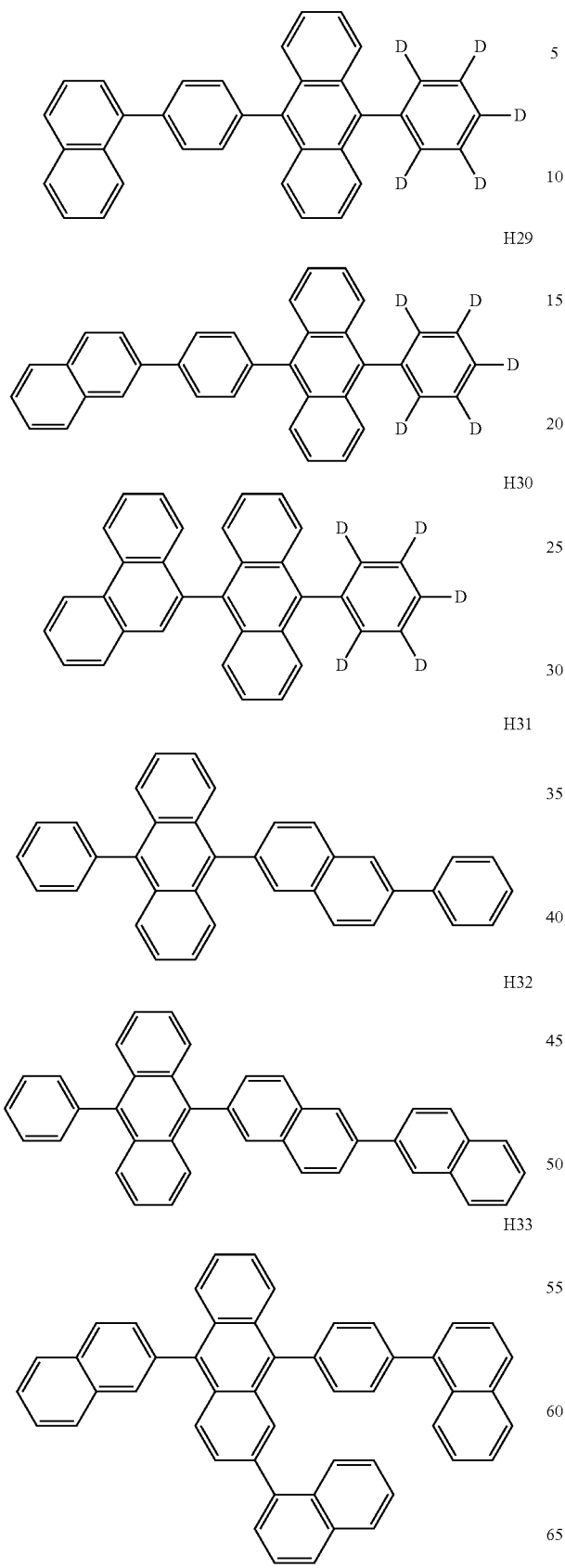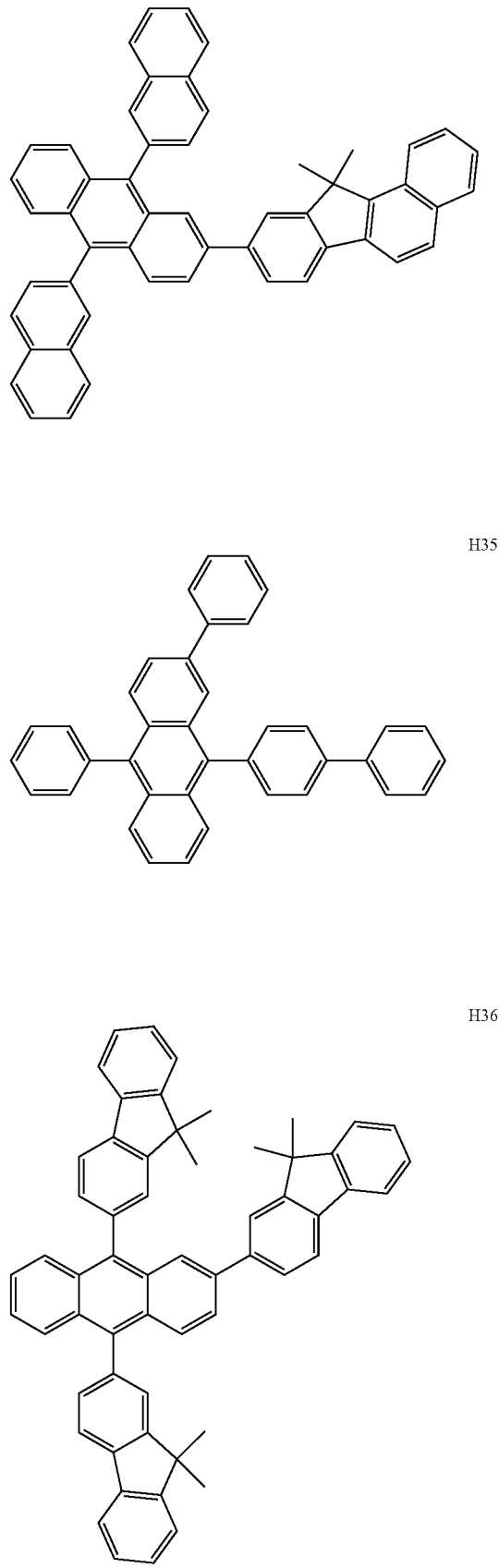

H37
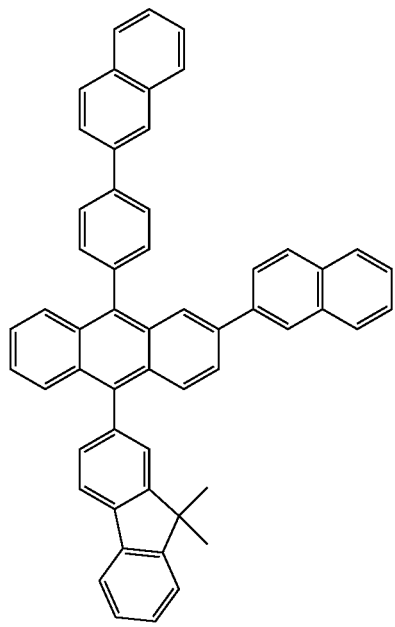
H38
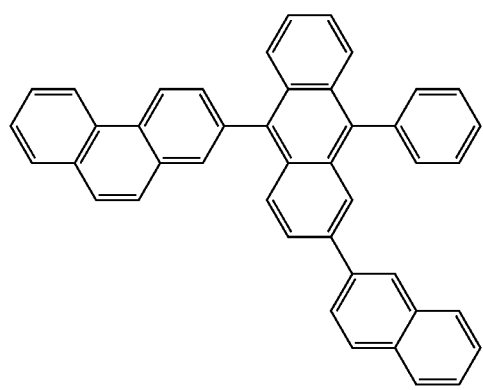
H39
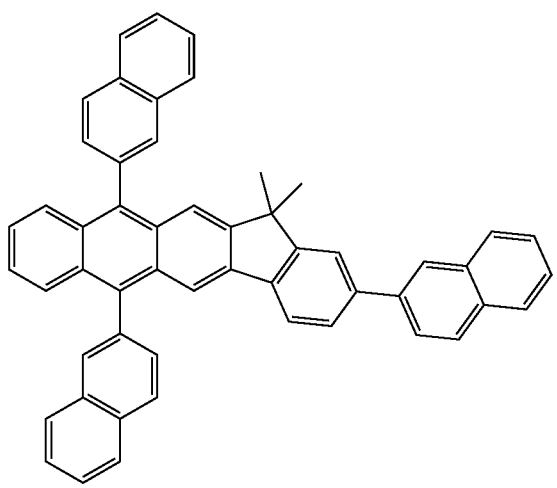
H40
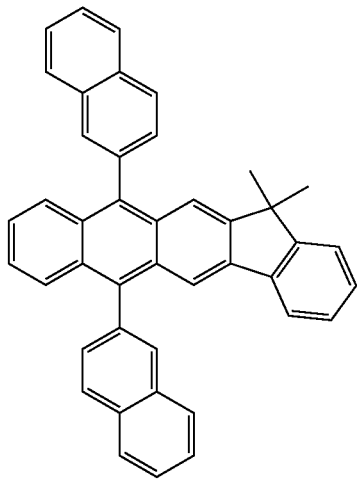
H41
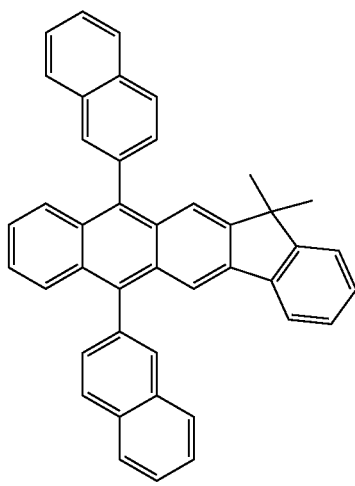
H42
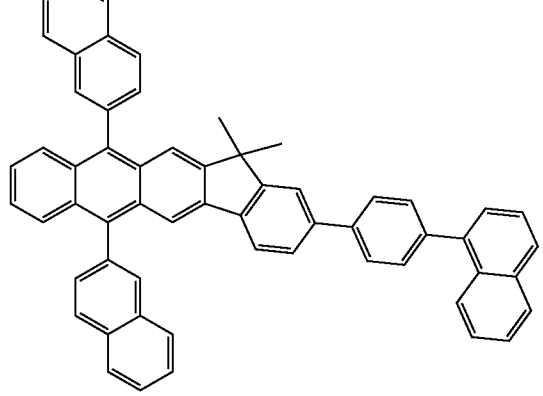
In some embodiments, the host may include at least one selected from Compounds H43 to H49 below, but the embodiment is not limited thereto:

H43 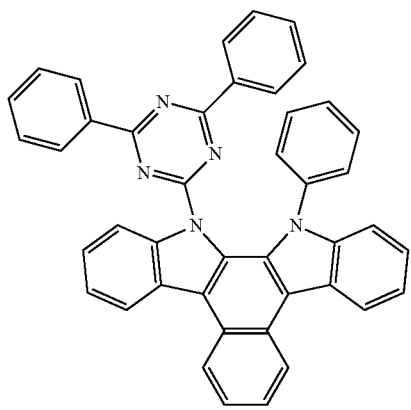
H44 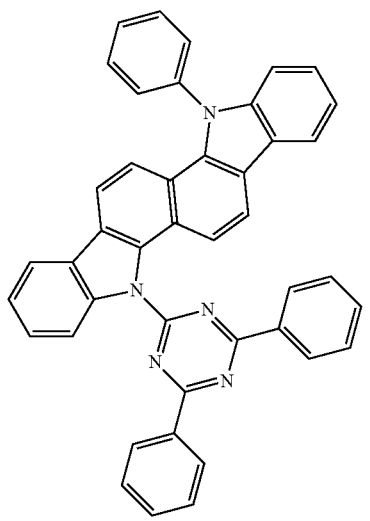
H45 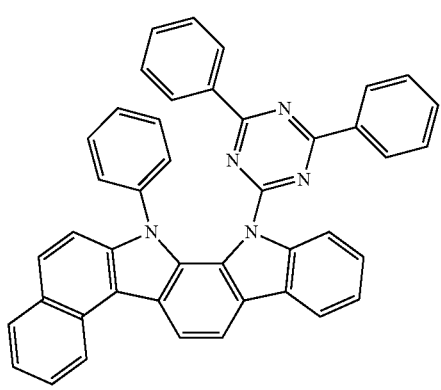
H46 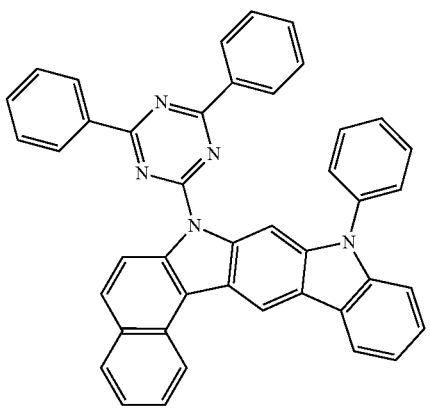
H47 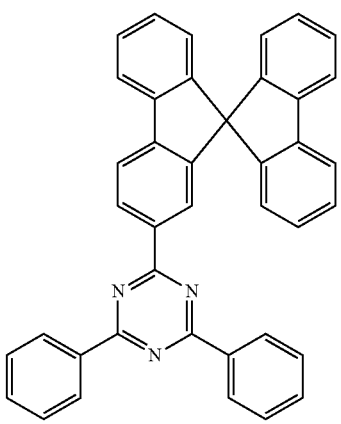
H48 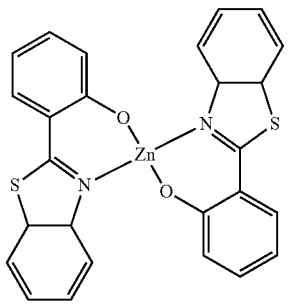
H49 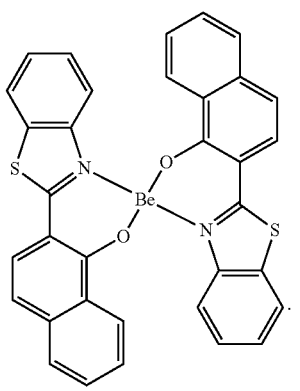
In some embodiments, the host may include a carbazole-based compound represented by Formula 302 below:

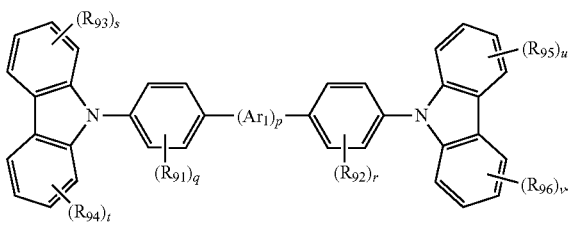

Formula 302

In Formula 302, $Ar_1$ may be a substituted or unsubstituted $C_1$-$C_{60}$ alkylene group, a substituted or unsubstituted $C_2$-$C_{60}$ alkenylene group, —C(=O)—, —N($R_{100}$)— (wherein $R_{100}$ is a substituted or unsubstituted $C_6$-$C_{60}$ aryl group or a substituted or unsubstituted $C_2$-$C_{60}$ heteroaryl group), a substituted or unsubstituted $C_6$-$C_{60}$ arylene group, or a substituted or unsubstituted $C_2$-$C_{60}$ heteroarylene group, p may be an integer of 0 to 10, $R_{91}$ to $R_{96}$ may each be independently selected from a hydrogen, a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_1$-$C_{10}$ heterocycloalkyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_1$-$C_{60}$ heteroaryl group, two neighboring substituents of $R_{91}$ to $R_{96}$ may be linked to each other to optionally form a substituted or unsubstituted $C_4$-$C_{20}$ alicyclic ring, a substituted or unsubstituted $C_1$-$C_{20}$ hetero alicyclic group, a substituted or unsubstituted $C_6$-$C_{20}$ aromatic ring, or a substituted or unsubstituted $C_1$-$C_{20}$ heteroaromatic ring, and q, r, s, t, u, and v may each be independently an integer of 1 to 4.

In Formula 302, $Ar_1$ may be a $C_1$-$C_5$ alkylene group, a $C_2$-$C_5$ alkenylene group, —C(=O)—, or —N($R_{100}$)—. Here, $R_{100}$ may be at least one selected from a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group, each substituted with at least one selected from a deuterium, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In Formula 302, $R_{91}$ to $R_{96}$ may each be independently selected from:

a hydrogen, a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from a deuterium, a halogen atom, a hydroxyl group, a cyano group, a nitro group, and an amino group.

The carbazole-based compound may include one of compounds below, but the embodiment is not limited thereto:

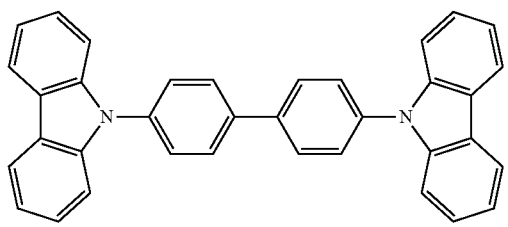

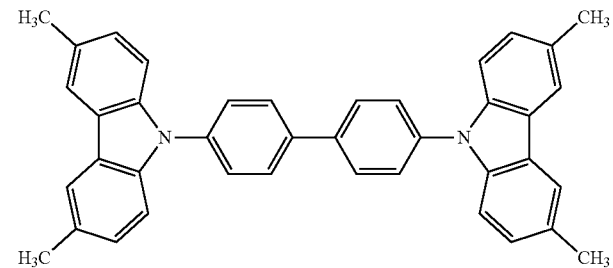

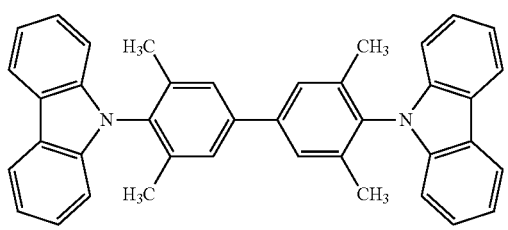

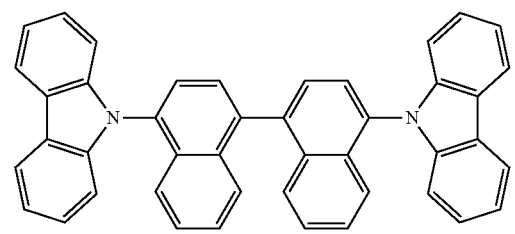

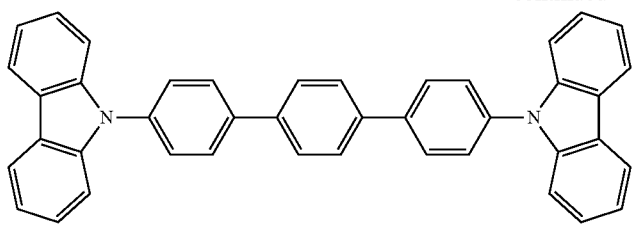
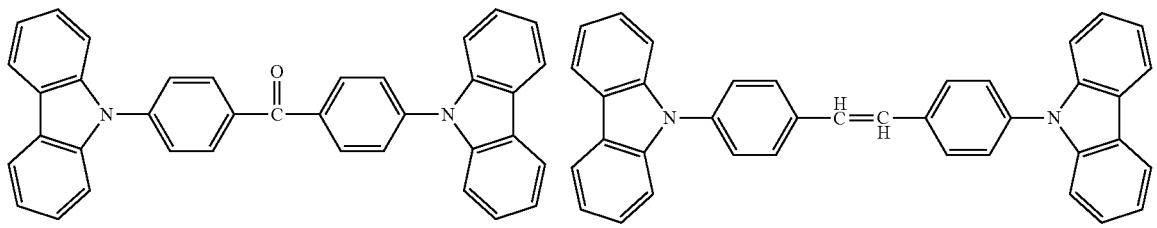
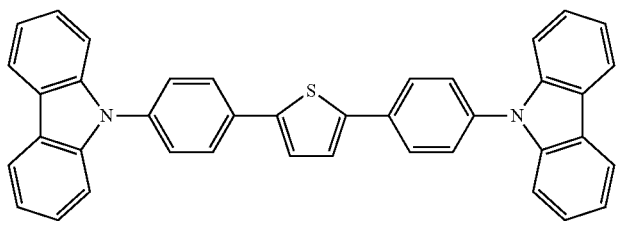
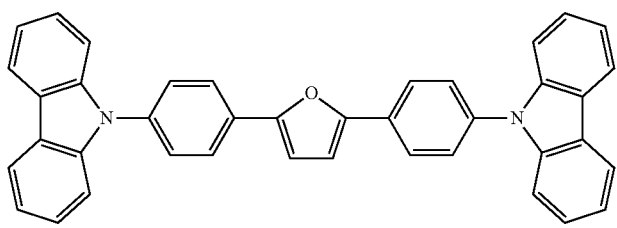
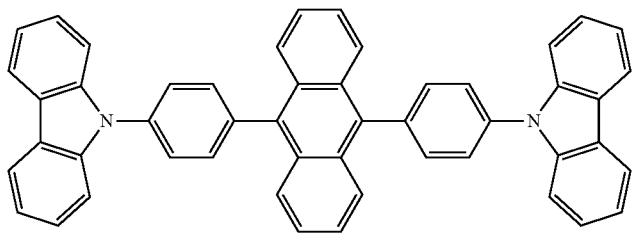
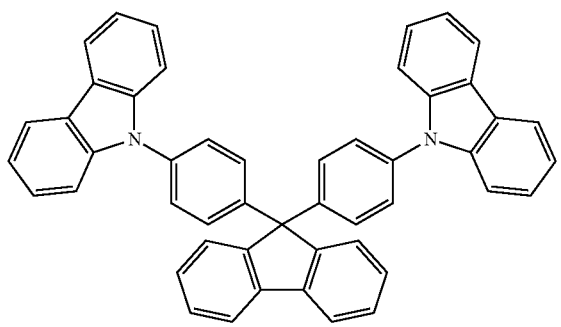
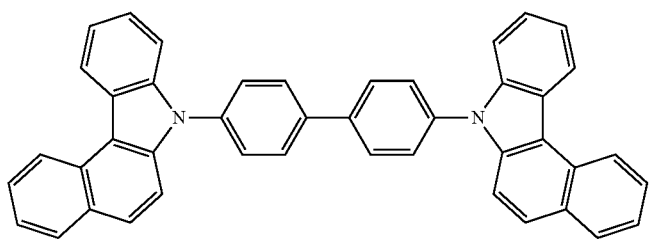

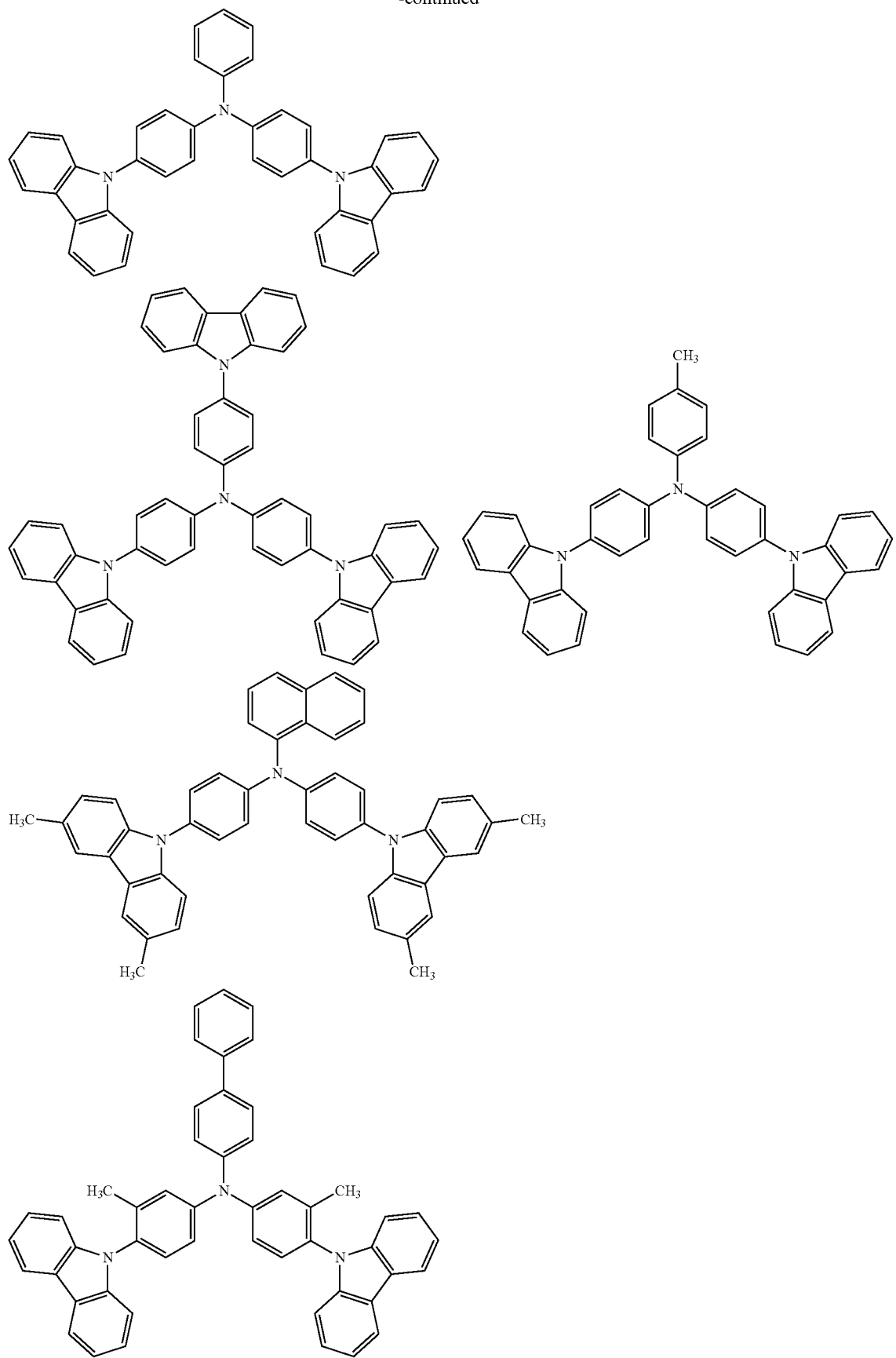

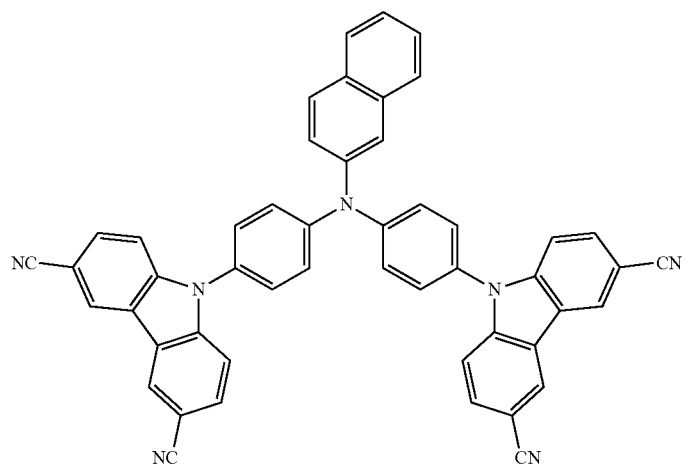
19

-continued
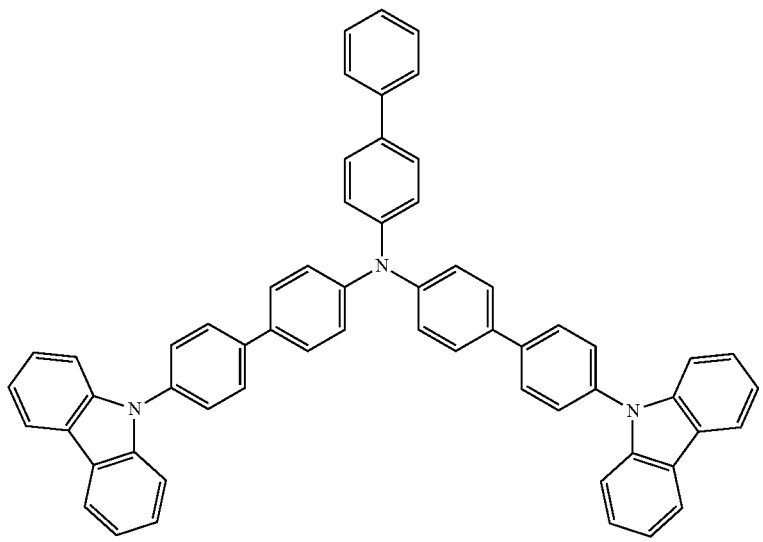
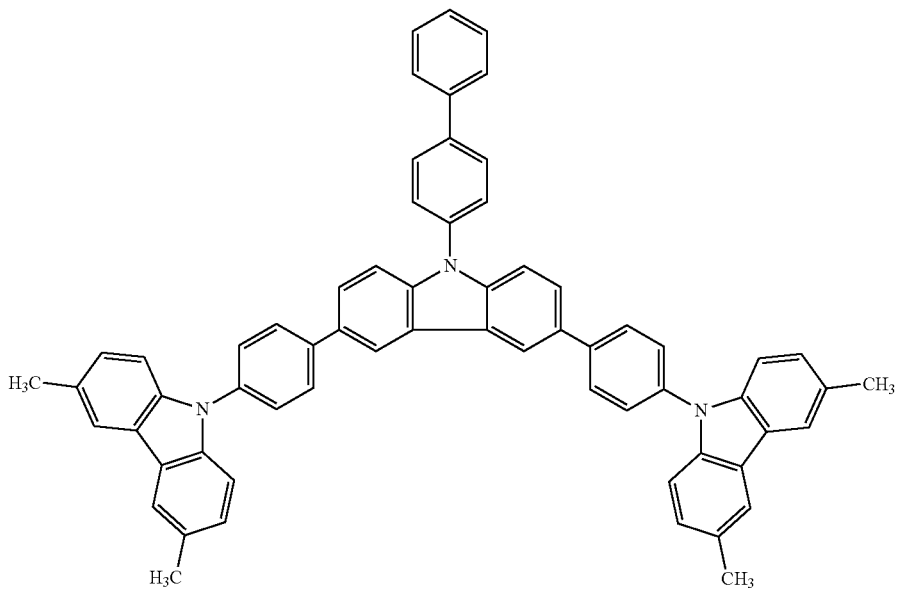
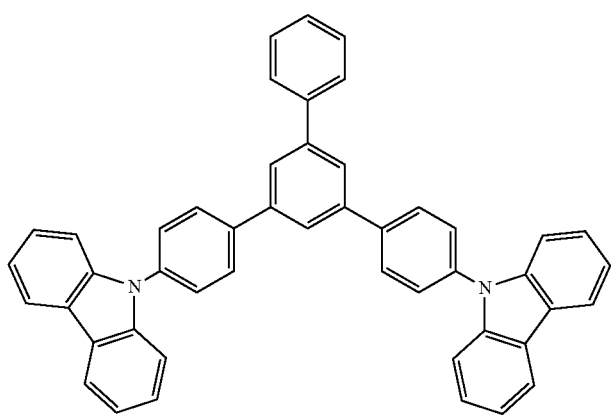

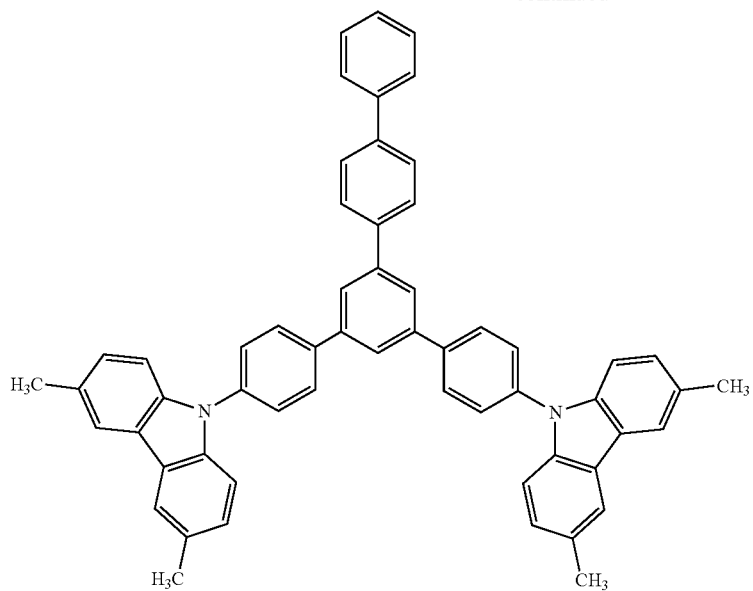
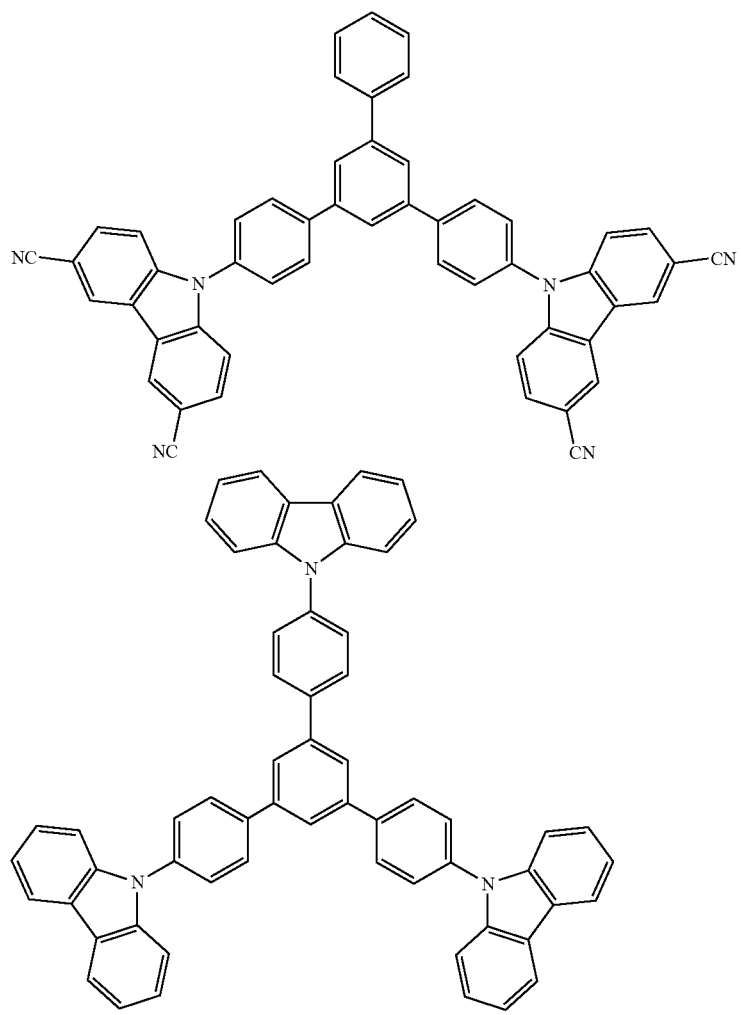

-continued
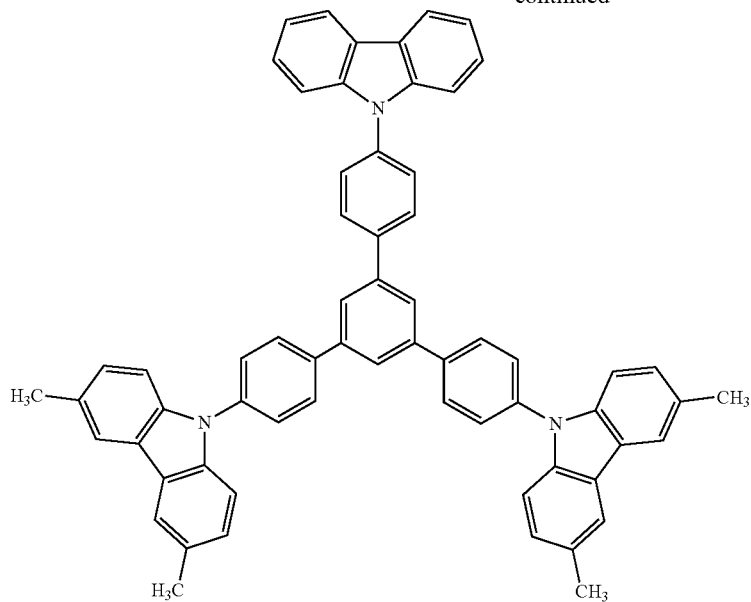
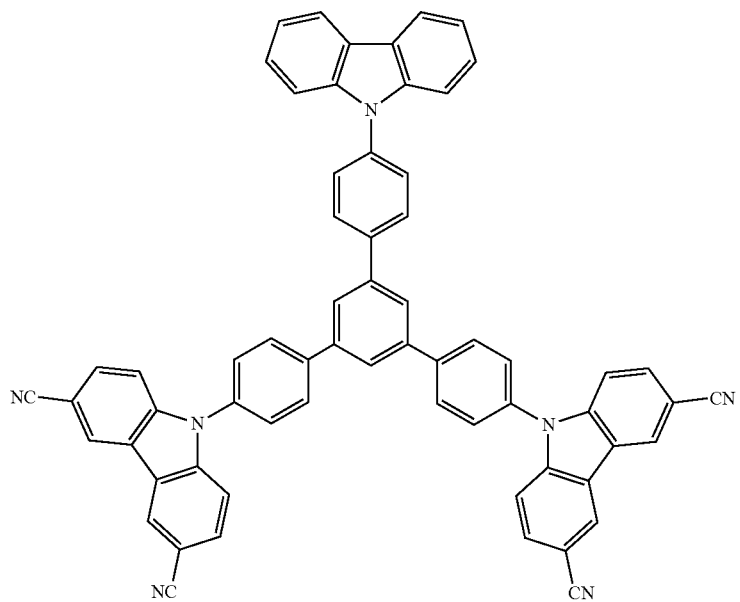

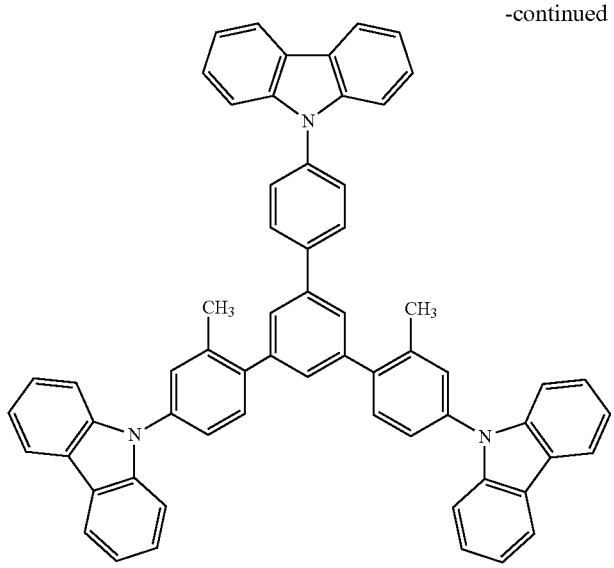
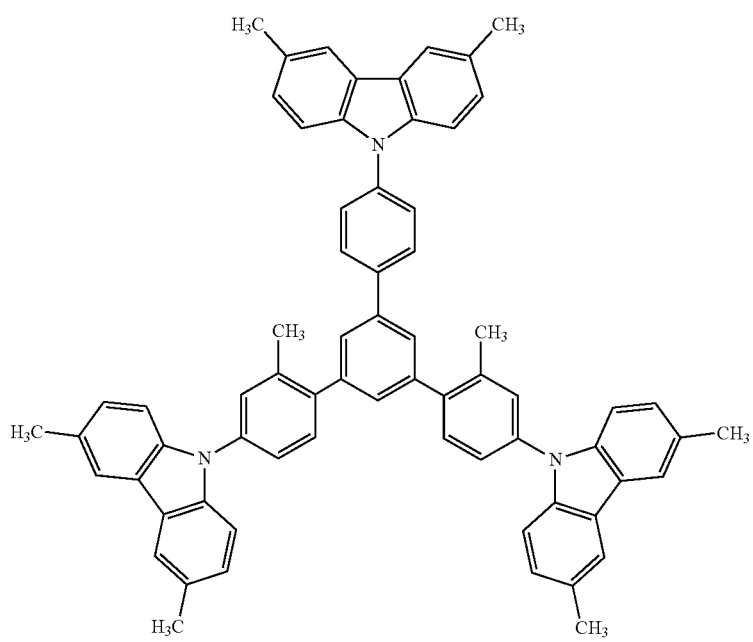

When the EML includes a host and a dopant (i.e., the organometallic complex represented by Formula 1-1 or Formula 1-2), an amount of the dopant in the EML may be in a range of about 0.01 to about 15 weight % based on 100 weight % of the EML, but the embodiment is not limited thereto.

A thickness of the EML may be in a range of about 200 Å to about 700 Å. When the thickness of the EML is within this range, excellent light emission characteristics may be obtained without a substantial increase in driving voltage.

Then, an ETL may be disposed on the EML by using various suitable methods, such as vacuum deposition, spin coating, or casting. When the ETL is formed by vacuum deposition and spin coating, the deposition and coating conditions may be determined in consideration of a compound for an ETL to be deposited by referring to the deposition and coating conditions for forming the HIL. As a material for the ETL, any suitable electron transporting material available in the art having capability of stably transporting electrons provided from a cathode may be used. Examples of such a material are a quinoline derivative, such as tris(8-quinoquinolinate)aluminum ($Alq_3$), TAZ, Balq, beryllium bis(benzoquinolin-10-olate) ($Bebq_2$), ADN, Compound 101, Compound 102, and Bphen, but the embodiment is not limited thereto.

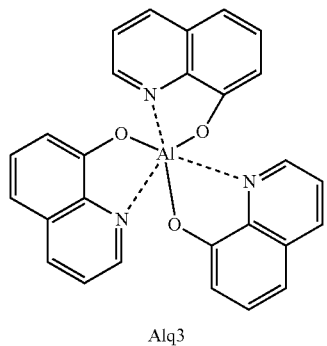

Alq3

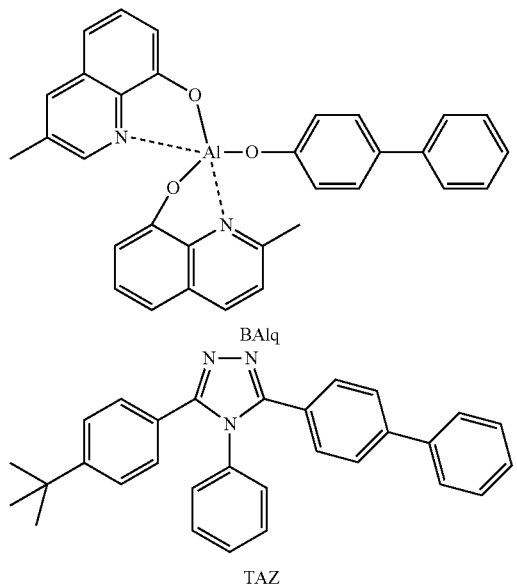

BAlq

TAZ

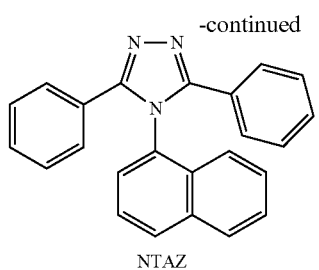

NTAZ

In some embodiments, the ETL may include at least one compound represented by Formula 601 below:

$$Ar_{601}\text{-}[(L_{601})_{xe1}\text{-}E_{601}]_{xe2}$$  Formula 601

In Formula 601, $Ar_{601}$ may be defined the same as $Ar_{301}$ provided herein, $L_{601}$ may be defined the same as $Ar_{101}$ provided herein, $E_{601}$ may be selected from:

a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spirofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, xe1 may be selected from 0, 1, 2, and 3, and xe2 may be selected from 1, 2, 3, and 4.

In some embodiments, the ETL may include at least one compound represented by Formula 602 below:

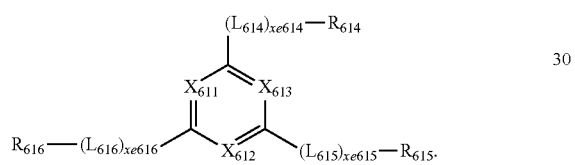

Formula 602

In Formula 602, $X_{611}$ may be N or C-$(L_{611})_{xe611}$-$R_{611}$, $X_{612}$ may be N or C-$(L_{612})_{xe612}$-$R_{612}$, and $X_{613}$ may be N or C-$(L_{613})_{xe613}$-$R_{613}$, and at least one selected from $X_{611}$ to $X_{613}$ may be N, descriptions of $L_{611}$ to $L_{616}$ may each understood by referring to the descriptions provided herein in connection with $Ar_{101}$, $R_{611}$ to $R_{616}$ may each be independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C1-C20 alkyl group, a C1-C20 alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xe611 to xe616 may each be independently selected from 0, 1, 2, and 3.

The compound represented by Formula 601 and the compound of 602 may include at least one selected from Compounds ET1 to ET15 below.

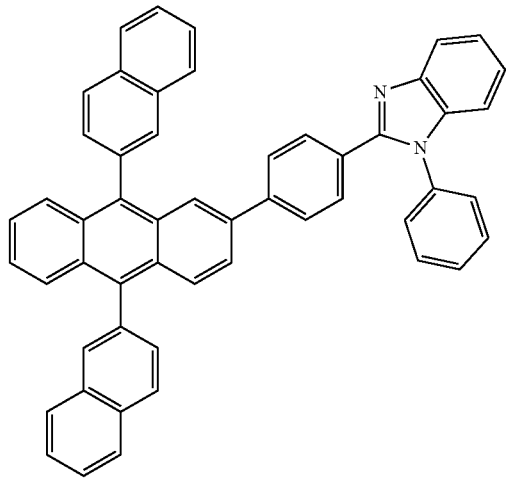

ET1

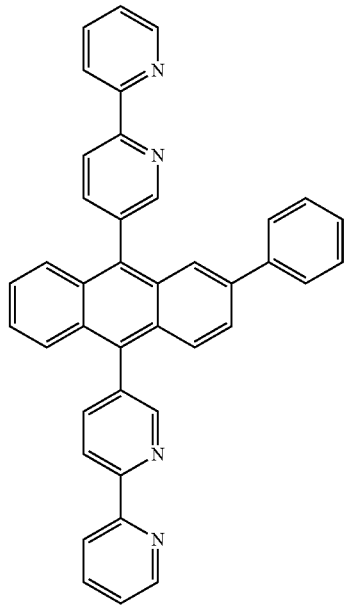

ET2

-continued
ET3
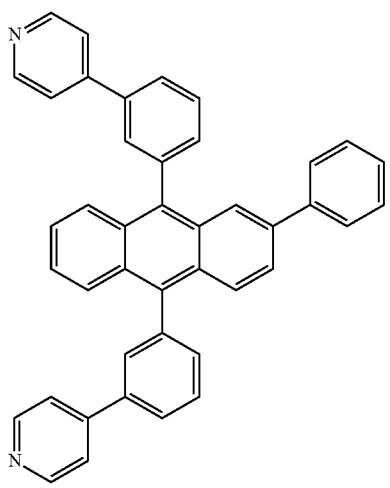
ET4
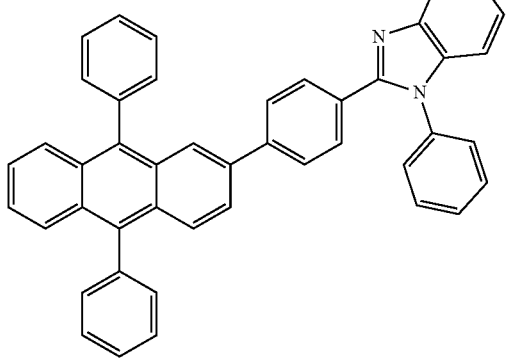
ET5
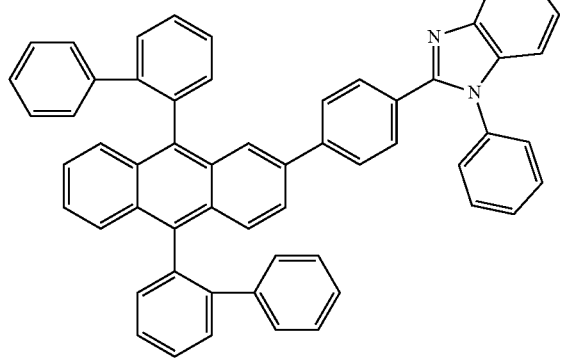
-continued
ET6
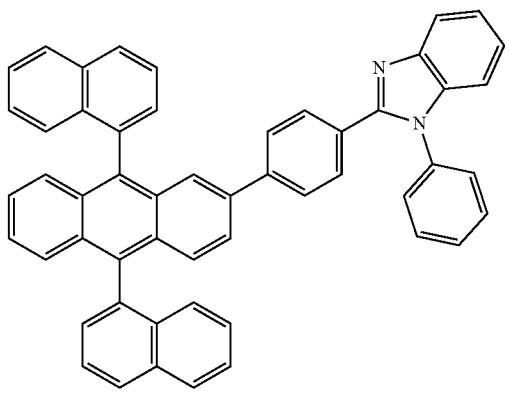
ET7
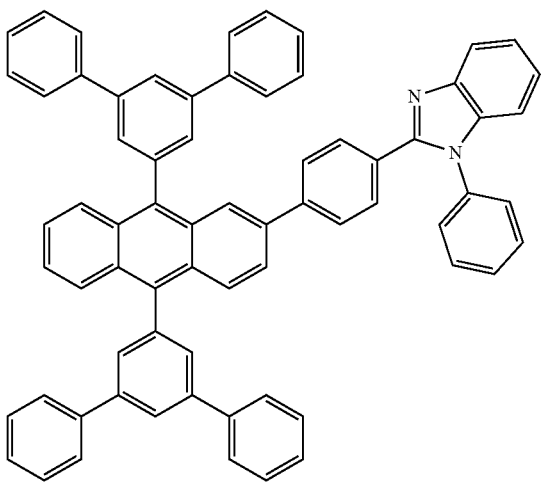
ET8
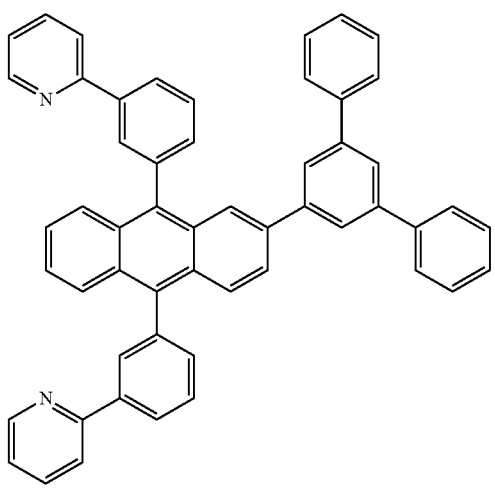

ET9
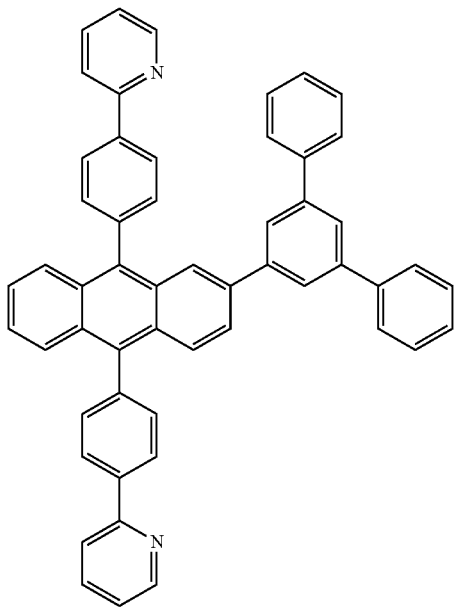
ET10
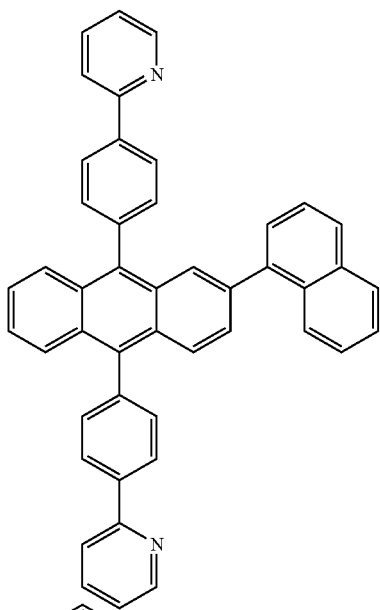
ET11
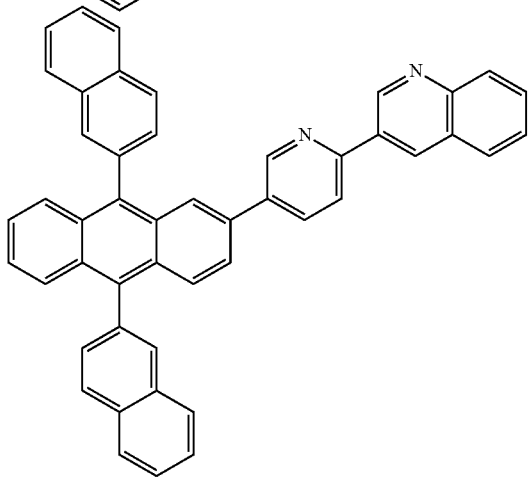
ET12
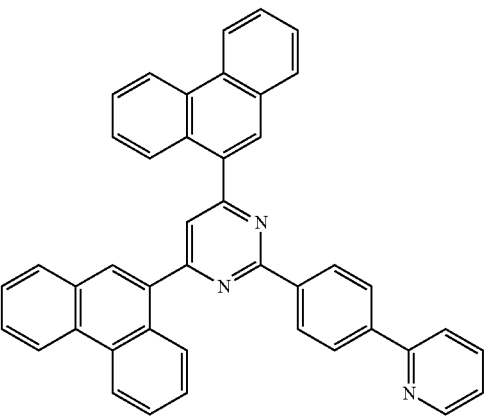
ET13
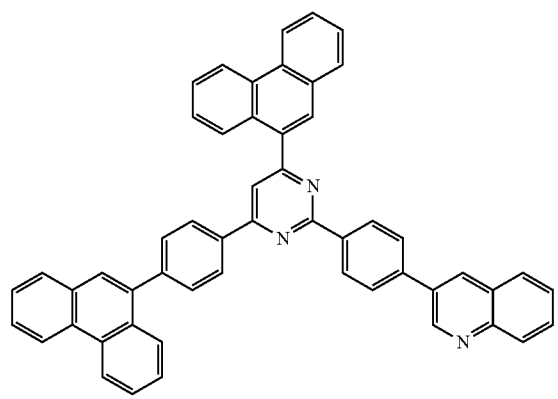
ET14
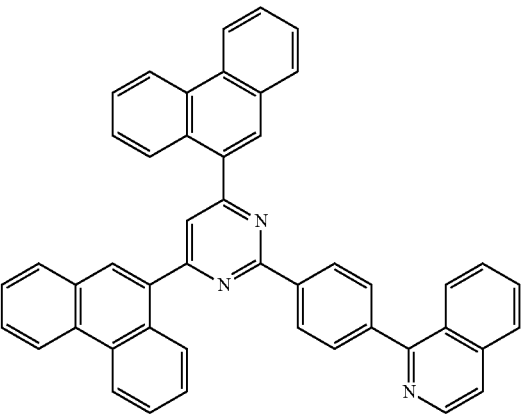

ET15

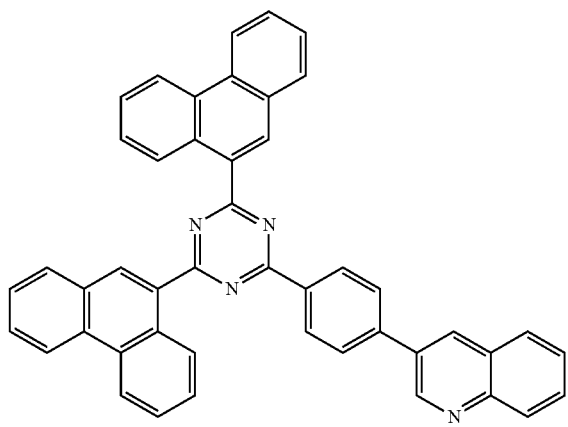

A thickness of the ETL may be in a range of about 100 Å to about 1,000 Å, e.g., about 150 Å to about 500 Å. When the thickness of the ETL is within these ranges, suitable or satisfactory electron transporting characteristics may be obtained without a substantial increase in driving voltage.

In some embodiments, the ETL may further include, in addition to the electron transporting organic compound described above, a metal-containing material.

The metal-containing material may include a Li complex. The Li complex may include, e.g., Compound LiQ (lithium quinolate, LiQ) or lithium[2-(2-hydroxyphenyl)benzothiazole] (LiBTz).

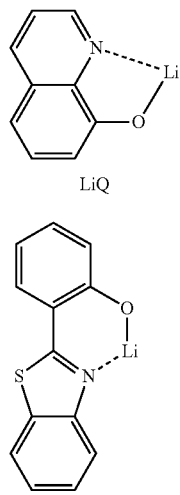

LiQ

In addition, an electron injection layer (EIL) may be disposed on the ETL to facilitate electron injection from a cathode, and a material for the EIL is not particularly limited.

Any suitable material available in the art to form an EIL, such as LiF, NaCl, CsF, $Li_2O$, or BaO, may be used herein. The deposition condition of the EIL may vary in consideration of a compound for an EIL to be deposited, but may be determined by referring to the deposition condition for forming the HIL.

A thickness of the EIL may be in a range of about 1 Å to about 100 Å, e.g., about 3 Å to about 90 Å. When the thickness of the EIL is within these ranges, suitable or satisfactory electron injecting characteristics may be obtained without a substantial increase in driving voltage.

A second electrode 17 may be disposed on the organic layer 15. The second electrode 17 may be a cathode, which is an electron injection electrode, and in this regard, a material for forming the second electrode 17 may be a material having a low work function. Such a material may include a metal, alloy, an electrically conductive compound, or a mixture thereof. Examples of the material for the second electrode 17 may include lithium (Li), magnesium (Mg), aluminum (Al), aluminum-lithium (Al—Li), calcium (Ca), magnesium-indium (Mg—In), or magnesium-silver (Mg—Ag), which may be formed as a thin film to manufacture a transmissive electrode. In some embodiments, the material for forming the second electrode 17 may be ITO or IZO, which may be used to manufacture a transmissive electrode as a top-emitting diode. Likewise, various suitable modifications of the organic light-emitting device are possible.

Hereinabove, the organic light-emitting device has been described with reference to the accompanying drawing.

In addition, when the EML includes a phosphorescent dopant, to prevent or reduce diffusion of excitons or holes into the ETL, a hole blocking layer (HBL) may be disposed between the HTL and the EML layer or between the HTL and the EML, by using various suitable methods, such as vacuum deposition, spin coating, casting, and a LB method. When the EBL is formed by vacuum deposition and spin coating, the deposition and coating conditions may be determined in consideration of a compound for an HBL to be deposited by referring to the deposition and coating conditions for forming the HIL. Any suitable hole blocking material available in the art may be used herein, and examples of such a material are an oxadiazole derivative, a triazole derivative, or a phenanthroline derivative. For example, the HBL may include at least one selected from BCP and Bphen, but the embodiment is not limited thereto.

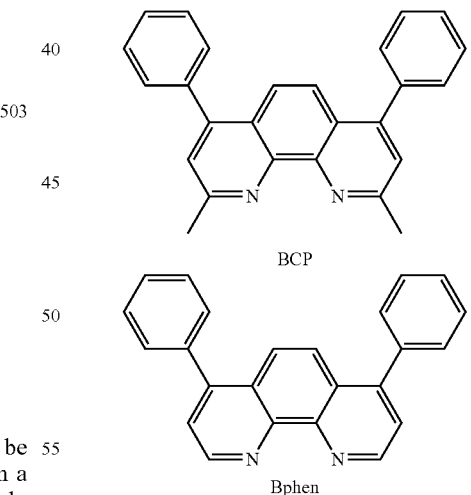

A thickness of the HBL may be in a range of about 20 Å to about 1,000 Å, e.g., about 30 Å to about 300 Å. When the thickness of the HBL is within these ranges, excellent hole blocking characteristics may be obtained without a substantial increase in driving voltage.

The term "alkyl group," as used herein, refers to a linear or branched aliphatic hydrocarbon monovalent group, and examples thereof include a methyl group, an ethyl group, a propyl group, an isobutyl group, a sec-butyl group, a terbutyl group, a pentyl group, an iso-amyl group, and a hexyl group. The term "alkylene group," as used herein, refers to a divalent group having the same structure as the alkyl group, except that the alkylene group is divalent instead of monovalent.

The term "alkoxy group," as used herein, refers to a monovalent group represented by —OA$_{101}$ (wherein A$_{101}$ is the C$_1$-C$_{60}$ alkyl group), and examples thereof include a methoxy group, an ethoxy group, and an isopropyloxy group.

The term "alkenyl group," as used herein, refers to a hydrocarbon group having at least one carbon-carbon double bond in a main chain (e.g., at the middle) or at a terminal end of the alkyl group, and examples thereof include an ethenyl group, a propenyl group, and a butenyl group. The term "alkenylene group," as used herein, refers to a divalent group having the same structure as the alkenyl group, except that the alkenylene group is divalent instead of monovalent.

The term "alkynyl group," as used herein, refers to a hydrocarbon group having at least one carbon-carbon triple bond in a main chain (e.g., in the middle) or at a terminal end of the alkyl group, and examples thereof include an ethynyl group and a propynyl group. The term "alkynylene group," as used herein, refers to a divalent group having the same structure as the alkynyl group, except that the alkynylene group is divalent instead of monovalent.

The term "cycloalkyl group," as used herein, refers to a monovalent hydrocarbon monocyclic group, and examples thereof include a cyclopropyl group, a cyclobutyl group, a cyclopentyl group, a cyclohexyl group, and a cycloheptyl group. The term "cycloalkylene group," as used herein, refers to a divalent group having the same structure as the cycloalkyl group (e.g., a C$_3$-C$_{10}$ cycloalkyl group), except that the cycloalkylene group is divalent instead of monovalent.

The term "heterocycloalkyl group," as used herein, refers to a monovalent monocyclic group having at least one hetero atom selected from N, O, P, and S as a ring-forming atom, and examples thereof include a tetrahydrofuranyl group, and a tetrahydrothiophenyl group. The term "heterocycloalkylene group," as used herein, refers to a divalent group having the same structure as the heterocycloalkyl group, except that the heterocycloalkylene group is divalent instead of monovalent.

The term "cycloalkenyl group," as used herein refers to a monovalent monocyclic group that has least one double bond in a ring thereof and does not have aromaticity (e.g., the ring is not aromatic), and examples thereof include a cyclopentenyl group, a cyclohexenyl group, and a cycloheptenyl group. The term "cycloalkenylene group," as used herein, refers to a divalent group having the same structure as the cycloalkenyl group, except that the cycloalkenylene group is divalent instead of monovalent.

The term "heterocycloalkenyl group," as used herein refers to a monovalent monocyclic group that has at least one hetero atom selected from N, O, P, and S as a ring-forming atom and at least one double bond in its ring. Examples of the heterocycloalkenyl group include a 2,3-hydrofuranyl group and a 2,3-hydrothiophenyl group. The term "heterocycloalkenylene group," as used herein refers to a divalent group having the same structure as the heterocycloalkenyl group, except that the heterocycloalkenylene group is divalent instead of monovalent.

The term "aryl group," as used herein, refers to a monovalent group having a carbocyclic aromatic system, and the term "arylene group," as used herein, refers to a divalent group having a carbocyclic aromatic system. Examples of the aryl group include a phenyl group, a naphthyl group, an anthracenyl group, a phenanthrenyl group, a pyrenyl group, and a chrysenyl group. When the aryl group and the arylene group each include two or more rings, the rings may be fused to each other (e.g., combined together).

The term "heteroaryl group," as used herein, refers to a monovalent group having a carbocyclic aromatic system that has at least one hetero atom selected from N, O, P, and S as a ring-forming atom. The term "heteroarylene group," as used herein refers to a divalent group having a carbocyclic aromatic system that has at least one hetero atom selected from N, O, P, and S as a ring-forming atom. Examples of the heteroaryl group include a pyridinyl group, a pyrimidinyl group, a pyrazinyl group, a pyridazinyl group, a triazinyl group, a quinolinyl group, and an isoquinolinyl group. When the heteroaryl group and the heteroarylene group each include two or more rings, the rings may be fused to each other (e.g., combined together).

The term "aryloxy group," as used herein, indicates —OA$_{102}$ (wherein A$_{102}$ is the aryl group), and the term "arylthio group," as used herein, indicates —SA$_{103}$ (wherein A$_{103}$ is the aryl group).

The term "monovalent non-aromatic condensed polycyclic group," as used herein, refers to a monovalent group that has two or more rings condensed to each other (e.g., combined together) and non-aromaticity in the entire molecular structure (e.g., the entire compound is not aromatic). The non-aromatic condensed polycyclic group may include, as a ring forming atom, i) only carbon atoms, or ii) a heteroatom selected from N, O, P, and S, other than carbon atoms. Examples of the monovalent non-aromatic condensed polycyclic group include a heptalenyl group and a triquinacenyl group. The term "divalent non-aromatic condensed polycyclic group," as used herein, refers to a divalent group having the same structure as the monovalent non-aromatic condensed polycyclic group, except that the divalent non-aromatic condensed polycyclic group is divalent instead of monovalent.

The expression "C$_m$-C$_n$ (m<n)," as used herein, indicates the number of carbon atoms from m to n. For example, as used herein, the term "C$_1$-C$_{10}$ alkyl group" refers to an alkyl group having 1 to 10 carbon atoms, and the term "C$_6$-C$_{30}$ aryl group" refers to an aryl group having 6 to 30 carbon atoms.

Hereinafter, an organic light-emitting device according to an embodiment is described in more detail with reference to Synthesis Example and Examples that are not to be construed as limiting the scope of the embodiments of the present disclosure.

SYNTHESIS EXAMPLES

Synthesis Example 1: Synthesis of Compound 11

Synthesis of Intermediate 1-1

Intermediate 1-1 was synthesized according to Equation 1-1 below:

Equation 1-1

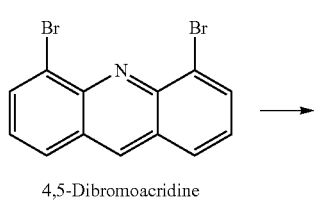

4,5-Dibromoacridine

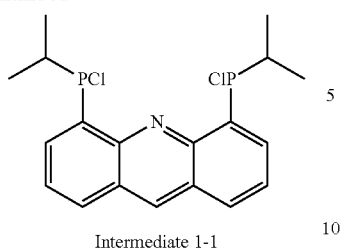

Intermediate 1-1

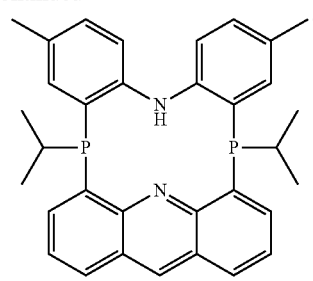

Intermediate 1-2

After 4,5-dibromoacridine (1 eq) was added to a flask and dissolved in 0.1 M THF, the flask was cooled to −78° C. n-BuLi (1.6 mol in Hexane, 1 eq) was slowly added to the flask, and then, the flask was stirred for 30 minutes while maintaining the temperature (−78° C.). The mixed product was slowly mixed with dichloro(isopropyl)phosphane, and then, after the temperature was raised to 0° C., the flask was stirred again for 2 hours. After the flask was cooled again to −78° C., n-BuLi (1.6 mol in Hexane, 1 eq) was slowly added thereto, and then, the flask was stirred for 30 minutes while maintaining the temperature (−78° C.). The mixed product was slowly mixed with dichloro(isopropyl)phosphane, and then, after the temperature was raised to room temperature, the flask was stirred again for 2 hours. After the completion of the reaction, the resulting product was extracted using MC, washed with distilled water, and dried using MgSO$_4$. Then, residues obtained after distillation under reduced pressure were subjected to column separation, so as to obtain Intermediate 1-1 (yield: 47%).

HRMS for $C_{19}H_{21}Cl_2NP_2$ calcd: 395.05. found: 394.

Elemental Analysis for $C_{19}H_{21}Cl_2NP_2$ calcd: C, 57.59; H, 5.34; Cl, 17.89; N, 3.54; P, 15.63.

Synthesis of Intermediate 1-2

Intermediate 1-2 was synthesized according to Equation 1-2 below:

Equation 1-2

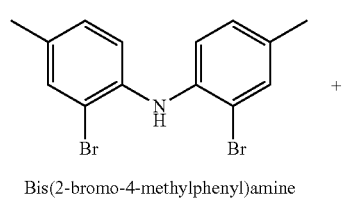

Bis(2-bromo-4-methylphenyl)amine

+

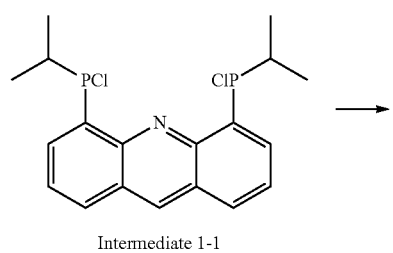

Intermediate 1-1

Intermediate 1-2 (yield: 52%) was obtained in the same manner as in Synthesis of Intermediate 1-1, except that bis(2-bromo-4-methylphenyl)amine was used instead of 4,5-dibromoacridine.

High Resolution Mass Spectrometry (HRMS) for $C_{21}H_{25}Cl_2NP_2$ calcd: 423.08. found: 422.

Elemental Analysis for $C_{21}H_{25}Cl_2NP_2$ calcd: C, 59.45; H, 5.94; Cl, 16.71; N, 3.30; P, 14.60.

Synthesis of Compound 11

Compound 11 was synthesized according to Equation 1-3 below:

Equation 1-3

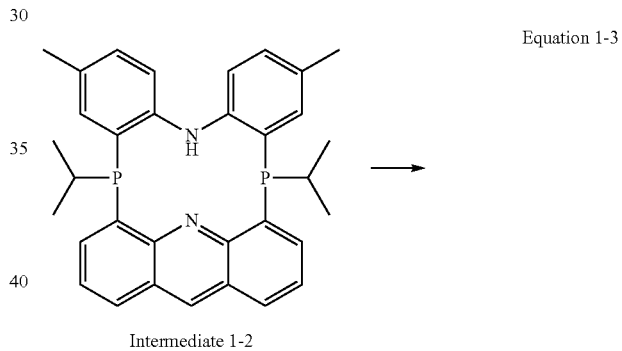

Intermediate 1-2

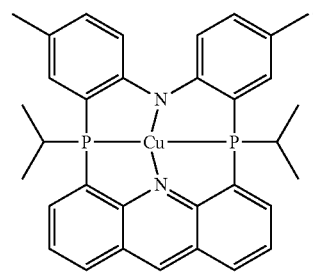

Compound 11

After the temperature of the flask in which Intermediate 1-2 (1 eq) was dissolved in THF was dropped to −78° C., n-BuLi (2 eq) was slowly added thereto. After the temperature of the flask was raised to room temperature, the flask was stirred for 3 hours. Then, the temperature of the reactants was dropped to −35° C., CuBr$_2$ (1 eq) dissolved in THF was added thereto, and the temperature of the flask was raised to room temperature, followed by being stirred for 24 hours. After the completion of the stirring, the solvent was removed according to a simple distillation method. The residual crude was dissolved in benzene, followed by being filtered using Cellite. Benzene was removed from the solution obtained therefrom under vacuum, and then, the solution was washed with pentane, so as to obtain a yellow solid product, i.e., Compound 11 (yield: 41%).

HRMS for $C_{33}H_{33}CuN_2P_2$ [M]+: calcd: 583.13. found: 582.

Elemental Analysis for $C_{33}H_{33}CuN_2P_2$ calcd: C, 67.97; H, 5.70; Cu, 10.90; N, 4.80; P, 10.62.

Synthesis Example 2: Synthesis of Compound 44

Synthesis of Intermediate 2-1

Intermediate 2-1 was synthesized according to Equation 2-1 below:

Equation 2-1

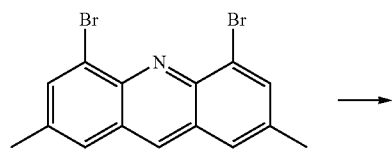

4,5-dibromo-2,7-dimethylacridine

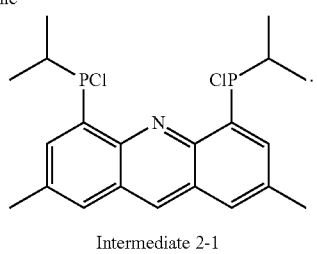

Intermediate 2-1

Intermediate 2-1 (yield: 52%) was obtained in the same manner as in Synthesis of Intermediate 1-1, except that 4,5-dibromo-2,7-dimethylacridine was used instead of 4,5-dibromoacridine.

HRMS for $C_{21}H_{25}Cl_2NP_2$ [M]+: calcd: 423.08. found: 422.

Elemental Analysis for $C_{21}H_{25}Cl_2NP_2$ calcd: C, 59.45; H, 5.94; Cl, 16.71; N, 3.30; P, 14.60.

Synthesis of Intermediate 2-2

Intermediate 2-2 was synthesized according to Equation 2-2 below:

Equation 2-2

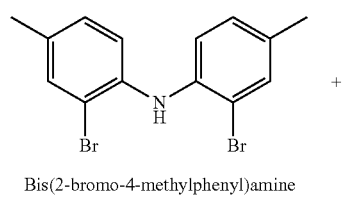

Bis(2-bromo-4-methylphenyl)amine

+

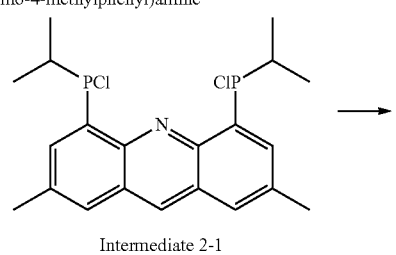

Intermediate 2-1

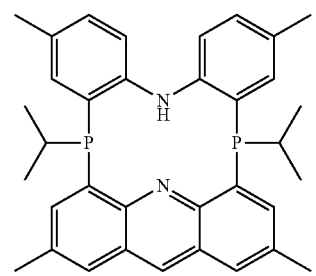

Intermediate 2-2

Intermediate 2-2 (yield: 52%) of Intermediate 2-1 was synthesized in the same manner as in Synthesis of Intermediate 1-2, except that instead of Intermediate 2-1 was used Intermediate 1-1.

HRMS for $C_{35}H_{38}N_2P_2$ [M]+: calcd: 548.25. found: 547.

Elemental Analysis for $C_{35}H_{38}N_2P_2$ calcd: C, 76.62; H, 6.98; N, 5.11; P, 11.29.

Synthesis of Compound 44

Compound 44 was synthesized according to Equation 2-3 below:

Equation 2-3

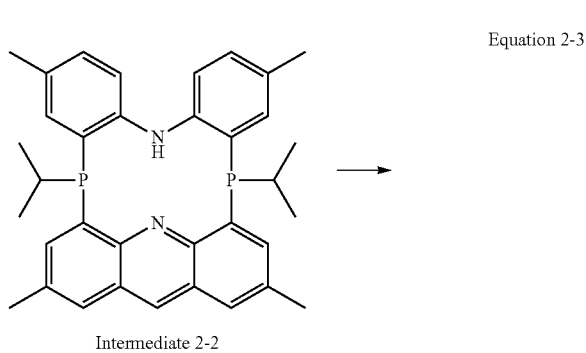

Intermediate 2-2

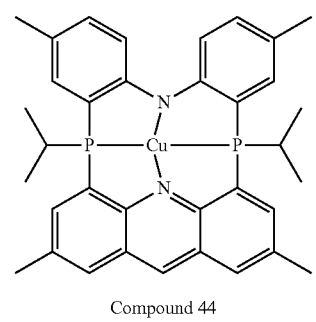

Compound 44

Compound 44 (yield: 42.5%) was obtained in the same manner as in Synthesis of Compound 11, except that Intermediate 2-2 was used instead of Intermediate 1-2.

HRMS for $C_{35}H_{37}CuN_2P_2$ [M]+: calcd: 611.19. found: 610.

Elemental Analysis for $C_{35}H_{37}CuN_2P_2$ calcd: C, 68.78; H, 6.10; Cu, 10.40; N, 4.58; P, 10.14.

Example 1

As an anode, an ITO glass substrate (a product of Corning Co., Ltd) having a sheet resistance of 15 Ω/cm² and a thickness of 1,200 Å was cut to a size of 50 mm×50 mm×0.5 mm, and then, sonicated by using isopropyl alcohol and pure water each for 5 minutes, and cleaned by the exposure to ultraviolet rays for 30 minutes, and then, ozone. The ITO glass substrate was accordingly mounted on a vacuum deposition apparatus.

m-MTDATA was vacuum deposited on the ITO glass substrate to form an HIL having a thickness of 600 Å, and then, NPB was vacuum deposited on the HIL to form an HTL having a thickness of 300 Å. Then, Compound 11 (dopant) and CBP (host) were vacuum deposited at a deposition rate of 0.01 Å/sec and 1 Å/sec, respectively, on the HTL to form an EML having a thickness of 300 Å. Compound Alq₃ was vacuum deposited on the EML to form an ETL having a thickness of 300 Å. Then, Compound LiF was deposited on the ETL to form an EIL having a thickness of about 10 Å, and Al was vacuum deposited on the EIL to form a cathode having a thickness of 2,000 Å, thereby completing the manufacture of an organic light-emitting device.

m-MTDATA

NPB

CBP

Alq₃

Example 2

An organic light-emitting device was manufactured in the same manner as in Example 1, except that in forming the E, Compound 44 was used as a dopant instead of Compound 11.

Comparative Example 1

An organic light-emitting device was manufactured in the same manner as in Example 1, except that in forming the EML, PD1 was used as a dopant instead of Compound 11.

Evaluation Example

The current density, driving voltage, and efficiency of the organic light-emitting devices manufactured according to Examples 1 and 2 and Comparative Example 1 were measured by using a PR650 Spectroscan Source Measurement Unit (a product of PhotoResearch). The measurement results are shown in Table 1 below.

TABLE 1

| | Dopant | Current density (mA/cm²) | Driving voltage (V) | Efficiency (cd/A) |
|---|---|---|---|---|
| Example 1 | Compound 11 | 10 | 5.8 V | 29.2 |
| Example 2 | Compound 44 | 10 | 5.9 V | 30.5 |
| Comparative Example 1 | PD1 | 10 | 6.0 V | 28.0 |

11

-continued

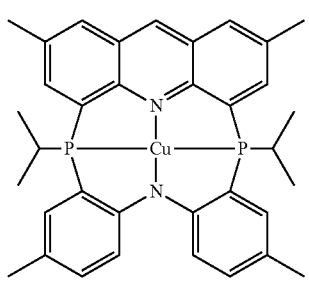

44

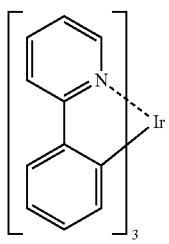

PD1

From Table 1, it was confirmed that the organic light-emitting devices manufactured according to Examples 1 and 2 had excellent efficiency compared to the organic light-emitting device manufactured according to Comparative Example 1.

An organic light-emitting device including the organometallic complex according to an embodiment may have high efficiency and high color purity.

It will be understood that, although the terms "first," "second," "third," etc., may be used herein to describe various elements, components, regions, layers and/or sections (e.g., a first electrode and a second electrode), these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present invention.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present invention. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the accompanying drawing, it will be understood by those of ordinary skill in the art that various changes in form and details may be made therein without departing from the spirit and scope as defined by the following claims, and equivalents thereof.

What is claimed is:

1. An organometallic complex represented by Formula 1-1 or Formula 1-2:

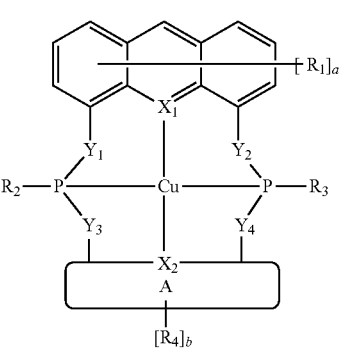

Formula 1-1

-continued

Formula 1-2

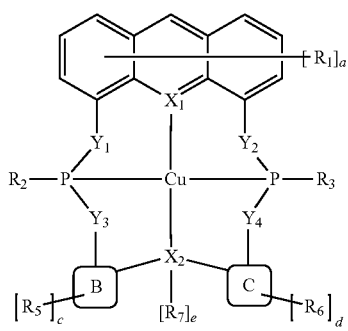

wherein, in Formulae 1-1 and 1-2, a ring A is a condensed ring comprising $X_2$, a ring B and a ring C are each independently a substituted or unsubstituted $C_6$-$C_{40}$ aromatic ring, a substituted or unsubstituted $C_2$-$C_{40}$ hetero aromatic ring, or a substituted or unsubstituted $C_3$-$C_{10}$ cycloalkene group, $X_1$ is carbon (C), nitrogen (N), or phosphorus (P), and $X_2$ is C, N, P, oxygen (O) or sulfur (S), $Y_1$ to $Y_4$ are each independently a direct bond, O, S, a substituted or unsubstituted $C_1$-$C_{10}$ alkylene group, a substituted or unsubstituted $C_6$-$C_{40}$ arylene group, or a substituted or unsubstituted $C_1$-$C_{40}$ heteroarylene group, $R_1$ to $R_6$ are each independently selected from the group consisting of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_1$-$C_{10}$ heterocycloalkyl group, a substituted or unsubstituted $C_1C_{10}$ heterocycloalkenyl group, a substituted or unsubstituted $C_6$-$C_{40}$ aryl group, a substituted or unsubstituted $C_1$-$C_{40}$ heteroaryl group, a substituted or unsubstituted $C_6$-$C_{40}$ aryloxy group, a substituted or unsubstituted $C_6$-$C_{40}$ arylthio group, —$N(Q_1)(Q_2)$, —$C(=O)(Q_3)$, and —$Si(Q_4)(Q_5)(Q_6)$ (wherein $Q_1$ to Q are each independently a hydrogen, a substituted or unsubstituted $C_1$-$C_{20}$ alkyl group, a substituted or unsubstituted $C_6$-$C_{40}$ aryl group, or a substituted or unsubstituted $C_1$-$C_{40}$ heteroaryl group), wherein optionally $R_2$ and $R_3$ are each independently (=O), R is a substituted or unsubstituted $C_6$-$C_{40}$ aryl group or a substituted or unsubstituted $C_2$-$C_{40}$ heteroaryl group, a is an integer of 1 to 7, and when a is 2 or more, a plurality of $R_1$s are independent of each other, b is an integer of 1 to 7, and when b is 2 or more, a plurality of $R_4$s are independent of each other, c is an integer of 1 to 4, and when c is 2 or more, a plurality of $R_5$s are independent of each other, d is an integer of 1 to 4, and when d is 2 or more, a plurality of $R_6$s are independent of each other, and e is 0 or 1.

2. The organometallic complex of claim 1, wherein $R_1$ to $R_6$ are selected from the group consisting of:

a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from the group consisting of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a $C_6$-$C_{40}$ aryl group and a $C_1$-$C_{40}$ heteroaryl group;

a $C_6$-$C_{40}$ aryl group and a $C_1$-$C_{40}$ heteroaryl group, each substituted with at least one selected from the group consisting of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{40}$ aryl group, and a $C_1$-$C_{40}$ heteroaryl group; and —$N(Q_1)(Q_2)$, wherein, optionally, $R_2$ and $R_3$ are each independently (=O), and $Q_1$ to $Q_2$ are each independently selected from the group consisting of:

a hydrogen atom, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from the group consisting of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a $C_6$-$C_{40}$ aryl group and a $C_1$-$C_{40}$ heteroaryl group; and a $C_6$-$C_{40}$ aryl group and a $C_1$-$C_{40}$ heteroaryl group, each substituted with at least one selected from the group consisting of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{40}$ aryl group, and a $C_1$-$C_{40}$ heteroaryl group, and $R_7$ is selected from the group consisting of a $C_6$-$C_{40}$ aryl group and a $C_1$-$C_{40}$ heteroaryl group; and a $C_6$-$C_{40}$ aryl group and a $C_1$-$C_{40}$ heteroaryl group, each substituted with at least one selected from the group consisting of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{40}$ aryl group, and a $C_1$-$C_{40}$ heteroaryl group.

3. The organometallic complex of claim 1, wherein $R_1$ to $R_3$ are each independently selected from the group consisting of:

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonenyl group, an isononenyl group, a sec-nonenyl group, a tert-nonenyl group, an n-decanyl group, an isodecanyl group, a sec-decanyl group, and a tert-decanyl group;

a phenyl group, a naphthyl group, an anthryl group, a pyrenyl group, a phenanthrenyl group, a fluorenyl group, an indenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group; and a phenyl group substituted with at least one fluorine (F), a naphthyl group, an anthryl group, a pyrenyl group, a phenanthrenyl group, a fluorenyl group, an indenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group, $R_4$ to $R_6$ are each independently selected from the group consisting of:

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonenyl group, an isononenyl group, a sec-nonenyl group, a tert-nonenyl group, an n-decanyl group, an isodecanyl group, a sec-decanyl group, a tert-decanyl group, a methoxy group, an ethoxy group, a propoxy group, n-butoxy group, an isobutoxy group, a sec-butoxy group, and a tert-butoxy group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonenyl group, an isononenyl group, a sec-nonenyl group, a tert-nonenyl group, an n-decanyl group, an isodecanyl group, a sec-decanyl group, a tert-decanyl group, a methoxy group, an ethoxy group, a propoxy group, n-butoxy group, an isobutoxy group, a sec-butoxy group, and a tert-butoxy group, each substituted with at least one selected from the group consisting of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthryl group, a pyrenyl group, a phenanthrenyl group, a fluorenyl group, an indenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group; and a phenyl group, a naphthyl group, an anthryl group, a pyrenyl group, a phenanthrenyl group, a fluorenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group, each substituted with at least one selected from the group consisting of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyrenyl group, a phenanthrenyl group, a fluorenyl group, an indenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group, and $R_7$ is selected from the group consisting of a phenyl group, a naphthyl group, an anthryl group, a pyrenyl group, a phenanthrenyl group, a fluorenyl group, a pyridyl group, a pyrazinyl group, a pyrimidinyl group, a triazinyl group, a quinolinyl group, an isoquinolinyl group, a quinoxalinyl group, a phenanthrolinyl group, and a carbazolyl group.

4. The organometallic complex of claim 1, wherein the ring A comprising $X_2$ is an anthracene, an acridine, an acridophosphine, a xanthene, or a thioxanthene.

5. The organometallic complex of claim 1, wherein the ring B and the ring C each independently comprise a benzene, a naphthylene, an indene, a cyclopentadiene, or a benzoimidazole.

6. The organometallic complex of claim 1, wherein

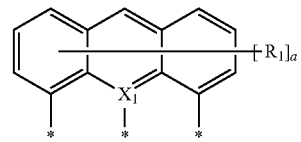

in Formulae 1-1 and 1-2 is represented by one of Formulae 2A to 2G:

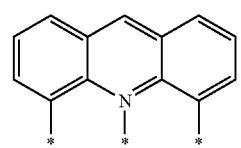

2A

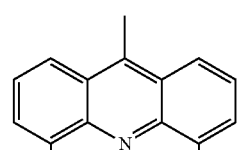

2B

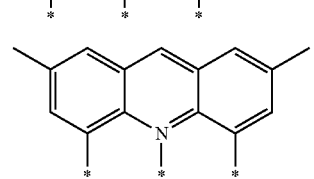

2C

-continued

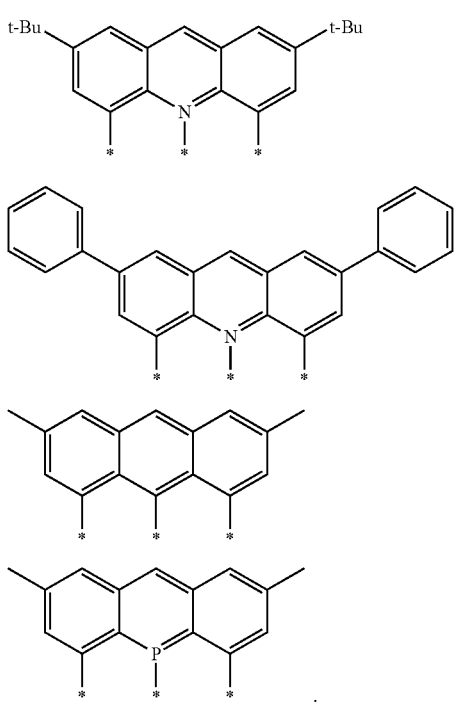

wherein, in Formulae 2A to 2G, * indicates a binding site.

7. The organometallic complex of claim 1, wherein $Y_1$ to $Y_4$ are each independently a direct bond.

8. The organometallic complex or claim 1, wherein $Y_1$ and $Y_2$ are each independently —$CH_2$—, and $Y_3$ and $Y_4$ are each independently a direct bond.

9. The organometallic complex or claim 1, wherein $Y_1$ and $Y_2$ are each independently a direct bond, and $Y_3$ and $Y_4$ are each independently —$CH_2$—.

10. The organometallic complex or claim 1, wherein $Y_1$ and $Y_2$ are each independently —O—, and $Y_3$ and $Y_4$ are each independently a direct bond.

11. The organometallic complex or claim 1, wherein $Y_1$ to $Y_4$ are each independently —$CH_2$—.

12. The organometallic complex or claim 1, wherein $R_2$ and $R_3$ each independently comprise an iso-propyl group, a phenyl group, (=O), or a 4-fluorophenyl group.

13. The organometallic complex or claim 1, wherein

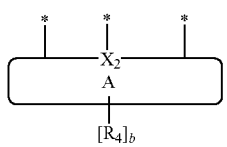

in Formula 1-1 is represented by one of Formulae 3A to 3C:

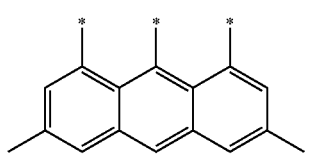

-continued

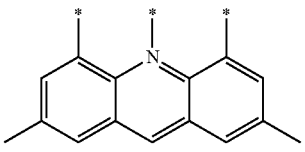

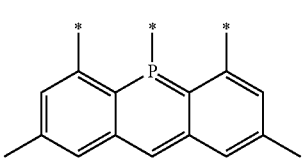

wherein, in Formulae 3A to 3C, * indicates a binding site.

14. The organometallic complex or claim 1, wherein

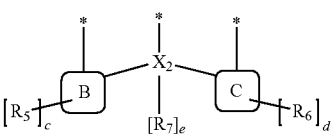

in Formula 1-2 is represented by one of Formulae 4A to 4I:

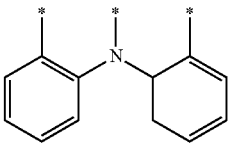

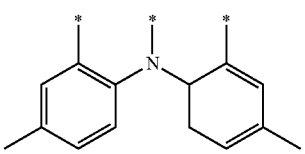

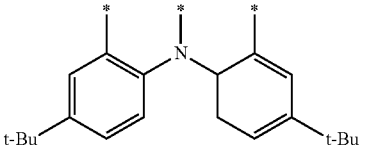

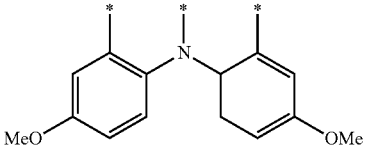

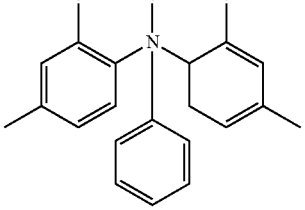

-continued
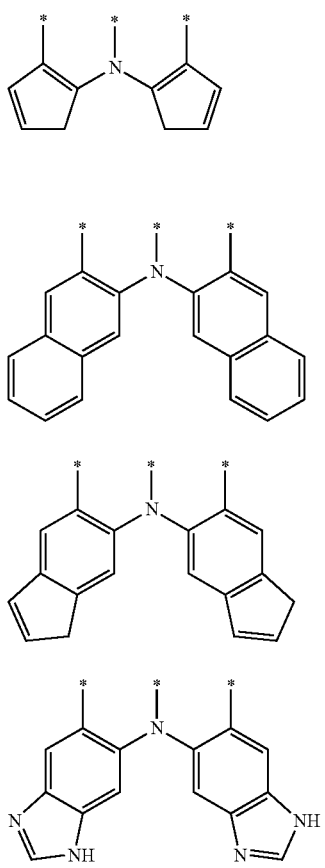
4F
4G
4H
4I
wherein, in Formulae 4A to 4I, * indicates a binding site.
15. The organometallic complex of claim 1, wherein the organometallic complex is one of Compounds 1 to 61:
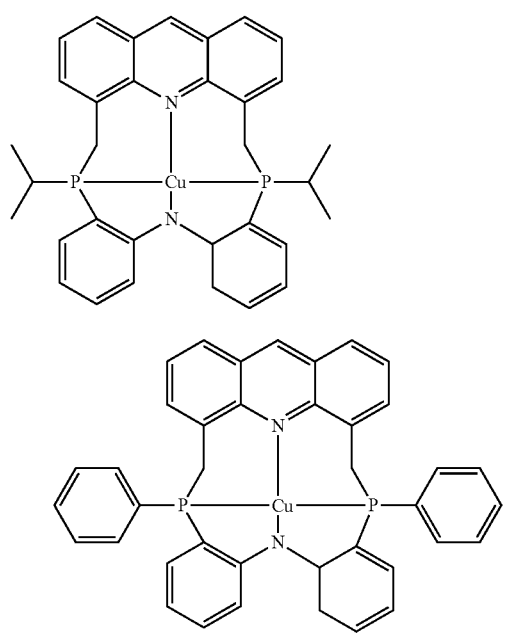
1
2
-continued
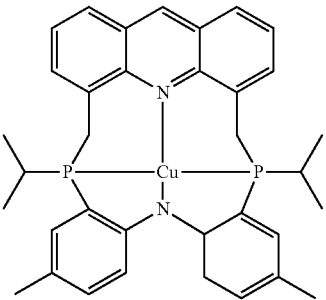
3
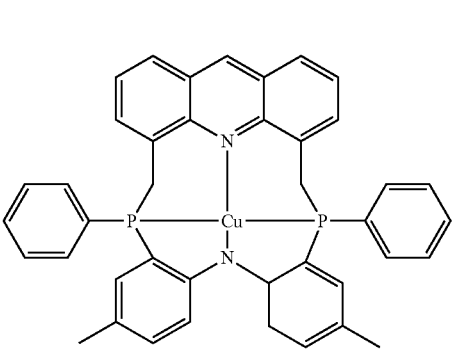
4
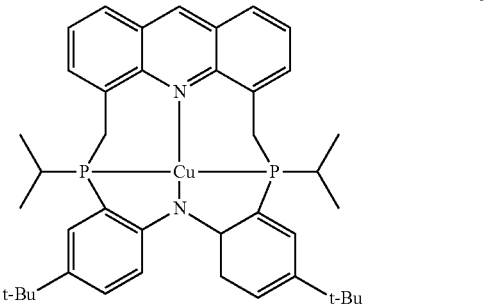
5
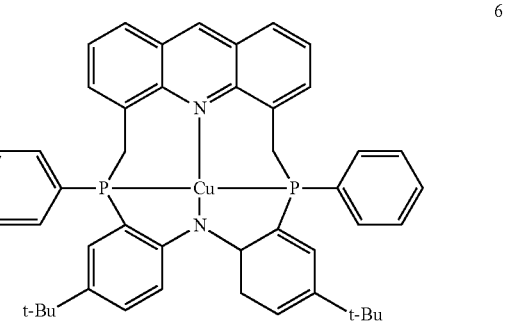
6
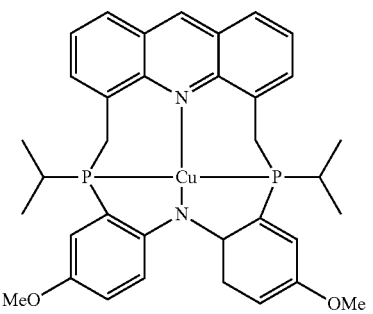
7

8
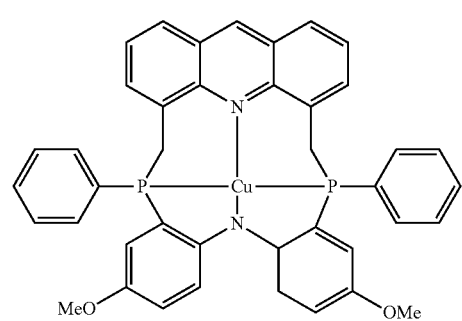
9
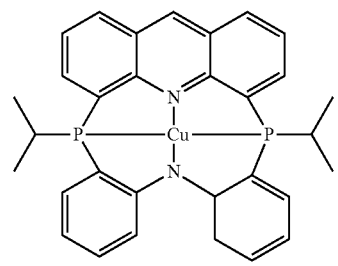
10
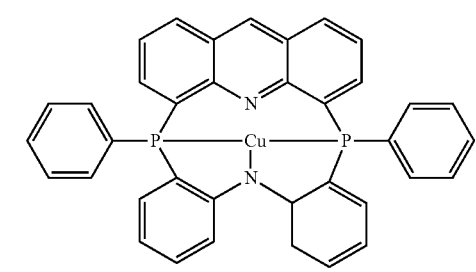
11
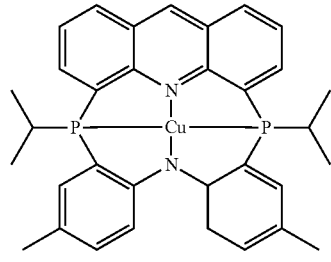
12
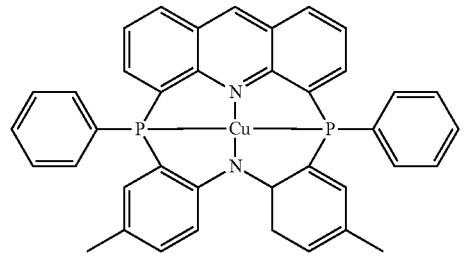
13
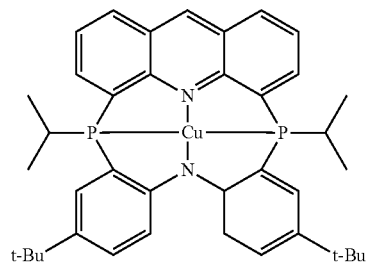
14
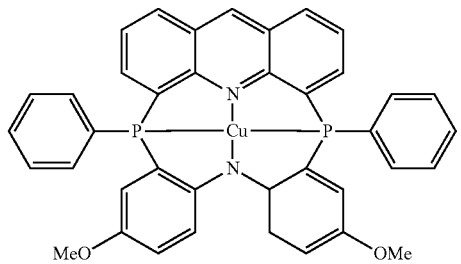
15
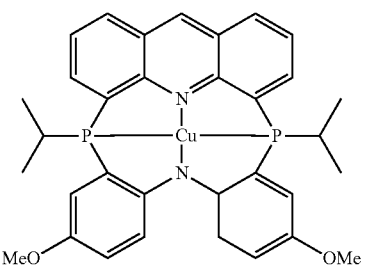
16
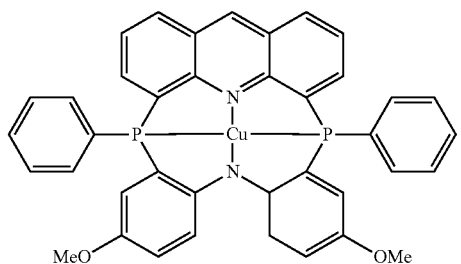
17
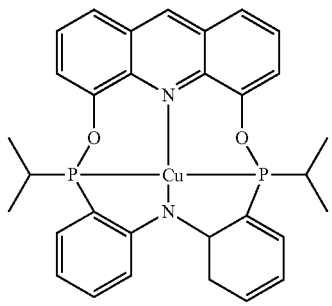
18
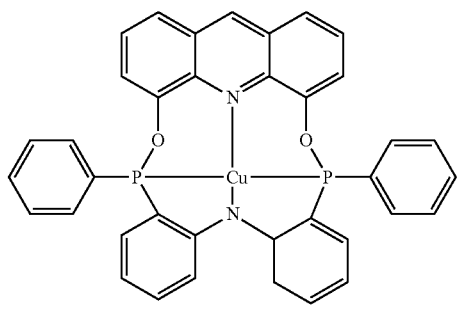

19
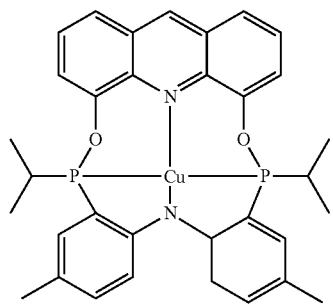
20
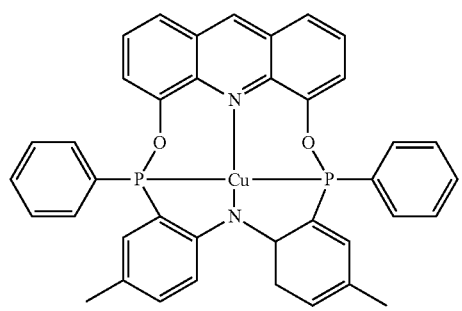
21
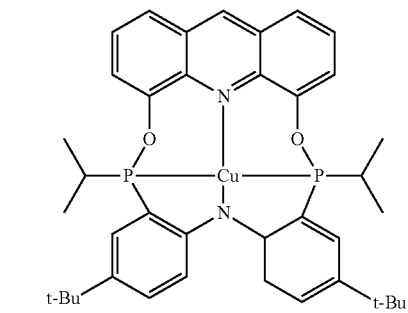
22
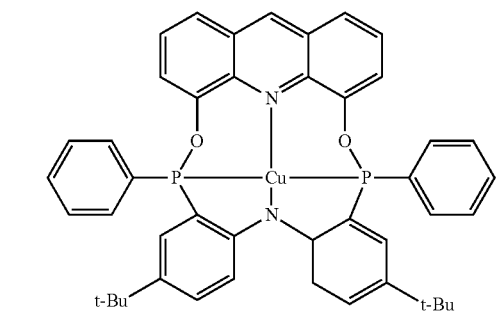
23
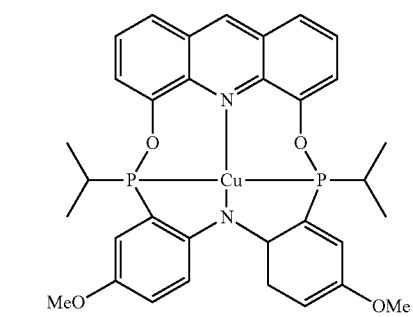
24
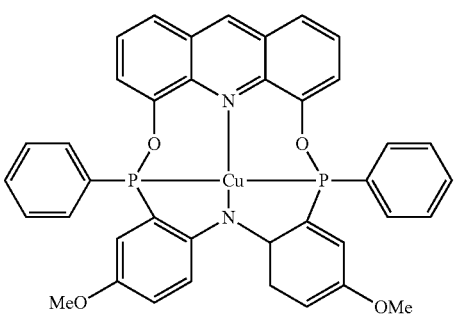
25
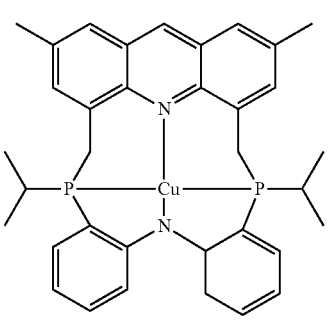
26
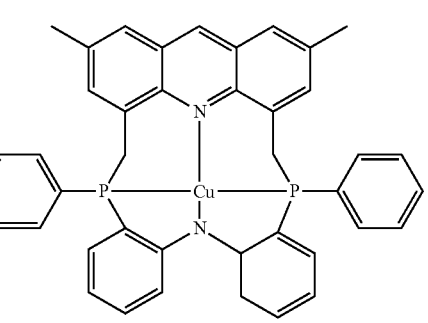
27
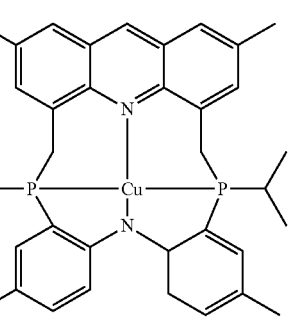
28
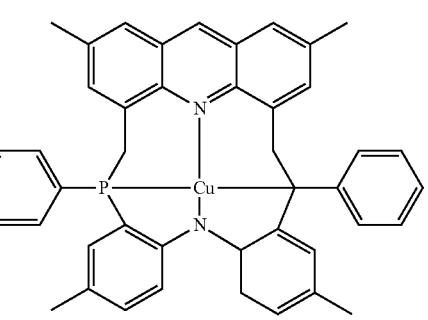

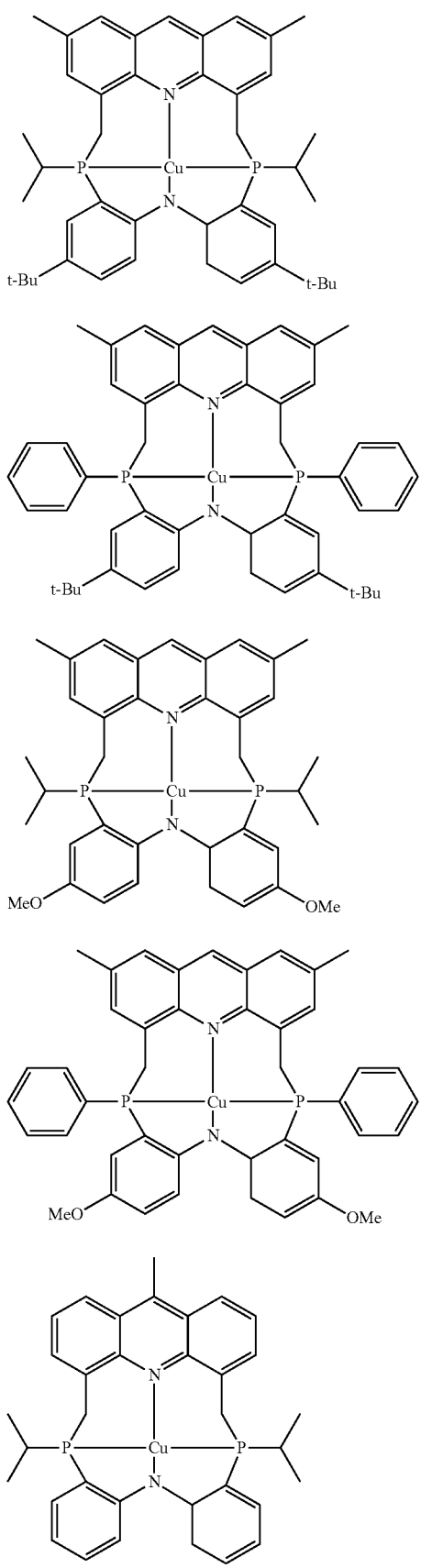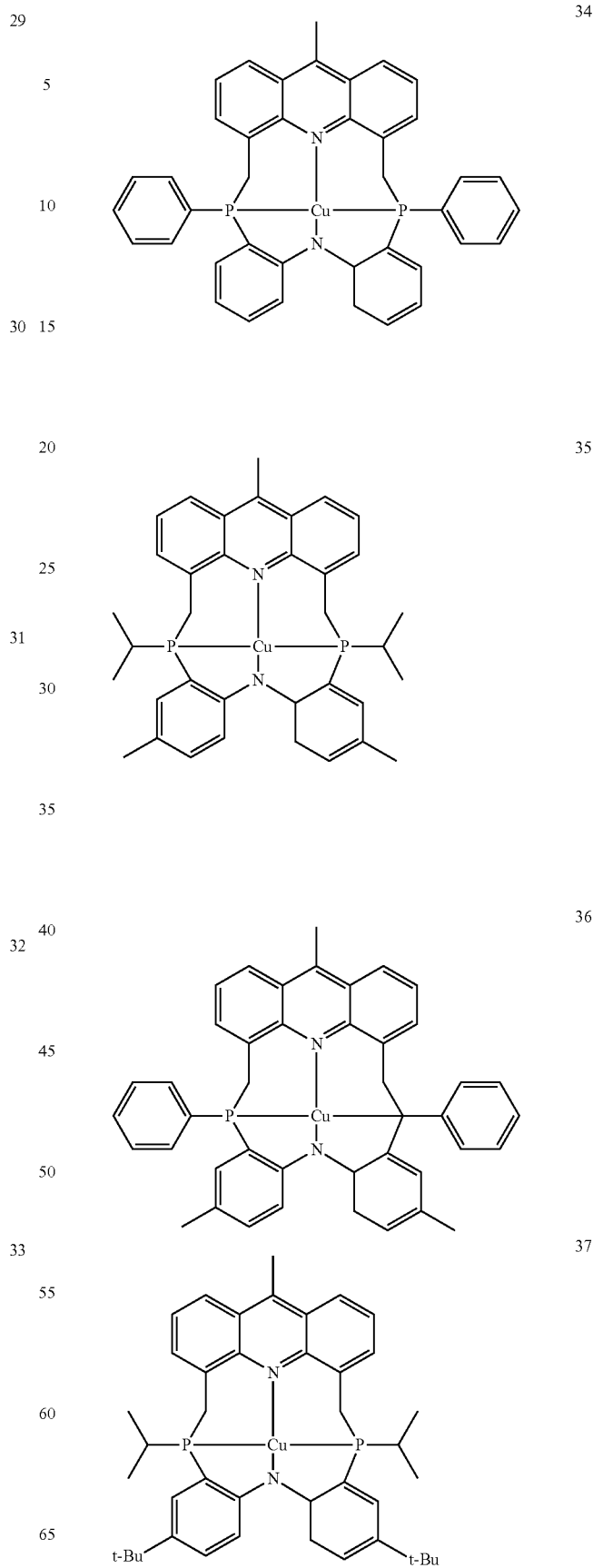

38
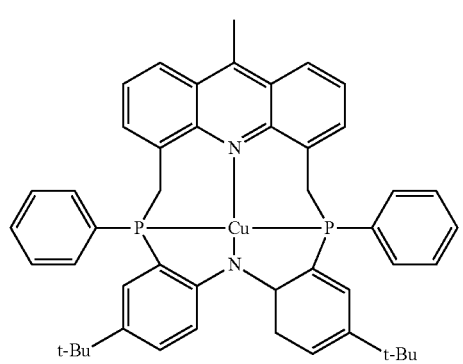
39
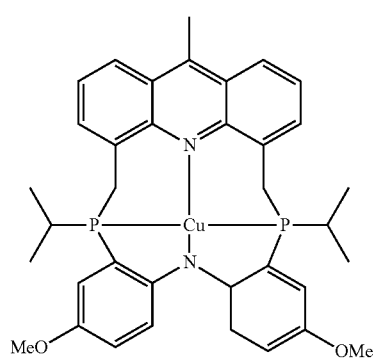
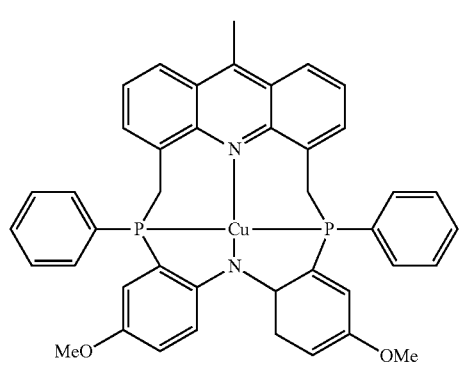
41
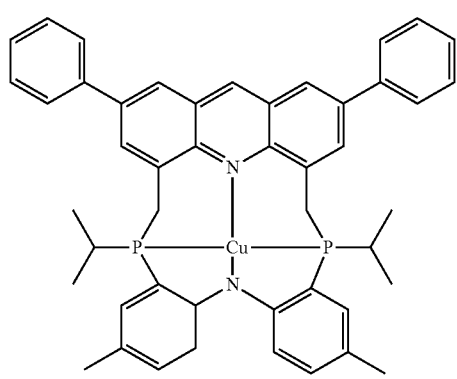
42
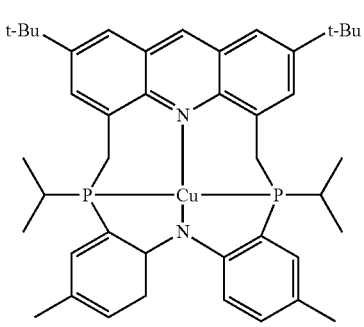
43
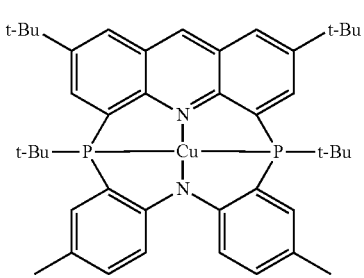
44
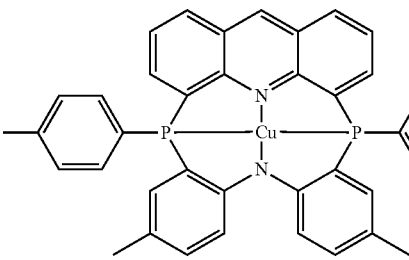
45
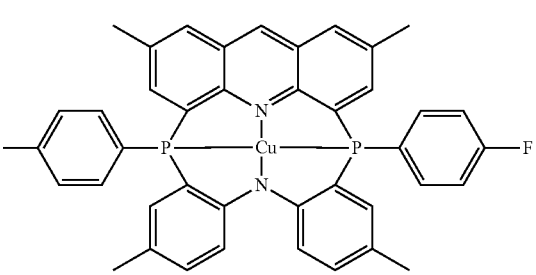
46

47
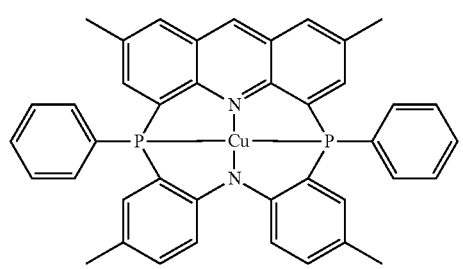
48
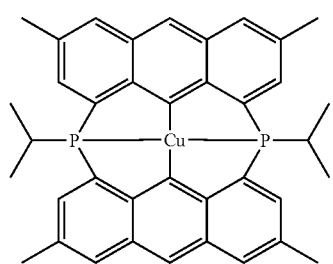
49
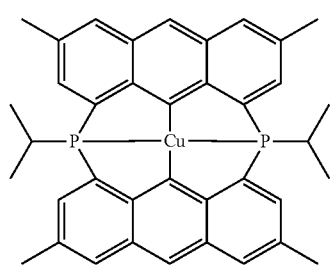
50
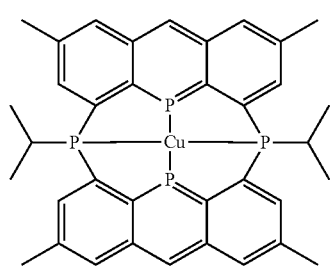
51
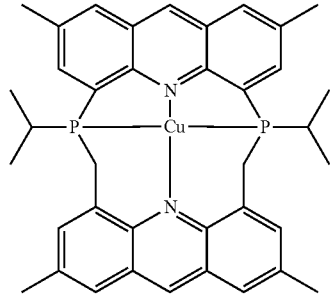
52
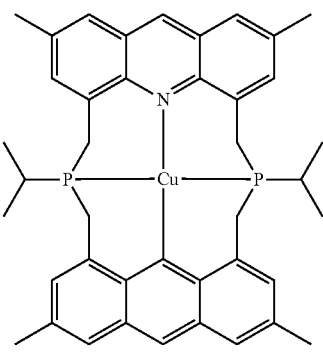
53
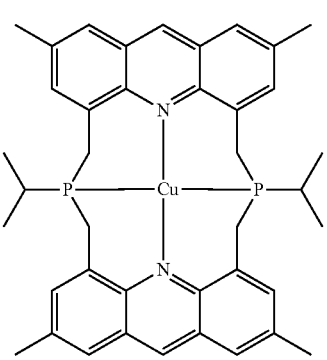
54
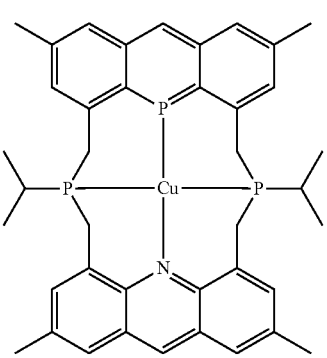
55
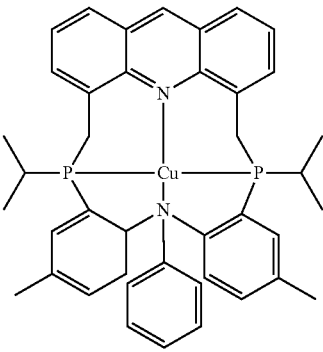

109
-continued

56
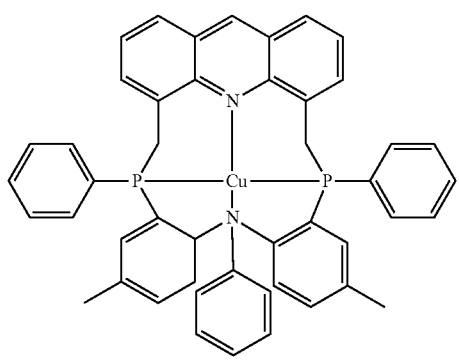

57
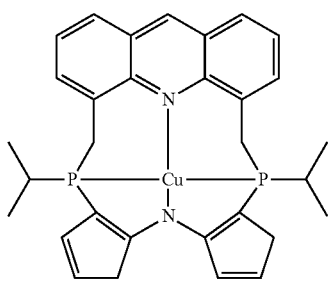

58
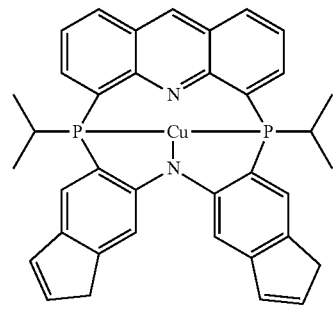

59
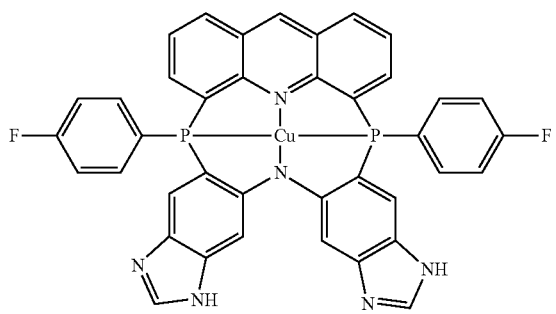

110
-continued

60
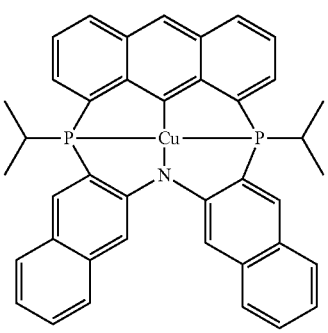

61
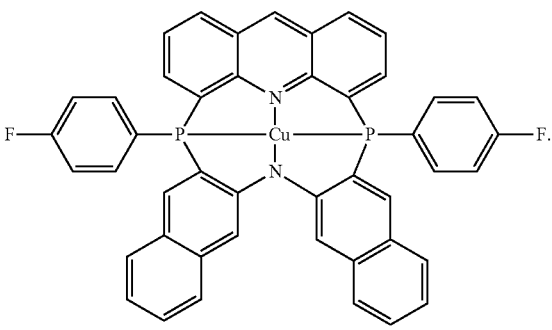

16. An organic light-emitting device comprising:
a first electrode;
a second electrode facing the first electrode; and
an organic layer that is disposed between the first electrode and the second electrode and comprises an emission layer, wherein the organic layer comprises the organometallic complex of claim 1.

17. The organic light-emitting device of claim 16, wherein the organic layer further comprises, between the first electrode and the emission layer, at least one selected from the group consisting of a hole injection layer, a hole transport layer, a hole injection-transport layer having both hole injecting and transporting capabilities, a buffer layer, and an electron blocking layer, and between the emission layer and the second electrode, at least one selected from the group consisting of a hole blocking layer, an electron transport layer, and an electron injection layer.

18. The organic light-emitting device of claim 16, wherein the emission layer comprises the organometallic complex and a host, wherein the organometallic complex serves as a phosphorescent dopant or a delayed fluorescent dopant.

19. The organic light-emitting device of claim 18, wherein the emission layer comprises the organometallic complex in a concentration from about 0.01 weight % to about 15 weight % based on 100 weight % of the emission layer.

20. The organic light-emitting device of claim 16, wherein the organic light-emitting device further comprises an electron transport layer between the emission layer and the second electrode, wherein the electron transport layer comprises an electron transporting organic compound and a metal-containing material.

* * * * *